(12) United States Patent
Matsui et al.

(10) Patent No.: US 10,640,755 B2
(45) Date of Patent: *May 5, 2020

(54) PULLULANASE VARIANTS AND POLYNUCLEOTIDES ENCODING SAME

(71) Applicant: NOVOZYMES A/S, Bagsvaerd (DK)

(72) Inventors: Tomoko Matsui, Chiba (JP); Akihiko Yamagishi, Tokyo (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/016,950

(22) Filed: Jun. 25, 2018

(65) Prior Publication Data

US 2018/0298364 A1    Oct. 18, 2018

Related U.S. Application Data

(62) Division of application No. 15/112,096, filed as application No. PCT/EP2015/051145 on Jan. 21, 2015, now Pat. No. 10,030,237.

(30) Foreign Application Priority Data

Jan. 22, 2014  (EP) .................................. 14152110
Dec. 1, 2014   (EP) .................................. 14195691

(51) Int. Cl.
| | |
|---|---|
| *C12N 9/44* | (2006.01) |
| *C12P 7/06* | (2006.01) |
| *C12P 19/02* | (2006.01) |
| *C12P 19/16* | (2006.01) |
| *C12P 7/02* | (2006.01) |
| *C12N 9/00* | (2006.01) |

(52) U.S. Cl.
CPC .............. *C12N 9/2457* (2013.01); *C12P 7/06* (2013.01); *C12P 19/02* (2013.01); *C12P 19/16* (2013.01); *C12Y 302/01041* (2013.01); *C12P 2203/00* (2013.01); *Y02E 50/17* (2013.01)

(58) Field of Classification Search
CPC ......... C12P 19/16; C12P 2203/00; C12P 7/06; C12P 19/02; C12Y 302/01041; C12N 9/2457; Y02E 50/17
See application file for complete search history.

(56) References Cited

U.S. PATENT DOCUMENTS

| | | | |
|---|---|---|---|
| 5,817,498 A | 10/1998 | Deweer | |
| 6,074,854 A | 6/2000 | Deweer | |
| 6,265,197 B1 | 7/2001 | Bisgaard-Frantzen | |
| 6,350,599 B1 | 2/2002 | Svendsen | |
| 8,021,863 B2 | 9/2011 | Viksoe-Nielsen | |
| 9,951,323 B2 * | 4/2018 | Matsui ............. | C12Y 302/0104 |
| 10,030,237 B2 * | 7/2018 | Matsui ................. | C12N 9/2457 |
| 2017/0051265 A1 | 2/2017 | Matsui | |

FOREIGN PATENT DOCUMENTS

| | | |
|---|---|---|
| CN | 102876650 A | 1/2013 |
| WO | 00/01796 A2 | 1/2000 |
| WO | 01/51620 A2 | 7/2001 |
| WO | 2009/075682 A1 | 6/2009 |

OTHER PUBLICATIONS

Duan et al, 2013, Appl Environ Microbiol 79 (13), 4072-4077.
WO 2001-051620 A2 Gene Aceess No. AAE05704.
Broun et al, 1998, Science 282, 1315-1317.
Devos et al, 2000, Proteins Struc, Func, Genet 41, 98-107.
Seffernick et al, 2001, J Bacteriol 183(8), 2405-2410.
Whisstock et al, 2003, Quart Rev Biophys 36(3), 307-340.
Witkowshki et al, 1999, Biochemistry 38, 11643-11650.

* cited by examiner

*Primary Examiner* — Ganapathirama Raghu
(74) *Attorney, Agent, or Firm* — Elias Lambiris

(57) ABSTRACT

The present invention relates to pullulanase variants comprising substitutions of the parent pullulanase at one or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3. The present invention also relates to polynucleotides encoding the variants; nucleic acid constructs, vectors, and host cells comprising the polynucleotides; and methods of using the variants.

28 Claims, No Drawings
Specification includes a Sequence Listing.

PULLULANASE VARIANTS AND POLYNUCLEOTIDES ENCODING SAME

CROSS-REFERENCE TO RELATED APPLICATIONS

This application is a divisional of U.S. application Ser. No. 15/112,096 filed Jul. 15, 2016, now U.S. Pat. No. 10,030,237, which is a 35 U.S.C. 371 national application of PCT/EP2015/051145 filed Jan. 21, 2015, which claims priority or the benefit under 35 U.S.C. 119 of European application nos. 14152110.4 and 14195691.2 filed Jan. 22, 2014 and Dec. 1, 2014, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to pullulanase variants, polynucleotides encoding the variants, methods of producing the variants, and methods of using the variants. Also described is the use of pullulanase of the invention for starch conversion to produce fermentation products. The invention also relates to a composition comprising a pullulanase of the invention.

Description of the Related Art

Starch usually consists of about 80% amylopectin and 20% amylose. Amylopectin is a branched polysaccharide in which linear chains alpha-1,4 D-glucose residues are joined by alpha-1,6 glucosidic linkages. Amylopectin is partially degraded by alpha-amylase, which hydrolyzes the 1,4-alpha-glucosidic linkages to produce branched and linear oligosaccharides. Prolonged degradation of amylopectin by alpha-amylase results in the formation of so-called alpha-limit dextrins that are not susceptible to further hydrolysis by the alpha-amylase. Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Debranching enzymes which can attack amylopectin are divided into two classes: isoamylases (E.C. 3.2.1.68) and pullulanases (E.C. 3.2.1.41), respectively. Isoamylase hydrolyses alpha-1,6-D-glucosidic branch linkages in amylopectin and beta-limit dextrins and can be distinguished from pullulanases by the inability of isoamylase to attack pullulan, and by their limited action on alpha-limit dextrins.

It is well-known in the art to add isoamylases or pullulanases in starch conversion processes. Pullulanase is a starch debranching enzyme having pullulan 6-glucano-hydrolase activity (EC3.2.1.41) that catalyzes the hydrolyses the α-1,6-glycosidic bonds in pullulan, releasing maltotriose with reducing carbohydrate ends. Usually pullulanase is used in combination with an alpha amylase and/or a glucoamylase.

Pullulanases are known in the art. U.S. Pat. Nos. 6,074,854 and 5,817,498 disclose a pullulanase from *Bacillus deramificans*. WO2009/075682 disclose a pullulanase derived from *Bacillus acidopullulyticus*.

The present invention provides pullulanase variants with improved properties compared to its parent.

SUMMARY OF THE INVENTION

The present invention relates to a pullulanase variant comprising a substitution at one or more positions corresponding to positions 393, 143, 150, 243, 244, 346, 368, 370, 373, 381, 385, 387, 402, 429, 430, 456, 486, 492, 610, 631, 632, 665 and 699 of the polypeptide of SEQ ID NO: 3 wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In a further aspect the present invention relates to a variant catalytic domain, wherein the variant catalytic domain comprises a substitution at one or more positions corresponding to positions 393, 346, 368, 370, 373, 381, 385, 387, 402, 429, 430, 456, 486, 492, 610, 631, 632, 665 and 699 of the polypeptide of SEQ ID NO: 3; and a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

The present invention further relates to a pullulanase variant comprising the variant catalytic domain of the invention, wherein the pullulanase variant has pullulanase activity and increased thermoactivity compared to the parent pullulanase, and the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%.

In a still further aspect the invention relates to compositions comprising the pullulanase variants of the invention.

The present invention also relates to polynucleotides encoding the variants; nucleic acid constructs, vectors, and host cells comprising the polynucleotides; and methods of producing the variants.

The present invention also relates to methods of producing a fermentation product from a starch containing material.

Definitions

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to the procedure described in the Examples. In the context of the present invention the variant pullulanases have improved thermoactivity. Increased thermoactivity was determined as relative activity when measured at 70° C. relative to activity at 65° C. using the PHADEBAS assay as described in the examples.

In particular the pullulanase variants of the invention have at least 60% relative activity when measured at 70° C. relative to activity at 65° C., more particularly at least 70%, more particularly at least 80%, more particularly at least 90%, more particularly at least 100% when comparing variants of SEQ ID NO: 3.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 6.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 9.

Pullulanase domains, CBM41, X45, X25: According to NCBI's CDD (conserved domain database, Marchler-Bauer et al., Nucleic acids research 2011, vol. 39, D225-229), X25, X45 and CBM41 domains in pullulanases are described as follows:

X25 Domain of *Bacillus acidopullulyticus* Pullulanase and Similar Proteins.

Pullulanase (EC 3.2.1.41) cleaves 1.6-alpha-glucosidic linkages in pullulan, amylopectin, and glycogen, and in alpha- and beta-amylase limit-dextrins of amylopectin and glycogen. *Bacillus acidopullulyticus* pullulanase is used industrially in the production of high fructose corn syrup, high maltose content syrups and low calorie and "light" beers. Pullulanases, in addition to the catalytic domain, include several carbohydrate-binding domains (CBMs) as well as domains of unknown function (termed "X" modules). X25 was identified in *Bacillus acidopullulyticus* pullulanase, and splits another domain of unknown function (X45). X25 is present in multiple copies in some pullulanases. It has been suggested that X25 and X45 are CBMs which target mixed alpha-1.6/alpha-1.4 linked D-glucan polysaccharides.

X45 Domain of *Bacillus acidopullulyticus* Pullulanase and Similar Proteins.

Pullulanase (EC 3.2.1.41) cleaves 1.6-alpha-glucosidic linkages in pullulan, amylopectin, and glycogen, and in alpha- and beta-amylase limit-dextrins of amylopectin and glycogen. *Bacillus acidopullulyticus* pullulanase is used industrially in the production of high fructose corn syrup, high maltose content syrups and low calorie and "light" beers. Pullulanases, in addition to the catalytic domain, include several carbohydrate-binding domains (CBMs) as well as domains of unknown function (termed "X" modules). X45 was identified in *Bacillus acidopullulyticus* pullulanase; it is interrupted by another domain of unknown function (X25). It has been suggested that X25 and X45 are CBMs which target mixed alpha-1.6/alpha-1.4 linked D-glucan polysaccharides.

Family 41 Carbohydrate-Binding Module from Pullulanase-Like Enzymes

Pullulanases (EC 3.2.1.41) are a group of starch-debranching enzymes, catalyzing the hydrolysis of the alpha- 1.6-glucosidic linkages of alpha-glucans, preferentially pullulan. Pullulan is a polysaccharide in which alpha-1.4 linked maltotriosyl units are combined via an alpha-1.6 linkage. These enzymes are of importance in the starch industry, where they are used to hydrolyze amylopectin starch. Pullulanases consist of multiple distinct domains, including a catalytic domain belonging to the glycoside hydrolase (GH) family 13 and carbohydrate-binding modules (CBM), including CBM41. Carbohydrate-Binding Module family 41, are modules of approx. 100 residues found primarily in bacterial pullulanases. CBM41 alias PUD (Bacterial pullulanase-associated domain) modules, may be identified in a query protein sequence, by using the Pfam database 'Sequence Search' tool available at pfam.xfam.orq/search, using Pfam version 26.0 or higher. The Pfam database is a large collection of protein families, each represented by multiple sequence alignments and hidden Markov models (HMMs). Pfam is freely available under the Creative Commons Zero ("CC0") license (see creativecommons.org/publicdomain/zero/1.0/).

The query protein sequence in FASTA format is entered into the search field of the Pfam database Sequence Search tool available via the internet at pfam.xfam.orq/search, and the Submit button is pressed, after which the Sequence Search results are displayed in a table showing Significant Pfam-A Matches, hereafter Table.

The presence of Table rows containing the Family name PUD are positive identifications of the presence of CBM41 alias PUD modules in the query protein sequence. The PUD Family name may also be referred to as PF03714 without loss of ambiguity.

Additional columns in the Table show Envelope Start and End coordinates, which define respectively start and end coordinates of the CBM41 alias PUD module in the query sequence, hereafter sequence Region which encompasses sequence start to end inclusive.

An additional column in the Table shows E-value, which refers to the statistical significance of the CBM41 alias PUD module identification. Lower E-values are statistically more significant than higher E-values. Significant CBM41 alias PUD module identifications are defined as those having as having an E-value less than 1.0, preferably an E-value less than 1e-2 (0.01), more preferably an E-value less than 1e-4 (0.0001), even more preferably an E-value less than 1e-6 (0.000001).

Some pullulanases contain all these domains at their N-terminal and some lack either one or two or all of these domains.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has pullulanase activity.

Hybrid pullulanase: Hybrid pullulanases according to the invention are obtained by combining an N-terminal fragment of one pullulanase fused to a C-terminal fragment of another pullulanase. Preferably the fusion is taking place within the catalytic domain where at least part of the catalytic domain in the hybrid pullulanase should be derived from the catalytic domain comprised in Promozyme D2 (SEQ ID NO: 5), however, other fusion points are also possible. The fusion could be a simple fusion between two fragments origination from the two parent pullulanases, however, the fusion could in some embodiments give rise to a shuffled amino acid sequence in the interface between the two parent fragments. Fusion should preferably be performed in a region homology between the parent pullulanases. The homologous region should at least be 4 amino acids.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, specific activity, thermo-stability and thermo-activity. In a particular embodiment the improved property is increased thermoactivity. In another particular embodiment the improved property is increased thermostability. In another particular embodiment the improved property is increased specific activity.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Isoamylase: The term "isoamylase" means a starch debranching enzyme activity (E.C. 3.2.1.68) that hydrolyses alpha-1,6-D-glucosidic branch linkages in amylopectin and beta-limit dextrins and can be distinguished from pullulanases by the inability of isoamylase to attack pullulan, and by the limited action on alpha-limit dextrins. Isoamylase may be added in effective amounts well known to the person skilled in the art. Isoamylase may be added alone or together with a pullulanase.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 34 to 861 of SEQ ID NO: 2 and amino acids 1 to 33 of SEQ ID NO: 2 are a signal peptide. In another aspect, the mature polypeptide is amino acids 30 to 957 of SEQ ID NO: 5 and amino acids 1 to 29 of SEQ ID NO: 5 are a signal peptide. In another aspect, the mature polypeptide is amino acids 34 to 862 of SEQ ID NO: 8 and amino acids 1 to 33 of SEQ ID NO: 8 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having pullulanase activity. In one aspect, the mature polypeptide coding sequence is nucleotides 100 to 2583 of SEQ ID NO: 1. Nucleotides 1 to 99 of SEQ ID NO: 1 encode a signal peptide. In another aspect, the mature polypeptide coding sequence is nucleotides 88 to 2871 of SEQ ID NO: 4. Nucleotides 1 to 87 of SEQ ID NO: 4 encode a signal peptide. In another aspect, the mature polypeptide coding sequence is nucleotides 100 to 2586 of SEQ ID NO: 7. Nucleotides 1 to 99 of SEQ ID NO: 7 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent pullulanase: The term "parent" or "parent pullulanase or chimera pullulnase means a pullulanase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having pullulanase activity.

Variant: The term "variant" means a polypeptide having pullulanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have increased thermo-activity compared to the parent enzyme.

In particular the pullulanase variants of the invention have at least 60% relative activity when measured at 70° C. relative to activity at 65° C., more particularly at least 70%, more particularly at least 80%, more particularly at least 90%, more particularly at least 100% when comparing variants of SEQ ID NO: 3.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 6.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 9.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 16.

In particular the pullulanase variants of the invention have at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100% when comparing variants of SEQ ID NO: 17.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type Pullulanase: The term "wild-type" pullulanase means a pullulanase expressed by a naturally occurring microorganism, such as a bacterium, yeast, or filamentous fungus found in nature.

Conventions for Designation of Variants

For purposes of the present invention, the mature polypeptide comprised in SEQ ID NO: 2 is used to determine the corresponding amino acid residue in another pullulnase. In one embodiment, the mature polypeptide is disclosed as SED ID NO: 3. The amino acid sequence of another pullulanase is aligned with the mature polypeptide disclosed as SEQ ID NO: 3, and based on the alignment, the amino acid position number corresponding to any amino acid residue in the mature polypeptide disclosed as SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another pullulanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviations are employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to variant pullulanases derived from a hybrid parent pullulanase. The hybrid parent pullulanase is the subject of the copending EP patent application 13176791.5 filed on Jul. 17, 2013. The parent pullulanase, denoted P8, is a hybrid enzyme obtained by combining an N-terminal fragment of the pullulanase derived from *Bacillus acidopullullyticus* described in WO 2009/075682 (SEQ ID NO: 4 in WO2009/075682; GENESEQP: AXB71624), fused to a C-terminal fragment of a pullulanase derived from a *Bacillus deramificans* strain isolated from a humus sample collected in Denmark (a homologous pullulanase from *Bacillus deramificans* was disclosed in U.S. Pat. Nos. 6,074,854 and 5,817,498). The resulting hybrid parent pullulanase is disclosed herein as SEQ ID NO: 2, and the mature pullulanase as SEQ ID NO: 3.

The variants according to the present invention have improved properties compared to the parent. The improved properties are selected from increased thermo-activity or increased specific activity on maltodextrin. In one embodiment the variants of the invention have increased thermo-activity. The positions to be substituted in order to obtain increased thermo-activity will be described in detail below. In addition to the effect observed when substituting any of the disclosed positions in the parent pullulanase (the hybrid enzyme denoted as P8 or P008, and disclosed herein as SEQ ID NO: 3) some positions have also been tested for alternative hybrids or wild type pullulanases. Two such alternative hybrid pullulanases are disclosed herein as SEQ ID NO: 16 and SEQ ID NO: 17. For more details on these specific constructs see the example section herein. The results support the finding that the in particular substitutions performed in the catalytic domain can be introduced at the corresponding positions in other pullulanases, wild type as well as hybrid, and the result will be variant pullulanases having increased thermo-activity. When a specific substitution is tested in a different parent enzyme the starting amino acid present in the parent may be different from the first tested parent. This does not have any effect on the resulting variant. As a general rule the essential feature is the amino acid that will be introduced at a specific position not what was there before the substitution. Thus throughout the specification in many embodiments only the amino acid present after substitution has been given. E.g., 393A means that whatever amino acid present in position 393 should be substituted to A (Ala).

The variants according to the invention comprises one or more substitutions numbered according to the mature polypeptide of SEQ ID NO: 2, disclosed herein as SEQ ID NO: 3. Unless otherwise indicated the position numbers referred to for variants disclosed herein refer to numbering in SEQ ID NO: 3.

The present invention relates to pullulanase variant comprising a substitution at one or more positions corresponding to positions 393, 143, 150, 243, 244, 346, 368, 370, 373, 381, 385, 387, 402, 429, 430, 456, 486, 492, 610, 631, 632, 665 and 699 of the polypeptide of SEQ ID NO: 3 wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Variants

The present invention provides pullulanase variants, comprising a substitution at one or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of SEQ ID NO: 3 wherein the variant has pullulanase activity and increased thermo-activity.

The variants may further comprise one or more additional alteration at one or more other positions. Such additional alterations may not significantly affect the properties of the variants according to the invention but may change the % identity of the variant compared to SEQ ID NO: 3.

In an embodiment, the variant has sequence identity of at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent pullulanase.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3. In one aspect, the number of alterations in the variants of the present invention is 1-20, e.g., 1-10 and 1-5 such as 1, 2, 3, 4, 5, 6, 7, 8, 9 or 10 alterations.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6. In one aspect, the number of alterations in the variants of the present invention is 1-20, e.g., 1-10 and 1-5 such as 1, 2, 3, 4, 5, 6, 7, 8, 9 or 10 alterations.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 9. In one aspect, the number of alterations in the variants of the present invention is 1-20, e.g., 1-10 and 1-5 such as 1, 2, 3, 4, 5, 6, 7, 8, 9 or 10 alterations.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 16. In one aspect, the number of alterations in the variants of the present invention is 1-20, e.g., 1-10 and 1-5 such as 1, 2, 3, 4, 5, 6, 7, 8, 9 or 10 alterations.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 17. In one aspect, the number of alterations in the variants of the present invention is 1-20, e.g., 1-10 and 1-5 such as 1, 2, 3, 4, 5, 6, 7, 8, 9 or 10 alterations.

In a particular embodiment the present invention relates to pullulanase variant comprising a substitution at one or more positions corresponding to positions 393, 143, 150, 243, 244, 346, 368, 370, 373, 381, 385, 387, 402, 429, 430, 456, 486, 492, 610, 631, 632, 665 and 699 of the polypeptide of SEQ ID NO: 3 wherein the variant has pullulanase activity; and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, a variant comprises a substitution at two or more positions corresponding to positions 393, 143, 150, 243, 244, 346, 368, 370, 373, 381, 385, 387, 402, 429, 430, 456, 486, 492, 610, 624, 631, 632, 665 and 699 of the polypeptide of SEQ ID NO: 3 wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, a variant comprises a substitution at three or more positions corresponding to positions 393, 143, 150, 243, 244, 346, 368, 370, 373, 381, 385, 387, 402, 429, 430, 431, 456, 486, 492, 610, 624, 631, 632, 665 and 699 of the polypeptide of SEQ ID NO: 3 wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, a variant comprises a substitution at four or more positions corresponding to positions 393, 143, 150, 243, 244, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, a variant comprises a substitution at five or more positions corresponding to positions 393, 143, 150, 243, 244, 345, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant has pullulanase activity, and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, a variant comprises a substitution at six or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699.

In another aspect, a variant comprises a substitution at one position corresponding to positions 393, 143, 150, 243, 244, 346, 368, 456, 492, 610, 624, or 699 of the polypeptide of SEQ ID NO: 3 wherein the variant has pullulanase activity, and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of a substitution at a position corresponding to position 393. In another aspect, the amino acid at a position corresponding to position 393 is substituted with Ala, Arg, Asp, Cyt, Glu, Gln, Gly, His, Ile, Leu, Lys, Met, Phe, Pro, Ser, Thr, Trp, Tyr or Val, preferably with Ala. In another aspect, the variant comprise or consist of the substitution N393A of the polypeptide of SEQ ID NO: 3.

In another aspect, the variant comprises or consists of a substitution at a position corresponding to position 143. In another aspect, the amino acid at a position corresponding to position 143 is substituted with Ala, Arg, Asn, Asp, Cys, Glu, Gln, Gly, His, Ile, Leu, Lys, Met, Phe, Pro, Ser, Thr, Trp or Tyr, preferably with Gly. In another aspect, the variant comprise or consist of the substitution V143G of the polypeptide of SEQ ID NO: 3.

In another aspect, the variant comprises or consists of a substitution at a position corresponding to position 150. In another aspect, the amino acid at a position corresponding to position 150 is substituted with Ala, Arg, Asn, Asp, Cys, Gln, Gly, His, Ile, Leu, Lys, Met, Phe, Pro, Ser, Thr, Trp, Tyr or Val, preferably with Arg. In another aspect, the variant comprise or consist of the substitution E150R of the polypeptide of SEQ ID NO: 3.

In another aspect, the variant comprises or consists of a substitution at a position corresponding to position 243. In another aspect, the amino acid at a position corresponding to position 243 is substituted with Ala, Arg, Asp, Cys, Glu, Gln, Gly, His, Ile, Leu, Lys, Met, Phe, Pro, Ser, Thr, Trp, Tyr or Val, preferably with Glu. In another aspect, the variant comprise or consist of the substitution N243E of the polypeptide of SEQ ID NO: 3.

In another aspect, the variant comprises or consists of a substitution at a position corresponding to position 244. In another aspect, the amino acid at a position corresponding to position 244 is substituted with Ala, Arg, Asn, Asp, Cys, Glu, Gln, Gly, His, Ile, Leu, Lys, Met, Phe, Pro, Thr, Trp, Tyr or Val, preferably with Lys. In another aspect, the variant comprise or consist of the substitution S244K of the polypeptide of SEQ ID NO: 3.

In another aspect, the variant comprises or consists of a substitution at a position corresponding to position 345. In another aspect, the amino acid at a position corresponding to position 346 is substituted with Arg, Asn, Asp, Cys, Glu, Gln, Gly, His, Ile, Leu, Lys, Met, Phe, Pro, Ser, Thr, Trp, Tyr or Val, preferably with Pro. In another aspect, the variant comprise or consist of the substitution A345P of the polypeptide of SEQ ID NO: 3.

In another aspect, the variant comprises or consists of a substitution at a position corresponding to position 346. In another aspect, the amino acid at a position corresponding to position 346 is substituted with Ala, Arg, Asp, Cys, Glu, Gln, Gly, His, Ile, Leu, Lys, Met, Phe, Pro, Ser, Thr, Trp, Tyr or Val, preferably with Ser. In another aspect, the variant comprise or consist of the substitution N346S of the polypeptide of SEQ ID NO: 3.

In another aspect, the variant comprises or consists of a substitution at a position corresponding to position 368. In another aspect, the amino acid at a position corresponding to position 368 is substituted with Ala, Arg, Asp, Cys, Glu, Gln, Gly, His, Ile, Leu, Lys, Met, Phe, Pro, Ser, Thr, Trp, Tyr or Val, preferably with Glu. In another aspect, the variant comprise or consist of the substitution N368G of the polypeptide of SEQ ID NO: 3.

In another aspect, the variant comprises or consists of a substitution at a position corresponding to position 370. In another aspect, the amino acid at a position corresponding to position 370 is substituted with Ala, Arg, Asn, Asp, Cys, Glu, Gln, Gly, His, Ile, Leu, Met, Phe, Pro, Ser, Thr, Trp, Tyr or Val, preferably with Ser. In another aspect, the variant comprise or consist of the substitution K370S of the polypeptide of SEQ ID NO: 3.

In another aspect, the variant comprises or consists of a substitution at a position corresponding to position 373. In another aspect, the amino acid at a position corresponding to position 373 is substituted with Ala, Arg, Asn, Asp, Cys, Glu, Gln, Gly, His, Leu, Lys, Met, Phe, Pro, Ser, Thr, Trp, Tyr or Val, preferably with Leu. In another aspect, the variant comprise or consist of the substitution I373L of the polypeptide of SEQ ID NO: 3.

In another aspect, the variant comprises or consists of a substitution at a position corresponding to position 381. In another aspect, the amino acid at a position corresponding to position 381 is substituted with Ala, Arg, Asn, Asp, Cys, Glu, Gln, Gly, His, Leu, Lys, Met, Phe, Pro, Ser, Thr, Trp, Tyr or Val, preferably with Val. In another aspect, the variant comprise or consist of the substitution I381V of the polypeptide of SEQ ID NO: 3.

In another aspect, the variant comprises or consists of a substitution at a position corresponding to position 382. In another aspect, the amino acid at a position corresponding to position 382 is substituted with Ala, Arg, Asp, Cys, Glu, Gln, Gly, His, Ile, Leu, Lys, Met, Phe, Pro, Ser, Thr, Trp, Tyr or Val, preferably with Thr. In another aspect, the variant comprise or consist of the substitution N382T of the polypeptide of SEQ ID NO: 3.

In another aspect, the variant comprises or consists of a substitution at a position corresponding to position 385. In another aspect, the amino acid at a position corresponding to position 385 is substituted with Ala, Arg, Asn, Asp, Cys, Glu, Gly, His, Ile, Leu, Lys, Met, Phe, Pro, Ser, Thr, Trp, Tyr or Val, preferably with Glu. In another aspect, the variant comprise or consist of the substitution Q385E of the polypeptide of SEQ ID NO: 3.

In another aspect, the variant comprises or consists of a substitution at a position corresponding to position 387. In another aspect, the amino acid at a position corresponding to position 387 is substituted with Ala, Arg, Asn, Asp, Cys, Glu, Gly, His, Ile, Leu, Lys, Met, Phe, Pro, Ser, Thr, Trp, Tyr or Val, preferably with Leu. In another aspect, the variant comprise or consist of the substitution Q387L of the polypeptide of SEQ ID NO: 3.

In another aspect, the variant comprises or consists of a substitution at a position corresponding to position 402. In another aspect, the amino acid at a position corresponding to position 402 is substituted with Ala, Arg, Asn, Asp, Cys, Glu, Gln, Gly, His, Ile, Leu, Lys, Phe, Pro, Ser, Thr, Trp, Tyr or Val, preferably with Thr. In another aspect, the variant comprise or consist of the substitution M402T of the polypeptide of SEQ ID NO: 3.

In another aspect, the variant comprises or consists of a substitution at a position corresponding to position 429. In another aspect, the amino acid at a position corresponding to position 429 is substituted with Ala, Arg, Asn, Asp, Cys, Glu, Gln, Gly, His, Leu, Lys, Met, Phe, Pro, Ser, Thr, Trp, Tyr or Val, preferably with Val. In another aspect, the variant comprise or consist of the substitution I429V of the polypeptide of SEQ ID NO: 3.

In another aspect, the variant comprises or consists of a substitution at a position corresponding to position 430. In another aspect, the amino acid at a position corresponding to position 430 is substituted with Ala, Arg, Asn, Asp, Cys, Glu, Gln, Gly, His, Ile, Leu, Lys, Met, Phe, Pro, Ser, Trp, Tyr or Val, preferably with Arg. In another aspect, the variant comprise or consist of the substitution T430R of the polypeptide of SEQ ID NO: 3.

In another aspect, the variant comprises or consists of a substitution at a position corresponding to position 431. In another aspect, the amino acid at a position corresponding to position 431 is substituted with Ala, Arg, Asn, Asp, Cys, Glu, Gly, His, Ile, Leu, Lys, Met, Phe, Pro, Ser, Thr, Trp, Tyr or Val, preferably with Glutamic Acid. In another aspect, the variant comprise or consist of the substitution Q431E of the polypeptide of SEQ ID NO: 3.

In another aspect, the variant comprises or consists of a substitution at a position corresponding to position 432. In another aspect, the amino acid at a position corresponding to position 432 is substituted with Ala, Arg, Asn, Asp, Cys, Glu, Gln, Gly, His, Ile, Lys, Met, Phe, Pro, Ser, Thr, Trp, Tyr or Val, preferably with Phe. In another aspect, the variant comprise or consist of the substitution L432F of the polypeptide of SEQ ID NO: 3.

In another aspect, the variant comprises or consists of a substitution at a position corresponding to position 456. In another aspect, the amino acid at a position corresponding to position 456 is substituted with Ala, Arg, Asn, Asp, Cys, Glu, Gln, Gly, His, Ile, Leu, Lys, Met, Pro, Ser, Thr, Trp, Tyr or Val, preferably with Ala. In another aspect, the variant comprise or consist of the substitution F456A of the polypeptide of SEQ ID NO: 3.

In another aspect, the variant comprises or consists of a substitution at a position corresponding to position 486. In another aspect, the amino acid at a position corresponding to position 486 is substituted with Ala, Arg, Asn, Asp, Cys, Glu, Gln, Gly, His, Ile, Leu, Lys, Met, Phe, Pro, Ser, Thr, Trp or Tyr, preferably with Cys. In another aspect, the variant comprise or consist of the substitution V486C of the polypeptide of SEQ ID NO: 3.

In another aspect, the variant comprises or consists of a substitution at a position corresponding to position 492. In another aspect, the amino acid at a position corresponding to position 492 is substituted with Ala, Arg, Asn, Asp, Cys, Glu, Gln, Gly, His, Ile, Leu, Lys, Met, Phe, Pro, Ser, Trp, Tyr or Val, preferably with Ser or Ala. In another aspect, the variant comprise or consist of the substitution T492S,A of the polypeptide of SEQ ID NO: 3.

In another aspect, the variant comprises or consists of a substitution at a position corresponding to position 610. In another aspect, the amino acid at a position corresponding to position 610 is substituted with Ala, Arg, Asp, Cys, Glu, Gin, Gly, His, Ile, Leu, Lys, Met, Phe, Pro, Ser, Thr, Trp, Tyr or Val, preferably with Leu or Arginine. In another aspect, the variant comprise or consist of the substitution N610L or N610R of the polypeptide of SEQ ID NO: 3.

In another aspect, the variant comprises or consists of a substitution at a position corresponding to position 624. In another aspect, the amino acid at a position corresponding to position 624 is substituted with Ala, Arg, Asn, Asp, Cys, Glu, Gin, His, Ile, Leu, Lys, Met, Phe, Pro, Ser, Thr, Trp, Tyr or Val, preferably with Ser. In another aspect, the variant comprise or consist of the substitution G624S of the polypeptide of SEQ ID NO: 3.

In another aspect, the variant comprises or consists of a substitution at a position corresponding to position 631. In another aspect, the amino acid at a position corresponding to position 631 is substituted with Ala, Arg, Asn, Asp, Cys, Glu, Gin, Gly, His, Ile, Leu, Lys, Met, Phe, Pro, Ser, Trp, Tyr or Val, preferably with Ser. In another aspect, the variant comprise or consist of the substitution T631S of the polypeptide of SEQ ID NO: 3.

In another aspect, the variant comprises or consists of a substitution at a position corresponding to position 632. In another aspect, the amino acid at a position corresponding to position 632 is substituted with Ala, Arg, Asn, Asp, Cys, Glu, Gin, Gly, His, Ile, Leu, Lys, Met, Phe, Pro, Thr, Trp, Tyr or Val, preferably with Cys. In another aspect, the variant comprise or consist of the substitution S632C of the polypeptide of SEQ ID NO: 3.

In another aspect, the variant comprises or consists of a substitution at a position corresponding to position 665. In another aspect, the amino acid at a position corresponding to position 665 is substituted with Ala, Arg, Asn, Asp, Cys, Glu, Gin, Gly, His, Ile, Leu, Lys, Met, Phe, Pro, Ser, Thr, Trp or Tyr, preferably with Ile. In another aspect, the variant comprise or consist of the substitution V665I of the polypeptide of SEQ ID NO: 3.

In another aspect, the variant comprises or consists of a substitution at a position corresponding to position 699. In another aspect, the amino acid at a position corresponding to position 699 is substituted with Ala, Arg, Asn, Asp, Cys, Gin, Gly, His, Ile, Leu, Lys, Met, Phe, Pro, Ser, Thr, Trp, Tyr, Val, preferably with Arg. In another aspect, the variant comprise or consist of the substitution E699R of the polypeptide of SEQ ID NO: 3.

In another aspect, the variant comprises or consists of one or more substitutions selected from the group consisting of 393A, 143G, 150R, 243E, 244K, 345P, 346S, 368G, 370S, 373L, 381V, 382T, 385F, 387L, 402T, 429V, 430R, 431E, 432F, 456A, 486C, 492S,A, 610R,L, 624S, 631S, 632C, 665I and 699R, wherein position numbering refers to SEQ ID NO: 3. Throughout the present description in many occasions only the specific amino acids that should be present after the substitution is given. This is due to the fact that we have tested and found the substitutions can be introduced in many different parent pullulanase and still result in the same improved effect. The different parent pullulanases will not all have the same amino acid in the same corresponding specific position before substitution. Thus in order to obtain the described effect the essential feature is the specific amino acid present in a specific position after substitution.

In another aspect, the variant comprises or consists of substitutions at positions corresponding to positions 368G and 393A, wherein the variant has pullulanase activity; and a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions and 393A and 431E, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO:

6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%;

b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 432F, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO:

9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 431E and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 432F and 610R, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 432F and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO:

9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 431E and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 393A and 431E and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In another aspect, the variant comprises or consists of substitutions at positions corresponding to positions 368G and 393A and 431E and 432F and 610R and 624S, wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In a further particular embodiment the variant of the invention comprises at least one of the following substitutions or combinations of specific substitutions of the polypeptide of SEQ ID NO: 3 or in a corresponding position in the polypeptides of SEQ ID NO: 6, SEQ ID NO: 9, SEQ ID NO: 16, SEQ ID NO: 17:

N368G;
E699R;
E150R;
N346S;
N243E;
S244K;
V143G;
N393A;
N610R;
N610L;
G624S;
F456A;
T492S,A;
V486C+T492S,A;
N368G+M402T;
T631S+S632C;
V486C+T492S,A+T631S+S632C;
N393A+T631S+S632C;
T631S+S632C+E699R;
N393A+V486C+T492S,A+T631S+S632C;
N393A+G624S+S632C;
N393A+N610R+T631S+S632C;
N393A+G624S+T631S+S632C;
N393A+N610R+G624S+T631S+S632C;
N393A+V486C+T492S,A+G624S+T631S+S632C;
N393A+V486C+T492S,A+N610R+G624S+T631S+S632C;
N368G+N393A+V486C+T492S,A+N610R+G624S+T631S+S632C;
N393A+V486C+T492S,A+N610R+G624S+T631S+S632C+E699R;
N346S+N393A+V486C+T492S,A+N610R+G624S+T631S+S632C;
N393A+F456A+V486C+T492S,A+N610R+G624S+T631S+S632C;
N393A+T492S,A+N610R+G624S+T631S+S632C;
N368G+N393A+T492S,A+N610R+G624S+T631S+S632C;
A345P+N393A+V486C+T492S,A+N610R+G624S+T631S+S632C;
N368G+K370S+I373L+N393A+V486C+T492S,A+N610R+G624S+T631S+S632C;
I381V+Q385E+Q387L+N393A+V486C+T492S,A+N610R+G624S+T631S+S632C;
I381V+N382T+Q385E+Q387L+N393A+V486C+T492S,A+N610R+G624S+T631S+S632C;
A345P+N368G+N393A+T492S,A+N610R+G624S+T631S+S632C;
N368G+I381V+Q385E+Q387L+N393A+T492S,A+N610R+G624S+T631S+S632C;
A345P+N368G+I381V+Q385E+Q387L+N393A+T492S,A+N610R+G624S+T631S+S632C;
A345P+N368G+I381V+Q385E+Q387L+N393A+T492S,A+N610R+G624S+T631S+S632C+V665I;
N393A+T430R+Q431E+L432F+V486C+T492S,A+N610R+G624S+T631S+S632C;

N393A+Q431E+L432F+V486C+T492S,A+N610R+ G624S+T631S+S632C;
N393A+I429V+Q431E+V486C+T492S,A+N610R+ G624S+T631S+S632C;
N393A+I429V+T430R+Q431E+L432F+V486C+T492S, A+N610R+G624S+T631S+S632C;
N368G+N393A+A492S,A;
N368G+N393A;
N393A+N610R;
N368G+N393A+N610R;
N368G+N393A+T492S,A+N610R+G624S;
N368G+N393A+T492S,A+N610R+G624S+T631S+ S632C+Q431E+L432F;
N368G+N393A+N610R+G624S+T631S+S632C;
N368G+N393A+T492S,A+N610R+G624S+T631S+ S632C; or
N368G+N393A+N610R+G624S+T631S+S632C+Q431E+ L432F;
and wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

In a further particular embodiment the variant of the invention comprises at least one of the following substitutions or combinations of specific substitutions of the polypeptide of SEQ ID NO: 3 or in a corresponding position in the polypeptides of SEQ ID NO: 6, SEQ ID NO: 9, SEQ ID NO: 16, SEQ ID NO: 17:
N368G;
N393A;
N610R;
G624S;
T492S,A;
N393A+V486C+T492S,A+N610R+G624S+T631S+ S632C;
N393A+T492S,A+N610R+G624S+T631S+S632C;
N368G+N393A+T492S,A+N610R+G624S+T631S+ S632C;
N368G+N393A+A492S,A;
N368G+N393A+T492S,A+N610R+G624S;
N368G+N393A+T492S,A+N610R+G624S+T631S+ S632C+Q431E+L432F;
N368G+N393A+N610R+G624S+T631S+S632C;
N368G+N393A+N610R+G624S+T631 S+S632C+Q431E+ L432F;
and wherein the variant has pullulanase activity, and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

More specifically the invention relates in one embodiment to pullulanase variants, comprising the substitution N368G of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution E150R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N346S of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N243E of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution S244K of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution V143G of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N610R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N610L of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution G624S of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution F456A of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution T492S,A of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution V486C+T492S,A of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N368G+M402T of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution V486C+T492S,A+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution T631S+S632C+E699R of the polypeptide of SEQ ID NO: 3 wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+G624S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+N610R+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N368G+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C+E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C+E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C+E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C+E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+V486C+T492S,A+N610R+G624S+T631S+S632C+E699R of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N346S+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+F456A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N368G+N393A+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution A345P+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N368G+K370S+I373L+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution I381V+Q385E+Q387L+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution I381V+N382T+Q385E+Q387L+N393A+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution A345P+N368G+N393A+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N368G+I381V+Q385E+Q387L+N393A+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution A345P+N368G+I381V+Q385E+Q387L+N393A+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution A345P+N368G+I381V+Q385E+Q387L+N393A+T492S,A+N610R+G624S+T631S+S632C+V665I of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+T430R+Q431E+L432F+V486C+T492S,A+N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+ Q431E+L432F+V486C+T492S,A+N610R+G624S+ T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+ I429V+Q431E+V486C+T492S,A+N610R+G624S+ T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to pullulanase variants, comprising the substitution N393A+ I429V+T430R+Q431E+L432F+V486C+T492S,A+ N610R+G624S+T631S+S632C of the polypeptide of SEQ ID NO: 3, wherein the variant has pullulanase activity, and wherein the pullulanase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

All of the above specific substitutions or combinations of substitutions have an effect of increased thermoactivity of the resulting variant when introduced in the parent disclosed as SEQ ID NO: 3. In order to test the effect of the specific substitutions in a different parent enzyme, several substitutions and combination of substitutions have been introduced in the parent enzyme disclosed herein as SEQ ID NO: 6. All the tested substitutions were shown also to be effective in SEQ ID NO: 6. SEQ ID NO: 6 has an additional 100 amino acids compared to SEQ ID NO: 3. Thus the actual position numbers are +100. The additional 100 amino acids constitute what is known as an X25 domain (domain of unknown function) of 104 amino acids and deletions corresponding to 4 amino acids in the N-terminal part. The X25 domain is found in the N-terminal part of SEQ ID NO: 6 in positions 158-261, upstream of the catalytic domain.

In a particular embodiment the variant of the invention comprises at least one of the following substitutions or combinations of specific substitutions of the polypeptide of SEQ ID NO: 3 or in a corresponding position in the polypeptides of SEQ ID NO: 6:
N368G;
N393A;
N610R;
G624S;
N368G+N393A+A492S,A;
N368G+N393A;
N393A+N610R;
N368G+N393A+N610R;
N368G+N393A+T492S,A+N610R+G624S; and wherein the variant has pullulanase activity, and wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Similarly, in a further embodiments specific combinations of substitutions were tested in parent hybrid pullulanases disclosed herein as SEQ ID NO: 16 and SEQ ID NO: 17.

Thus in a particular embodiment the variant of the invention comprises at least one of the following substitutions or combinations of specific substitutions of the polypeptide of SEQ ID NO: 3 or in a corresponding position in the polypeptides of SEQ ID NO: 16 or SEQ ID NO: 17:
N368G+N393A+N610R+G624S+T631 S+S632C;
N368G+N393A+N610R+G624S+T631S+S632C+Q431E+ L432F;
N368G+N393A+T492S,A+N610R+G624S+T631S+ S632C; or
N368G+N393A+T492S,A+N610R+G624S+T631 S+S632C+Q431E+L432F;
and wherein the variant has pullulanase activity, and wherein the variant has at least 85%, at least 90%, at least 95%, at least 96%, at least 97%, at least 98%, or at least 99%, but less than 100% sequence identity to the polypeptide of SEQ ID NO: 16 or SEQ ID NO: 17 and wherein the variant has increased thermoactivity compared to the pullulanase of SEQ ID NO: 16 or SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

When the parent pullulanase is selected as SEQ ID NO: 6, SEQ ID NO: 16, or SEQ ID NO: 17, which have 100 amino acids more than e.g., SEQ ID NO: 3 the actual positions referring to SEQ ID NO: 6 SEQ ID NO: 16, or SEQ ID NO: 17, numbering will be +100. Thus as an example, N368G+N393A+A492S, would correspond to N468G+N493A+A592S in SEQ ID NO: 6.

Variant Catalytic Domain

The present invention provides a variant catalytic domain, wherein the variant catalytic domain comprises a substitution at one or more positions corresponding to positions 393, 346, 368, 370, 373, 381, 385, 387, 402, 429, 430, 456, 486, 492, 610, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In another aspect, a variant catalytic domain comprises a substitution at two or more positions corresponding to positions 393, 346, 368, 370, 373, 381, 385, 387, 402, 429, 430, 456, 486, 492, 610, 624, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In another aspect, a variant catalytic domain comprises a substitution at three or more positions corresponding to positions 393, 346, 368, 370, 373, 381, 385, 387, 402, 429, 430, 431, 456, 486, 492, 610, 624, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In another aspect, a variant catalytic domain comprises a four or more positions corresponding to positions 393, 346, 368, 370, 373, 381, 385, 387, 402, 429, 430, 431, 432, 456, 486, 492, 610, 624, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In another aspect, a variant catalytic domain comprises a five or more positions corresponding to positions 393, 345, 346, 368, 370, 373, 381, 385, 387, 402, 429, 430, 431, 432, 456, 486, 492, 610, 624, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In another aspect, a variant catalytic domain comprises a substitution at six or more positions corresponding to positions 393, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3; and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

In a further embodiment the present invention relates to a pullulanase variant comprising the variant catalytic domain according to the invention, wherein the pullulanase variant has pullulanase activity and increased thermoactivity compared to the parent pullulanase, and the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%.

The pullulanase variant comprising the variant catalytic domain, comprises one or more substitutions selected from the group consisting of 393A, 345P, 346S, 368G, 370S, 373L, 381V, 382T, 385F, 387L, 402T, 429V, 430R, 431E, 432F, 456A, 486C, 492S,A, 610R,L, 624S, 631S, 632C, 665I and 699R corresponding to positions of polypeptide of SEQ ID NO: 3.

According to the invention several variant catalytic domains (CD) have been constructed and it has further been shown in the examples that the resulting variant pullulanases having increased thermo-activity can be further modified by replacing the N-terminal part of the mature pullulanase and at the same time retain the improved properties, e.g., increased thermo-activity.

Pullulanases may comprise N-terminal parts comprising domains selected from a CBM41 domain, an X45 domain and a CBM48 domain. Thus in one embodiment the pullulanase variant according to the invention, further comprises an N-terminal part comprising at least one of the domains selected from a CBM41 domain, an X45 domain and a CBM48 domain. In one embodiment all of these domains may be present.

The pullulanase variant according to the invention may further comprise an X25 domain. Preferably the N-terminal domains are selected from CBM41, X45, X25, and CBM48 obtainable from a *Bacillus* bacterium. Particularly the *Bacillus* species is *Bacillus acidopullulyticus* or *Bacillus deramificans*.

In a particular embodiment the pullulanase variant according to the invention comprises or consists of one or more substitutions selected from the group consisting of 393A, 368G, 492S,A, 610R,L, 624S, 631S, 632C, 431E, 432F. More particularly the variant catalytic domain comprises at least one of the following substitutions or combinations of substitutions:
368G+393A+492S,A;
368G+393A+T492A,S+610R+624S;
393A+492S,A+610R+624S+631 S+632C;
368G+393A+492S,A+610R+624S+631 S+632C;
368G+393A+492S,A+610R+624S+631   S+632C+431E+ 432F;
368G+393A+610R+624S+631S+632C; or
368G+393A+610R+624S+631S+632C+431E+432F;
and
a) wherein the variant catalytic domain has at least 85%, at least 90%, at least 95%, at least 96%, at least 97%, at least 98%, or at least 99%, but less than 100% sequence identity to amino acids 330 to 828 of SEQ ID NO: 3; or
b) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 6; or
c) wherein the variant catalytic domain has at least 85%, at least 90%, at least 95%, at least 96%, at least 97%, at least 98%, or at least 99%, but less than 100% sequence identity to amino acids 330 to 829 of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Particular examples of variants according to the invention, in which N-terminal part have been replaced are further described in the examples. Thus in further particular embodiments the invention relates to pullulanase variant selected from SEQ ID NO: 20 or a pullulanase having at least 85%, at least 90%, at least 95%, at least 96%, at least 97%, at least 98%, or at least 99%, or 100% sequence identity to the polypeptide of SEQ ID NO: 20, and comprising the substitutions N368G+N393A+N610R+G624S+ T631S+S632C, using SEQ ID NO: 3 for numbering. In another particular embodiment the invention relates to pullulanase variant selected from SEQ ID NO: 21 or a pullulanase having at least 85%, at least 90%, at least 95%, at least 96%, at least 97%, at least 98%, or at least 99%, or 100% sequence identity to the polypeptide of SEQ ID NO: 21, and comprising the substitutions N368G+N393A+ A492S,A, using SEQ ID NO: 3 for numbering. In another particular embodiment the invention relates to pullulanase variant selected from SEQ ID NO: 22 or a pullulanase having at least 85%, at least 90%, at least 95%, at least 96%, at least 97%, at least 98%, or at least 99%, or 100% sequence identity to the polypeptide of SEQ ID NO: 22, and comprising the substitutions N368G+N393A+T492S,A+ N610R+G624S, using SEQ ID NO: 3 for numbering. In another particular embodiment the invention relates to pullulanase variant selected from SEQ ID NO: 23 or a pullulanase having at least 85%, at least 90%, at least 95%, at least 96%, at least 97%, at least 98%, or at least 99%, or 100% sequence identity to the polypeptide of SEQ ID NO: 23, and comprising the substitutions N368G+N393A+ T492S,A+N610R+G624S, using SEQ ID NO: 3 for numbering. In another particular embodiment the invention relates to pullulanase variant selected from SEQ ID NO: 24 or a pullulanase having at least 85%, at least 90%, at least 95%, at least 96%, at least 97%, at least 98%, or at least 99%, or 100% sequence identity to the polypeptide of SEQ ID NO: 24, and comprising the substitutions N368G+ N393A+T492S,A+N610R+G624S+T631S+S632C, using SEQ ID NO: 3 for numbering. In another particular embodiment the invention relates to pullulanase variant selected from SEQ ID NO: 25 or a pullulanase having at least 85%, at least 90%, at least 95%, at least 96%, at least 97%, at least 98%, or at least 99%, or 100% sequence identity to the polypeptide of SEQ ID NO: 25, and comprising the substitutions     N368G+N393A+T492S,A+N610R+G624S+ T631S+S632C, using SEQ ID NO: 3 for numbering. In another particular embodiment the invention relates to pullulanase variant selected from SEQ ID NO: 26 or a pullulanase having at least 85%, at least 90%, at least 95%, at least 96%, at least 97%, at least 98%, or at least 99%, or 100% sequence identity to the polypeptide of SEQ ID NO: 26, and comprising the substitutions N368G+N393A+ N610R+G624S+T631S+S632C+Q431E+L432F, using SEQ ID NO: 3 for numbering. In another particular embodiment the invention relates to pullulanase variant selected from SEQ ID NO: 27 or a pullulanase having at least 85%, at least 90%, at least 95%, at least 96%, at least 97%, at least 98%, or at least 99%, or 100% sequence identity to the polypeptide of SEQ ID NO: 27, and comprising the substitutions N368G+N393A+T492S,A+N610R+G624S+T631S+ S632C+Q431E+L432F, using SEQ ID NO: 3 for numbering. In another particular embodiment the invention relates to pullulanase variant selected from SEQ ID NO: 28 or a pullulanase having at least 85%, at least 90%, at least 95%, at least 96%, at least 97%, at least 98%, or at least 99%, or 100% sequence identity to the polypeptide of SEQ ID NO: 28, and comprising the substitutions N368G+N393A+T492S,A+N610R+G624S+T631S+S632C+Q431E+L432F, using SEQ ID NO: 3 for numbering.

In a further aspect of the invention thermoactivity may be further improved by the addition of further specific substitutions (using SEQ ID NO: 6 for numbering) selected from one of the following substitutions or combinations of substitutions:
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+Q356R;
Y27K+H79Y+H186A+V212I+Q258A+Q287R+N322P+Q352A+Q356R;
Y27K+H79Y+H186A+V212I+Q258A+Q287R+N322P+Q352A+Q356R+D686S;
N19G+Y27K+H79Y+H186A+V212I+Q258A+Q287R+N322P+Q352A+Q356R+D686S;
N19G+Y27K+H79Y+H186A+V212I+Q258A+Q287R+G296R+N322P+Q352A+Q356R+D686S;
Y27K+H79Y+H186A+V212I+Q258A+Q287R+N322P+Q352A+Q356R+V586A+D686S;
Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+V586A+D686S;
N19G+Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+Q485E+D686S+E799R;
N19G+Y27K+H79Y+H186A+V212I+Q258A+Q287R+N322P+Q352A+Q356R+Q487L+D686S+E799R;
N19G+Y27K+H79Y+H186A+V212I+Q258A+Q287R+N322P+Q352A+Q356R+V586A+D686S+E799R;
N19G+Y27K+H79Y+H186A+V212I+Q258A+Q287R+G296R+N322P+Q352A+Q356R+V586A+D686S+E799R;
N19G+Y27K+H79Y+H186A+V212I+Q258A+Q287R+G296R+N322P+Q352A+Q356R+Q487L+V586A+D686S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+S557A+L559G+D686S+E799R;
N19G+Y27K+H79Y+H186A+V212I+Q258A+Q287R+N322P+Q352A+Q356R+H421E+Q487L+S557A+L559G+V586A+D686S+E799R.

In a particular embodiment the invention relates to pullulanase variants selected from a pullulanase having at least 85%, at least 90%, at least 95%, at least 96%, at least 97%, at least 98%, or at least 99% sequence identity to the polypeptide of SEQ ID NO: 26, and comprising the substitutions (using SEQ ID NO: 6 for numbering) N468G+N493A+N710R+G724S+T731S+S732C+Q531E+L532F, and wherein the variants further comprises one of the following substitutions or combinations of substitutions:
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+Q356R;
Y27K+H79Y+H186A+V212I+Q258A+Q287R+N322P+Q352A+Q356R;
Y27K+H79Y+H186A+V212I+Q258A+Q287R+N322P+Q352A+Q356R+D686S;
N19G+Y27K+H79Y+H186A+V212I+Q258A+Q287R+N322P+Q352A+Q356R+D686S;
N19G+Y27K+H79Y+H186A+V212I+Q258A+Q287R+G296R+N322P+Q352A+Q356R+D686S;
Y27K+H79Y+H186A+V212I+Q258A+Q287R+N322P+Q352A+Q356R+V586A+D686S;
Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+V586A+D686S;
N19G+Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+Q485E+D686S+E799R;
N19G+Y27K+H79Y+H186A+V212I+Q258A+Q287R+N322P+Q352A+Q356R+Q487L+D686S+E799R;
N19G+Y27K+H79Y+H186A+V212I+Q258A+Q287R+N322P+Q352A+Q356R+V586A+D686S+E799R;
N19G+Y27K+H79Y+H186A+V212I+Q258A+Q287R+G296R+N322P+Q352A+Q356R+V586A+D686S+E799R;
N19G+Y27K+H79Y+H186A+V212I+Q258A+Q287R+G296R+N322P+Q352A+Q356R+Q487L+V586A+D686S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+S557A+L559G+D686S+E799R;
N19G+Y27K+H79Y+H186A+V212I+Q258A+Q287R+N322P+Q352A+Q356R+H421E+Q487L+S557A+L559G+V586A+D686S+E799R; said variants having at least 60% relative activity when measured at 72° C. relative to activity at 65° C. using the PHADEBAS assay.

In a further particular embodiment the invention relates to pullulanase variants selected from a pullulanase having at least 85%, at least 90%, at least 95%, at least 96%, at least 97%, at least 98%, or at least 99% sequence identity to the polypeptide of SEQ ID NO: 27, and comprising the substitutions (using SEQ ID NO: 6 for numbering) N468G+

N493A+T592S,A+N710R+G724S+T731S+S732C+
Q531E+L532F, and wherein the variants further comprises one of the following substitutions or combinations of substitutions:
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+Q356R;
Y27K+H79Y+H186A+V212I+Q258A+Q287R+N322P+Q352A+Q356R;
Y27K+H79Y+H186A+V212I+Q258A+Q287R+N322P+Q352A+Q356R+D686S;
N19G+Y27K+H79Y+H186A+V212I+Q258A+Q287R+N322P+Q352A+Q356R+D686S;
N19G+Y27K+H79Y+H186A+V212I+Q258A+Q287R+G296R+N322P+Q352A+Q356R+D686S;
Y27K+H79Y+H186A+V212I+Q258A+Q287R+N322P+Q352A+Q356R+V586A+D686S;
Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+V586A+D686S;
N19G+Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+Q485E+D686S+E799R;
N19G+Y27K+H79Y+H186A+V212I+Q258A+Q287R+N322P+Q352A+Q356R+Q487L+D686S+E799R;
N19G+Y27K+H79Y+H186A+V212I+Q258A+Q287R+N322P+Q352A+Q356R+V586A+D686S+E799R;
N19G+Y27K+H79Y+H186A+V212I+Q258A+Q287R+G296R+N322P+Q352A+Q356R+V586A+D686S+E799R;
N19G+Y27K+H79Y+H186A+V212I+Q258A+Q287R+G296R+N322P+Q352A+Q356R+Q487L+V586A+D686S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+S557A+L559G+D686S+E799R;
N19G+Y27K+H79Y+H186A+V212I+Q258A+Q287R+N322P+Q352A+Q356R+H421E+Q487L+S557A+L559G+V586A+D686S+E799R; said variants having at least 60% relative activity when measured at 72° C. relative to activity at 65° C. using the PHADEBAS assay.

In another aspect of the invention thermoactivity may be further improved by the addition of further specific substitutions (using SEQ ID NO: 3 for numbering) selected from one of the following substitutions or combinations of substitutions:
Y27K+H79Y+Q187R+S798R;
Y27K+H79Y+Q187R+D586S+S798R;
Y27K+H79Y+Q187R+D586S+E699R+S798R;
Y27K+H79Y+Q187R+T486S+D586S+S798R;
N19G+Y27K+H79Y+Q187R+T486C+D586S+E699R+S798R;
N19G+Y27K+H79Y+Q187R+Q385E+T486C+D586S+E699R+S798R;
N19G+Y27K+H79Y+Q187R+Q387L+T486C+D586S+E699R+S798R;
N19G+Y27K+H79Y+Q187R+Q387L+Q459G+T486C+D586S+C632S+E699R+S798R;
N19G+Y27K+H79Y+Q187R+Q387L+T486C+D586S+C632S+Q675L+E699R+S798R;
N19G+Y27K+H79Y+Q187R+V196R+Q387L+T486C+D586S+C632S+E699R+S798R;
N19G+Y27K+H79Y+Q187R+V196R+Q387L+T486C+D586S+C632S+Q675L+E699R+S798R;
N19G+Y27K+H79Y+Q187R+V196R+Q387L+Q459G+T486C+D586S+C632S+Q675L+E699R+S798R;
N19G+Y27K+H79Y+Q187R+Q387L+D586S+E699R+S798R;
N19G+Y27K+H79Y+Q187R+H321E+Q387L+D586S+E699R+S798R;
N19G+Y27K+H79Y+Q187R+Q387L+Q459G+D586S+E699R+S798R;
N19G+Y27K+H79Y+Q187R+Q387L+D586S+C632S+E699R+S798R;
N19G+Y27K+H79Y+Q187R+E310A+D311K+Q387L+D586S+E699R+S798R;
N19G+Y27K+H79Y+Q187R+E310A+D311K+Q387L+Q459G+D586S+E699R+S798R.

In a particular embodiment the invention relates to pullulanase variants selected from a pullulanase having at least 85%, at least 90%, at least 95%, at least 96%, at least 97%, at least 98%, or at least 99% sequence identity to the polypeptide of SEQ ID NO: 28, and comprising the substitutions (using SEQ ID NO: 3 for numbering) N368G+N393A+T492S,A+N610R+G624S+T631S+S632C+Q431E+L432F, and wherein the variants further comprises one of the following substitutions or combinations of substitutions:
Y27K+H79Y+Q187R+S798R;
Y27K+H79Y+Q187R+D586S+S798R;
Y27K+H79Y+Q187R+D586S+E699R+S798R;
Y27K+H79Y+Q187R+T486S+D586S+S798R;
N19G+Y27K+H79Y+Q187R+T486C+D586S+E699R+S798R;
N19G+Y27K+H79Y+Q187R+Q385E+T486C+D586S+E699R+S798R;
N19G+Y27K+H79Y+Q187R+Q387L+T486C+D586S+E699R+S798R;
N19G+Y27K+H79Y+Q187R+Q387L+Q459G+T486C+D586S+C632S+E699R+S798R;
N19G+Y27K+H79Y+Q187R+Q387L+T486C+D586S+C632S+Q675L+E699R+S798R;
N19G+Y27K+H79Y+Q187R+V196R+Q387L+T486C+D586S+C632S+E699R+S798R;
N19G+Y27K+H79Y+Q187R+V196R+Q387L+T486C+D586S+C632S+Q675L+E699R+S798R;
N19G+Y27K+H79Y+Q187R+V196R+Q387L+Q459G+T486C+D586S+C632S+Q675L+E699R+S798R;
N19G+Y27K+H79Y+Q187R+Q387L+D586S+E699R+S798R;
N19G+Y27K+H79Y+Q187R+H321E+Q387L+D586S+E699R+S798R;
N19G+Y27K+H79Y+Q187R+Q387L+Q459G+D586S+E699R+S798R;

N19G+Y27K+H79Y+Q187R+Q387L+D586S+C632S+ E699R+S798R;
N19G+Y27K+H79Y+Q187R+E310A+D311K+Q387L+ D586S+E699R+S798R;
N19G+Y27K+H79Y+Q187R+E310A+D311K+Q387L+ Q459G+D586S+E699R+S798R, said variants having at least 30% relative activity when measured at 76° C. relative to activity at 65° C. using the PHADEBAS assay.

The variants may further comprise one or more additional substitutions at one or more (e.g., several) other positions. Such further variation could be introduced without affecting significantly the properties of the pullulanase variants.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R.L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for pullulanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Parent Pullulanase

The parent pullulanase, may be a hybrid enzyme, e.g., P008 (SEQ ID NO: 3), as described herein obtained by combining an N-terminal fragment of the pullulanase derived from *Bacillus acidopullulyticus* described in WO 2009/075682 (SEQ ID NO: 4 in WO2009/075682; GENESEQP: AXB71624), fused to a C-terminal fragment of a pullulanase derived from a *Bacillus deramificans* strain isolated from a humus sample collected in Denmark (a homologous pullulanase from *Bacillus deramificans* was disclosed in U.S. Pat. Nos. 6,074,854 and 5,817,498). Further parent pullulanases disclosed herein include P258, disclosed herein as SEQ ID NO: 16 or P243, disclosed herein as SEQ ID NO: 17, P006 disclosed herein as SEQ ID NO: 19.

The parent pullulanase may also be any wildtype, or variant or hybrid pullulanase that may advantageously be improved by increasing the thermo-activity by introducing one or more substitutions as specified herein.

The parent pullulanase may be (a) a polypeptide having at least 70% sequence identity to the mature polypeptide of SEQ ID NO: 2 or 5 or 8; (b) a polypeptide encoded by a polynucleotide that hybridizes under low stringency conditions with (i) the mature polypeptide coding sequence of SEQ ID NO: 1 or 4 or 7, (ii) the full-length complement of (i) or (c) a polypeptide encoded by a polynucleotide having at least 60% sequence identity to the mature polypeptide coding sequence of SEQ ID NO: 1 or 4 or 7.

In an aspect, the parent has a sequence identity to the mature polypeptide of SEQ ID NO: 2 or 5 or 8 of at least 75%, at least 80%, at least 85%, at least 90%, at least 91%, at least 92%, at least 93%, at least 94%, at least 95%, at least 96%, at least 97%, at least 98%, at least 99%, or 100%, which have pullulanase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2 or 5 or 8.

In another aspect, the parent comprises or consists of the amino acid sequence of SEQ ID NO: 2 or 5 or 8. In another aspect, the parent comprises or consists of the mature polypeptide of SEQ ID NO: 2 or 5 or 8. In another aspect, the parent comprises or consists of amino acids 34 to 861 of SEQ ID NO: 2; 30 to 957 of SEQ ID NO: 5 or 34 to 862 of SEQ ID NO: 8 respectively.

In another embodiment, the parent is an allelic variant of the mature polypeptide of SEQ ID NO: 2 or 5 or 8.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1 or 4 or 7, (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or 4 or 7 and their subsequence thereof, as well as the polypeptide of SEQ ID NO: 2 or 5 or 8 and their fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^3$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or 4 or 7 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or 4 or 7; (ii) the mature polypeptide coding sequence of SEQ ID NO: 1 or 4 or 7; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 4 or 7. In another aspect, the nucleic acid probe is nucleotides 100 to 2583 of SEQ ID NO: 1; nucleotides 88 to 2871 of SEQ ID NO: 4 or nucleotides 100 to 2586 of SEQ ID NO: 7. In another aspect, the nucleic acid probe is a polynucleotide that encodes the polypeptide of SEQ ID NO: 2, 5 or 8; the mature polypeptide thereof; or a fragment thereof. In another aspect, the nucleic acid probe is SEQ ID NO: 1, 4, or 7.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial pullulanase for example, the parent may be a Gram-positive bacterial polypeptide such as a *Bacillus*.

In one aspect, the parent is a *Bacillus acidopullulyticus*, or *Bacillus deramificans* pullulanase.

In another aspect, the parent is a *Bacillus* pullulanase, e.g., the pullulanase of SEQ ID NO: 2 or 5 or 8 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having pullulanase activity, comprising: (a) introducing into a parent pullulanase a substitution at one or more (e.g., several) positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3, 6, 9 or hybrids thereof, wherein the variant has pullulanase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausi, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell, including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397), or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804) or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium mer-

*darium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates method for producing a variant pullulanase of a parent pullulanase comprising substitution of the parent pullulanase at one or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3 wherein the variant has pullulanase activity and increased thermoactivity compared to the parent; and a) wherein the variant has at least 85%, at least 90%, at least 95%, at least 96%, at least 97%, at least 98%, or at least 99%, but less than 100% sequence identity to the polypeptide of SEQ ID NO: 3; or b) wherein the variant has at least 85%, at least 90%, at least 95%, at least 96%, at least 97%, at least 98%, or at least 99%, but less than 100% sequence identity to the polypeptide of SEQ ID NO: 6; or c) wherein the variant has at least 85%, at least 90%, at least 95%, at least 96%, at least 97%, at least 98%, or at least 99%, but less than 100% sequence identity to the polypeptide of SEQ ID NO: 9.

A further embodiment relates to variant pullulanases produced by the method of the invention.

In another aspect, method of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art. A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a pullulanase variant of the present invention. Preferably, the compositions are enriched in such a polypeptide. The term "enriched" indicates that the pullulanase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as the pullulanase variant according to the invention and one or more (e.g., several) enzymes selected from the group consisting of hydrolase, isomerase, ligase, lyase, oxidoreductase, or transferase, e.g., an alpha-galactosidase, alpha-glucosidase, aminopeptidase, alpha-amylase, beta-amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, protease, ribonuclease, transglutaminase, or xylanase. Preferably the enzyme activities comprised in the composition are selected from the hybrid pullulanase according to the invention and one or more enzymes selected from the group consisting of glucoamylase, alpha-amylase, beta-amylase, and protease. In one particular embodiment the composition comprises a pullulanase, a glucoamylase, an alpha-amylase and a protease. In another particular embodiment the composition comprises a pullulanase, an alpha-amylase and a protease. In another particular embodiment the composition comprises a pullulanase, a glucoamylase, and an alpha-amylase. In another particular embodiment the composition comprises a pullulanase, and a beta-amylase.

In a particular embodiment the composition comprises the variant pullulanase of the invention and an alpha amylase. Preferred are bacterial alpha-amylases, which typically are stable at temperatures used during liquefaction. In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be truncated so it has around 491 amino acids compared to SEQ ID NO: 3 in WO 99/19467. Preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467. In a preferred embodiment the alpha-amylase is selected from the group of *Bacillus* stearomthermphilus alpha-amylase variants:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V; and

I181*+G182*+N193F+E129V+K177L+R179E+K220P+N224L+S242Q+Q254S (using SEQ ID NO: 3 disclosed in WO 99/19467 for numbering).

In another preferred embodiment the alpha-amylase is an alpha-amylase derived from *Rhizomucor pusillus* with an *Aspergillus niger* glucoamylase linker and starch-binding domain (SBD), preferably the one shown in SEQ ID NO: 7 in WO2013/006756, preferably having one or more of the following substitutions: G128D, D143N, especially G128D+D143N.

In another particular embodiment the composition comprises the variant pullulanase of the invention, and a protease. In an preferred embodiment the protease is a variant of the *Thermoascus aurantiacus* metallo protease disclosed as SEQ ID NO: 2 in WO 2003/048353, or amino acids 1-177 of SEQ ID NO: 2 in WO 2011/072191, with the following mutations:

D79L+S87P+A112P+D142L;

D79L+S87P+D142L; or

A27K+D79L+Y82F+S87G+D104P+A112P+A126V+D142L.

In another embodiment the protease is derived from a strain of the bacterium *Pyrococcus*, such as a strain of *Pyrococcus furiosus* (pfu protease)

In an embodiment the protease is the one shown as SEQ ID NO: 1 in U.S. Pat. No. 6,358,726-B1. In another embodiment the protease is the one shown as SEQ ID NO: 13 in WO2012/088303.

In another particular embodiment the composition comprises the hybrid pullulanase of the invention, and a glucoamylase. In a specific embodiment the glucoamylase is from a strain of the genus *Penicillium*, especially a strain of *Penicillium oxalicum*, in particular the *Penicillium oxalicum* glucoamylase disclosed as SEQ ID NO: 2 in WO 2011/127802. In a preferred embodiment the glucoamylase is a variant of the *Penicillium oxalicum* glucoamylase disclosed as SEQ ID NO: 2 in WO 2011/127802 having a K79V substitution using the mature polypeptide (amino acids 22-616 of SEQ ID NO: 2) for numbering, and described in WO 2013/036526. In a preferred embodiment the glucoamylase is a variant of the *Penicillium oxalicum* glucoamylase disclosed as amino acids 22-616 of SEQ ID NO: 2 in WO 2011/127802, having a K79V substitution and one or more of the following substitutions P2N, P4S, P11F, T65A, Q327F, especially P2N+P4S+P11F+T65A+Q327F as described in WO2013/053801.

In a specific embodiment the glucoamylase is from a strain of the genus *Pycnoporus*, especially a strain of *Pycnoporus sanguineus*, in particular the *Pycnoporus sanguineus* glucoamylase disclosed as SEQ ID NO: 2, 4, or 6 in WO 2011/066576. In a preferred embodiment the enzyme composition comprises the glucoamylase shown as amino acids 19-573 of SEQ ID NO: 6 in WO 2011/066576.

In a specific embodiment the glucoamylase is from a strain of the genus Gloeophillum, especially a strain of *Gloeophyllum trabeum*, in particular the *Gloeophyllum trabeum* glucoamylase disclosed as SEQ ID NO: 18 in WO 2011/068803. In an especially preferred embodiment the enzyme composition comprises the *Gloeophyllum trabeum* glucoamylase shown in amino acids 18-576 of SEQ ID NO: 18 in WO2011/068803, and having one or more of the following substitutions: S95P, A121P, especially S95P+A121P using the mature polypeptide (positions 18-576 of SEQ ID NO: 18) for numbering.

In a specific embodiment the glucoamylase is from a strain of the genus Gloeophillum, especially a strain of Gloeophillum sepiarium, in particular the mature Gloeophillum sepiarium glucoamylase disclosed as amino acids 18-573 of SEQ ID NO: 2 in WO2011/068803.

In a particular embodiment the composition comprises a variant pullulanase of the invention and a glucoamylase and optionally an alpha-amylase, and wherein the pullulanase is selected from a polypeptide having at least 93%, at least 94%, at least 95%, at least 96%, at least 97%, at least 98%, at least 99% or 100% sequence identity to the mature polypeptide of SEQ ID NO: 21 herein, and comprising the substitutions N368G+N393A+A492S, using SEQ ID NO: 3 for numbering, and the glucoamylase is selected from i) a variant *Gloeophyllum trabeum* glucoamylase, which comprises the substitutions S95P+A121P compared to the wild type *Gloeophyllum trabeum* glucoamylase amino acid sequence set forth in amino acids 18-576 of SEQ ID NO: 18 in WO 2011/068803; or ii) a variant having at least 85%, at least 90%, at least 91%, at least 92%, at least 93%, at least 94%, at least 95%, at least 96%, at least 97%, at least 98%, at least 99% sequence identity to amino acids 18-576 of SEQ ID NO: 18 in WO 2011/068803, and the alpha-amylase is selected from: i) a variant *Rhizomucor pusillus* alpha-amylase with an *Aspergillus niger* glucoamylase linker and starch-binding domain (SBD), which comprises the substitutions G128D+D143N compared to the hybrid *Rhizomucor pusillus* alpha-amylase amino acid sequence set forth in SEQ ID NO: 7 in WO2013/006756; or ii) a variant having at least 85%, at least 90%, at least 91%, at least 92%, at least 93%, at least 94%, at least 95%, at least 96%, at least 97%, at least 98%, at least 99% sequence identity to the polypeptide of SEQ ID NO: 7 in WO2013/006756.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Methods of Using the Pullulanase Variants—Industrial Applications

The present invention is also directed to methods of using polypeptide of present invention in various industrial applications.

The polypeptide of the present invention may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the polypeptide of the present invention also comprise a glucoamylase (AMG), and an alpha-amylase.

Further, the polypeptide of the present invention is particularly useful in the production of sweeteners and ethanol (see, e.g., U.S. Pat. No. 5,231,017, which is hereby incorporated by reference), such as fuel, drinking and industrial ethanol, from starch or whole grains. In one embodiment the present invention relates to a use of the polypeptide according to the invention for production of a syrup and/or a fermentation product from a starch containing material. The starch material may in one embodiment be gelatinized. In another embodiment the starch material is ungelatinized.

Starch Processing

Native starch consists of microscopic granules, which are insoluble in water at room temperature. When an aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art. Examples of alpha-amylase are disclosed in the "Alpha-Amylases" section below. Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question. The fermentation product may be recovered by methods well known in the art, e.g., by distillation. Examples of carbohydrate-source generating enzymes are disclosed in the "Enzymes" section below.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material. Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step. In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FAL1 (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermentation microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn.

Accordingly, in one aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. Saccharification and fermentation may also be separate. Thus in another aspect the invention relates to processes of producing fermentation products, comprising the following steps:
(i) saccharifying a starch-containing material at a temperature below the initial gelatinization temperature; and
(ii) fermenting using a fermentation organism;
wherein step (i) is carried out using at least a glucoamylase, and a variant pullulanase according to the invention.

In one embodiment, an alpha amylase is added in step (i). In another embodiment steps (i) and
(ii) are performed simultaneously.

In one embodiment, a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:
(a) liquefying starch-containing material in the presence of an alpha-amylase; or
(b) saccharifying the liquefied material obtained in step (a) using a glucoamylase;
(c) fermenting using a fermenting organism;
wherein step (a) and/or step (b) is carried out in the presence of a pullulanase according to the invention.

In an embodiment, a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a protease derived from a strain of *Pyrococcus*, more particularly from *Pyrococcus furiosus* disclosed in U.S. Pat. No. 6,358,726. In an embodiment the glucoamylase derived from a strain of *Aspergillus*, e.g., *Aspergillus niger* or *Aspergillus awamori*, a strain of *Talaromyces*, especially *Talaromyces emersonii*; or a strain of Athelia, especially Athelia *rolfsii*; a strain of *Trametes*, e.g., *Trametes cingulata*; a strain of the genus *Gloeophyllum*, e.g., a strain of *Gloeophyllum sepiarum* or *Gloeophyllum trabeum*; or a mixture thereof. Saccharification step (b) and fermentation step (c) may be carried out either sequentially or simultaneously. A pullulanase and/or metalloprotease may be added during saccharification and/or fermentation when the process is carried out as a sequential saccharification and fermentation process and before or during fermentation when steps (b) and (c) are carried out simultaneously (SSF process). The pullulanase and/or metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:
x) reducing the particle size of the starch-containing material, preferably by milling (e.g., using a hammer mill);
y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an preferred embodiment the fermentation product is ethanol.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hours, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch may be further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), *Thermoanarobacter ethanolicus, Thermoanaerobacter mathranii*, or *Thermoanaerobacter thermosaccharolyticum*. Strains of *Lactobacillus* are also envisioned as are strains of *Corynebacterium glutamicum* R, *Bacillus thermoglucosidaisus*, and *Geobacillus thermoglucosidasius*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

In one embodiment, the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

In an embodiment, the C5 utilizing yeast is a *Saccharomyces cerevisea* strain disclosed in WO 2004/085627.

In an embodiment, the fermenting organism is a C5 eukaryotic microbial cell concerned in WO 2010/074577 (Nedalco).

In an embodiment, the fermenting organism is a transformed C5 eukaryotic cell capable of directly isomerize xylose to xylose disclosed in US 2008/0014620.

In an embodiment, the fermenting organism is a C5 sugar fermentating cell disclosed in WO 2009/109633.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

The fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Compositions

The present invention also relates to compositions comprising a hybrid pullulanase according to the invention and at least one additional enzyme. The additional enzyme(s) may be selected from the group consisting of an alpha amylase, glucoamylase, beta-amylase, cellulase (beta-glucosidase, cellobiohydrolase and endoglucanase), hemicellulase (e.g., xylanase), isoamylase, isomerase, lipase, phytase, protease, a further pullulanase, and/or other enzymes useful in a commercial process in conjunction with a pullulanase. Such enzymes are known in the art in starch processing, sugar conversion, fermentations for alcohol and other useful end-products, commercial detergents and cleaning aids, stain removal, fabric treatment or desizing, and the like.

The enzyme composition of the present invention may be in any form suitable for use, such as, for example, a crude fermentation broth with or without cells removed, a cell lysate with or without cellular debris, a semi-purified or purified enzyme composition, or a host cell, e.g., Trichoderma host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Enzymes

The enzyme(s) and polypeptides described below are to be used in an "effective amount" in processes of the present invention.

Alpha-Amylases

Any alpha-amylase may be used, such as of fungal, bacterial or plant origin. In a preferred embodiment the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

An alpha-amylase for use in the present invention may be a bacterial alpha-amylase, e.g., derived from Bacillus. In a preferred embodiment the Bacillus alpha-amylase is derived from a strain of Bacillus amyloliquefaciens, Bacillus licheniformis, Bacillus stearothermophilus, or Bacillus subtilis, but may also be derived from other Bacillus sp.

Specific examples of alpha-amylases include the Bacillus amyloliquefaciens alpha-amylase of SEQ ID NO: 5 in WO 99/19467, the Bacillus licheniformis alpha-amylase of SEQ ID NO: 4 in WO 99/19467, and the Bacillus stearothermophilus alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

The Bacillus alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include Bacillus stearothermophilus alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta (181-182) compared to the amino acid sequence of Bacillus stearothermophilus alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). Even more preferred are Bacillus alpha-amylases, especially Bacillus stearothermophilus alpha-amylases, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467. The bacterial alpha-amylase may also have a substitution in a position corresponding to S239 in the Bacillus licheniformis alpha-amylase shown in SEQ ID NO: 4 in WO 99/19467, or a S242 variant of the Bacillus stearothermophilus alpha-amylase of SEQ ID NO: 3 in WO 99/19467. In a preferred embodiment the alpha-amylase is selected from the group of Bacillus stearomthermphilus alpha-amylase variants:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V; and

I181*+G182*+N193F+E129V+K177L+R179E+K220P+ N224L+S242Q+Q254S (using SEQ ID NO: 3 disclosed in WO 99/19467 for numbering).

Bacterial Hybrid Alpha-Amylases

The alpha-amylase may be a hybrid alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions: G48A+T49I+G107A+H156Y+A181T+ N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

Fungal Alpha-Amylases

Fungal alpha-amylases include alpha-amylases derived from a strain of *Aspergillus*, such as, *Aspergillus kawachii, Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/TeEMBL database under the primary accession no. P56271 and described in WO 89/01969 (Example 3—incorporated by reference).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In a preferred embodiment, the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus* kawachii"; and further as EMBL: # AB008370).

The fungal alpha-amylase may also be a wild-type enzyme comprising a starch-binding domain (SBD) and an alpha-amylase catalytic domain, or a variant thereof.

Fungal Hybrid Alpha-Amylases

In a preferred embodiment, the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/069290), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

In a preferred embodiment the alpha-amylase is an alpha-amylase derived from *Rhizomucor pusillus* with an *Aspergillus niger* glucoamylase linker and starch-binding domain (SBD), preferably the one shown in SEQ ID NO: 7 in WO2013/006756, preferably having one or more of the following substitutions: G128D, D143N, especially G128D+D143N.

Other examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

Commercial Alpha-Amylase Products

Preferred commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEXLO™, SPEZYME™ FRED, SPEZYME™ AA, SPEZYME™ ALPHA, SPEZYME™ DELTA AA, GC358, GC980, SPEZYME™ CL and SPEZYME™ RSL (DuPont Industrial Biosciences), and the acid fungal alpha-amylase from *Aspergillus niger* referred to as SP288 (available from Novozymes A/S, Denmark).

Carbohydrate-Source Generating Enzymes (Saccharifying Enzymes)

The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. A mixture of carbohydrate-source generating enzymes may be used. Blends include mixtures comprising at least a glucoamylase and an alpha-amylase, especially an acid amylase, even more preferred an acid fungal alpha-amylase.

In a conventional starch-to-ethanol process (i.e., including a liquefaction step), the ratio may preferably be as defined in EP 140410, especially when saccharification and fermentation are carried out simultaneously.

Glucoamylases

The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

A glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Prot. Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces* duponti, *Talaromyces emersonii* (WO 99/28448), *Talaromyces leycettanus* (U.S. Pat. No. Re. 32,153), and *Talaromyces thermophilus* (U.S. Pat. No. 4,587,215). *Gloeophyllum* sp. (US 2012/0214196).

In a specific embodiment the glucoamylase is from a strain of the genus *Penicillium*, especially a strain of *Penicillium oxalicum*, in particular the *Penicillium oxalicum* glucoamylase disclosed as SEQ ID NO: 2 in WO 2011/127802. In a preferred embodiment the glucoamylase is a variant of the *Penicillium oxalicum* glucoamylase disclosed as SEQ ID NO: 2 in WO 2011/127802 having a K79V substitution using the mature polypeptide (amino acids 22-616 of SEQ ID NO: 2) for numbering, and described in WO 2013/036526. In a preferred embodiment the glucoamylase is a variant of the *Penicillium oxalicum* glucoamylase disclosed as amino acids 22-616 of SEQ ID NO: 2 in WO 2011/127802 having a K79V substitution and one or more of the following substitutions P2N, P4S, P11F, T65A, Q327F, especially P2N+P4S+P11F+T65A+Q327F as described in WO2013/053801.

In a specific embodiment the glucoamylase is from a strain of the genus *Pycnoporus*, especially a strain of *Pycnoporus sanguineus*, in particular the *Pycnoporus sanguineus* glucoamylase disclosed as SEQ ID NO: 2, 4, or 6 in WO 2011/066576. In a preferred embodiment the enzyme composition comprises the glucoamylase shown as amino acids 19-573 of SEQ ID NO: 6 in WO 2011/066576.

In a specific embodiment the glucoamylase is from a strain of the genus *Gloeophillum*, especially a strain of *Gloeophyllum trabeum*, in particular the *Gloeophyllum trabeum* glucoamylase disclosed as SEQ ID NO: 18 in WO 2011/068803. In an especially preferred embodiment the enzyme composition comprises the *Gloeophyllum trabeum* glucoamylase shown in amino acids 18-576 of SEQ ID NO: 18 in WO2011/068803, and having one or more of the following substitutions: S95P, A121P, especially S95P+A121P using the mature polypeptide (positions 18-576 of SEQ ID NO: 18) for numbering.

In a specific embodiment the glucoamylase is from a strain of the genus *Gloeophillum*, especially a strain of *Gloeophillum sepiarium*, in particular the mature *Gloeophillum sepiarium* glucoamylase disclosed as amino acids 18-573 of SEQ ID NO: 2 in WO2011/068803.

Bacterial glucoamylases include glucoamylases from *Clostridium*, in particular *C. thermoamylolyticum* (EP 135138) and *C. thermohydrosulfuricum* (WO 86/01831), *Trametes cingulata*, *Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes A/S, Denmark); OPTIDEX™ 300, GC480™ and GC147™ (from DuPont Industrial Biosciences, USA); AMIGASE™ and AMIGASE™ PLUS (from DSM); G-ZYME™ G900, G-ZYME™ and G990 ZR (from DuPont Industrial Biosciences).

Glucoamylases may be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from DuPont Industrial Biosciences, USA.

Maltogenic Amylases

The amylase may also be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may be added in an amount of 0.05-5 mg total protein/gram DS or 0.05-5 MANU/g DS.

Pullulanases

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

The pullulanase according to the invention, and in addition any further pullulanase may be added, preferably a bacterial pullulanase, preferably derived from a strain of the genus Bacillus, especially derived from a strain of Bacillus deramificans, Bacillus subtilis, Bacillus amyloderamificans, or Bacillus acidopullulyticus.

The pullulanase may according to the invention be added in an effective amount which include the preferred range of from between 1-100 micro g per g DS, especially from 10-60 micro g per g DS. Pullulanase activity may be determined as NPUN. An Assay for determination of NPUN is described in the "Materials & Methods"-section below.

In a preferred embodiment, the pullulanase is used in an amount between 1-100 micro g enzyme protein per g DS, preferably between 10-60 micro g enzyme protein per g DS.

Suitable commercially available pullulanase products include PROMOZYME D, PROMOZYME™ D2 (Novozymes A/S, Denmark), OPTIMAX L-1000, OPTIMAX L-300 (DuPont Industrial Biosciences), and AMANO 8 (Amano, Japan).

The present invention is further described by the following numbered embodiments:

Embodiment 1

A pullulanase variant comprising a substitution at one or more positions corresponding to positions 393, 143, 150, 243, 244, 346, 368, 370, 373, 381, 385, 387, 402, 429, 430, 456, 486, 492, 610, 631, 632, 665 and 699 of the polypeptide of SEQ ID NO: 3 wherein the variant has pullulanase activity; and
a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or
b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 2

The pullulanase variant according to embodiment 1, comprising a substitution at two or more positions corresponding to positions 393, 143, 150, 243, 244, 346, 368, 370, 373, 381, 385, 387, 402, 429, 430, 456, 486, 492, 610, 624, 631, 632, 665 and 699 of the polypeptide of SEQ ID NO: 3 wherein the variant has pullulanase activity; and;
a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or
b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 3

The pullulanase variant according to embodiment 1, comprising a substitution at three or more positions corresponding to positions 393, 143, 150, 243, 244, 346, 368, 370, 373, 381, 385, 387, 402, 429, 430, 431, 456, 486, 492, 610, 624, 631, 632, 665 and 699 of the polypeptide of SEQ ID NO: 3 wherein the variant has pullulanase activity; and;
a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or
b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 4

The pullulanase variant according to embodiment 1, comprising a substitution at four or more positions corresponding to positions 393, 143, 150, 243, 244, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant has pullulanase activity; and;
a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or
b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or
d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 5

The pullulanase variant according to embodiment 1, comprising a substitution at five or more positions corresponding to positions 393, 143, 150, 243, 244, 345, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant has pullulanase activity; and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 6

The pullulanase variant according to embodiment 1, comprising a substitution at six or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3 wherein the variant has pullulanase activity; and;

a) wherein the variant has at least 85%, at least 90%, at least 95%, at least 96%, at least 97%, at least 98%, or at least 99%, but less than 100% sequence identity to the polypeptide of SEQ ID NO: 3 and wherein the variant has increased thermoactivity compared to the pullulanase of SEQ ID NO: 3, particularly the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%; or b) wherein the variant has at least 85%, at least 90%, at least 95%, at least 96%, at least 97%, at least 98%, or at least 99%, but less than 100% sequence identity to the polypeptide of SEQ ID NO: 6 and wherein the variant has increased thermoactivity compared to the pullulanase of SEQ ID NO: 6, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or c) wherein the variant has at least 85%, at least 90%, at least 95%, at least 96%, at least 97%, at least 98%, or at least 99%, but less than 100% sequence identity to the polypeptide of SEQ ID NO: 9 and wherein the variant has increased thermoactivity compared to the pullulanase of SEQ ID NO: 9, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or d) wherein the variant has at least 85%, at least 90%, at least 95%, at least 96%, at least 97%, at least 98%, or at least 99%, but less than 100% sequence identity to the polypeptide of SEQ ID NO: 16 and wherein the variant has increased thermoactivity compared to the pullulanase of SEQ ID NO: 16, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%; or e) wherein the variant has at least 85%, at least 90%, at least 95%, at least 96%, at least 97%, at least 98%, or at least 99%, but less than 100% sequence identity to the polypeptide of SEQ ID NO: 17 and wherein the variant has increased thermoactivity compared to the pullulanase of SEQ ID NO: 17, particularly the variant has at least 30% relative activity when measured at 70° C. relative to activity at 65° C., more particularly at least 40%, more particularly at least 50%, more particularly at least 60%, more particularly at least 70%, more particularly at least 80%, more particularly at least 90%, more particularly at least 100%.

Embodiment 7

The pullulanase variant according to any of the preceding embodiments, comprising a substitution at one position corresponding to positions 393, 143, 150, 243, 244, 345, 346, 368, 486, 492, 610, 624, or 699 of the polypeptide of SEQ ID NO: 3 wherein the variant has pullulanase activity.

Embodiment 8

The variant of any of embodiments 1-7, wherein the number of substitutions is 1-20, e.g., 1-10 and 1-5, such as 1, 2, 3, 4, 5, 6, 7, 8, 9 or 10 substitutions.

Embodiment 9

The variant of any of embodiments 1-8, which comprises a substitution at a position corresponding to position 393.

Embodiment 10

The variant of embodiment 09, wherein the substitution is with Alanine.

Embodiment 11

The variant of any of embodiments 1-8, which comprises a substitution at a position corresponding to position 143.

Embodiment 12

The variant of embodiment 11, wherein the substitution is with Valine.

Embodiment 13

The variant of any of embodiments 1-8, which comprises a substitution at a position corresponding to position 150.

Embodiment 14

The variant of embodiment 13, wherein the substitution is with Arginine.

Embodiment 15

The variant of any of embodiments 1-8, which comprises a substitution at a position corresponding to position 243.

Embodiment 16

The variant of embodiment 15, wherein the substitution is with Glutamic Acid.

Embodiment 17

The variant of any of embodiments 1-8, which comprises a substitution at a position corresponding to position 244.

Embodiment 18

The variant of embodiment 17, wherein the substitution is with Lysine.

Embodiment 19

The variant of any of embodiments 1-8, which comprises a substitution at a position corresponding to position 345.

Embodiment 20

The variant of embodiment 19, wherein the substitution is with Proline.

Embodiment 21

The variant of any of embodiments 1-8, which comprises a substitution at a position corresponding to position 346.

Embodiment 22

The variant of embodiment 21, wherein the substitution is with Serine.

Embodiment 23

The variant of any of embodiments 1-8, which comprises a substitution at a position corresponding to position 368.

Embodiment 24

The variant of embodiment 23, wherein the substitution is with Glutamic Acid.

Embodiment 25

The variant of any of embodiments 1-8, which comprises a substitution at a position corresponding to position 370.

Embodiment 26

The variant of embodiment 25, wherein the substitution is with Serine.

Embodiment 27

The variant of any of embodiments 1-8, which comprises a substitution at a position corresponding to position 373.

Embodiment 28

The variant of embodiment 27, wherein the substitution is with Leucine.

Embodiment 29

The variant of any of embodiments 1-8, which comprises a substitution at a position corresponding to position 381.

Embodiment 30

The variant of embodiment 29, wherein the substitution is with Valine.

Embodiment 31

The variant of any of embodiments 1-8, which comprises a substitution at a position corresponding to position 382.

Embodiment 32

The variant of embodiment 31, wherein the substitution is with Threonine.

Embodiment 33

The variant of any of embodiments 1-8, which comprises a substitution at a position corresponding to position 385.

Embodiment 34

The variant of embodiment 33, wherein the substitution is with Glutamic Acid.

Embodiment 35

The variant of any of embodiments 1-8, which comprises a substitution at a position corresponding to position 402.

Embodiment 36

The variant of embodiment 35, wherein the substitution is with Threonine.

Embodiment 37

The variant of any of embodiments 1-8, which comprises a substitution at a position corresponding to position 429.

Embodiment 38

The variant of embodiment 37, wherein the substitution is with Valine.

Embodiment 39

The variant of any of embodiments 1-8, which comprises a substitution at a position corresponding to position 430.

Embodiment 40

The variant of embodiment 39, wherein the substitution is with Arginine.

Embodiment 41

The variant of any of embodiments 1-8, which comprises a substitution at a position corresponding to position 431.

Embodiment 42

The variant of embodiment 41, wherein the substitution is with Glutamic Acid.

Embodiment 43

The variant of any of embodiments 1-8, which comprises a substitution at a position corresponding to position 432.

Embodiment 44

The variant of embodiment 43, wherein the substitution is with Phenylalanine.

Embodiment 45

The variant of any of embodiments 1-8, which comprises a substitution at a position corresponding to position 456.

Embodiment 46

The variant of embodiment 45, wherein the substitution is with Alanine.

Embodiment 47

The variant of any of embodiments 1-8, which comprises a substitution at a position corresponding to position 486.

Embodiment 48

The variant of embodiment 47, wherein the substitution is with Cysteine.

Embodiment 49

The variant of any of embodiments 1-8, which comprises a substitution at a position corresponding to position 492.

Embodiment 50

The variant of embodiment 49, wherein the substitution is with Serine or Alanine.

Embodiment 51

The variant of any of embodiments 1-8, which comprises a substitution at a position corresponding to position 610.

Embodiment 52

The variant of embodiment 51 wherein the substitution is with Leucine or Arginine.

Embodiment 53

The variant of any of embodiments 1-8, which comprises a substitution at a position corresponding to position 624.

Embodiment 54

The variant of embodiment 53, wherein the substitution is with Serine.

Embodiment 55

The variant of any of embodiments 1-8, which comprises a substitution at a position corresponding to position 631.

Embodiment 56

The variant of embodiment 55 wherein the substitution is with Serine.

Embodiment 57

The variant of any of embodiments 1-8, which comprises a substitution at a position corresponding to position 632.

Embodiment 58

The variant of embodiment 57 wherein the substitution is with Cysteine.

Embodiment 59

The variant of any of embodiments 1-8, which comprises a substitution at a position corresponding to position 665.

Embodiment 60

The variant of embodiment 59 wherein the substitution is with Isoleucine.

Embodiment 61

The variant of any of embodiments 1-8, which comprises a substitution at a position corresponding to position 699.

Embodiment 62

The variant of embodiment 61 wherein the substitution is with Arginine.

Embodiment 63

The variant according to embodiment 1-62, wherein the variant comprises or consists of one or more substitutions selected from the group consisting of 393A, 143G, 150R, 243E, 244K, 345P, 346S, 368G, 370S, 373L, 381V, 382T, 385F, 387L, 402T, 429V, 430R, 431E, 432F, 456A, 486C, 492S, 610R,L, 624S, 631S, 632C, 665I and 699R.

The variant of any of the preceding embodiments, wherein the variant comprises at least one of the following substitutions or combinations of substitutions:
N368G;
E699R;
E150R;
N346S;
N243E;
S244K;
V143G;
N393A;
N610R;
N610L;
G624S;
F456A;
T492S;
V486C+T492S;
N368G+M402T;
T631S+S632C;
V486C+T492S+T631S+S632C;
N393A+T631S+S632C;
T631S+S632C+E699R;
N393A+V486C+T492S+T631S+S632C;
N393A+G624S+S632C;
N393A+N610R+T631S+S632C;
N393A+G624S+T631S+S632C;
N393A+N610R+G624S+T631S+S632C;
N393A+V486C+T492S+G624S+T631S+S632C;
N393A+V486C+T492S+N610R+G624S+T631S+S632C;
N368G+N393A+V486C+T492S+N610R+G624S+T631S+S632C;
N393A+V486C+T492S+N610R+G624S+T631S+S632C+E699R;
N346S+N393A+V486C+T492S+N610R+G624S+T631S+S632C;
N393A+F456A+V486C+T492S+N610R+G624S+T631S+S632C;
N393A+T492S+N610R+G624S+T631S+S632C;
N368G+N393A+T492S+N610R+G624S+T631S+S632C;
A345P+N393A+V486C+T492S+N610R+G624S+T631S+S632C;
N368G+K370S+I373L+N393A+V486C+T492S+N610R+G624S+T631S+S632C;
I381V+Q385E+Q387L+N393A+V486C+T492S+N610R+G624S+T631S+S632C;
I381V+N382T+Q385E+Q387L+N393A+V486C+T492S+N610R+G624S+T631S+S632C;
A345P+N368G+N393A+T492S+N610R+G624S+T631S+S632C;
N368G+I381V+Q385E+Q387L+N393A+T492S+N610R+G624S+T631S+S632C;
A345P+N368G+I381V+Q385E+Q387L+N393A+T492S+N610R+G624S+T631S+S632C;
A345P+N368G+I381V+Q385E+Q387L+N393A+T492S+N610R+G624S+T631S+S632C+V665I;
N393A+T430R+Q431E+L432F+V486C+T492S+N610R+G624S+T631S+S632C;
N393A+Q431E+L432F+V486C+T492S+N610R+G624S+T631S+S632C;
N393A+I429V+Q431E+V486C+T492S+N610R+G624S+T631S+S632C;
N393A+I429V+T430R+Q431E+L432F+V486C+T492S+N610R+G624S+T631S+S632C;
N368G+N393A+A492S,A;
N368G+N393A;
N393A+N610R;
N368G+N393A+N610R;
N368G+N393A+T492S,A+N610R+G624S;
N368G+N393A+T492S,A+N610R+G624S+T631S+S632C+Q431E+L432F;
N368G+N393A+N610R+G624S+T631S+S632C;
N368G+N393A+T492S,A+N610R+G624S+T631S+S632C;
N368G+N393A+N610R+G624S+T631S+S632C+Q431E+L432F.

Embodiment 64

A variant catalytic domain, wherein the variant catalytic domain comprises a substitution at one or more positions corresponding to positions 393, 346, 368, 370, 373, 381, 385, 387, 402, 429, 430, 456, 486, 492, 610, 631, 632, 665 and 699 of the polypeptide of SEQ ID NO: 3; and;
a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or
b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or c) wherein the variant catalytic domain has at least 85%, at least 90%, at least 95%, at least 96%, at least 97%, at least 98%, or at least 99%, but less than 100% sequence identity to the polypeptide of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 65

The variant catalytic domain according to embodiment 64 comprising a substitution at two or more positions corresponding to positions 393, 346, 368, 370, 373, 381, 385, 387, 402, 429, 430, 456, 486, 492, 610, 624, 631, 632, 665 and 699 of the polypeptide of SEQ ID NO: 3 wherein the variant catalytic domain has pullulanase activity, and;
a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or
b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or
c) wherein the variant catalytic domain has at least 85%, at least 90%, at least 95%, at least 96%, at least 97%, at least 98%, or at least 99%, but less than 100% sequence identity to the polypeptide of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 66

The variant catalytic domain according to embodiment 64 comprising a substitution at three or more positions corresponding to positions 393, 346, 368, 370, 373, 381, 385, 387, 402, 429, 430, 431, 456, 486, 492, 610, 624, 631, 632, 665 and 699 of the polypeptide of SEQ ID NO: 3 wherein the variant catalytic domain has pullulanase activity, and;
a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or
b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or
c) wherein the variant catalytic domain has at least 85%, at least 90%, at least 95%, at least 96%, at least 97%, at least 98%, or at least 99%, but less than 100% sequence identity to the polypeptide of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 67

The variant catalytic domain according to embodiment 64 comprising a substitution at four or more positions corresponding to positions 393, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant catalytic domain has pullulanase activity, and;
a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or
b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or
c) wherein the variant catalytic domain has at least 85%, at least 90%, at least 95%, at least 96%, at least 97%, at least 98%, or at least 99%, but less than 100% sequence identity to the polypeptide of SEQ ID NO: 9, or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 68

The variant catalytic domain according to embodiment 64 comprising a substitution at five or more positions corresponding to positions 393, 345, 346, 368, 370, 373, 381, 385, 387, 402, 429, 430, 431, 432, 456, 486, 492, 610, 624, 631, 632, 665 and 699 of the polypeptide of SEQ ID NO: 3 wherein the variant catalytic domain has pullulanase activity; and;
a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or
b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or
c) wherein the variant catalytic domain has at least 85%, at least 90%, at least 95%, at least 96%, at least 97%, at least 98%, or at least 99%, but less than 100% sequence identity to the polypeptide of SEQ ID NO: 9; or
d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or
e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 69

The variant catalytic domain according to embodiment 64 comprising a substitution at six or more positions corresponding to positions 393, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3 wherein the variant catalytic domain has pullulanase activity; and;

a) wherein the variant catalytic domain has at least 85%, at least 90%, at least 95%, at least 96%, at least 97%, at least 98%, or at least 99%, but less than 100% sequence identity to the polypeptide of SEQ ID NO: 3; or b) wherein the variant catalytic domain has at least 85%, at least 90%, at least 95%, at least 96%, at least 97%, at least 98%, or at least 99%, but less than 100% sequence identity to the polypeptide of SEQ ID NO: 6; or c) wherein the variant catalytic domain has at least 85%, at least 90%, at least 95%, at least 96%, at least 97%, at least 98%, or at least 99%, but less than 100% sequence identity to the polypeptide of SEQ ID NO: 9; or d) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 16; or e) wherein the variant catalytic domain has at least 85%, at least 90%, at least 95%, at least 96%, at least 97%, at least 98%, or at least 99%, but less than 100% sequence identity to amino acids 430 to 928 of SEQ ID NO: 17.

Embodiment 70

A pullulanase variant comprising the variant catalytic domain according to any of embodiments 64 to 69, wherein the pullulanase variant has pullulanase activity and increased thermoactivity compared to the parent pullulanase, and the variant has at least 60% relative activity when measured at 70° C. relative to activity at 65° C., more particularly at least 65%, more particularly at least 70%, more particularly at least 60%, more particularly at least 75%, more particularly at least 80%, more particularly at least 90%, more particularly at least 100%.

Embodiment 71

The pullulanase variant according to embodiment 70, wherein the variant comprises or consists of one or more substitutions selected from the group consisting of 393A, 143G, 150R, 243E, 244K, 345P, 346S, 368G, 370S, 373L, 381V, 382T, 385F, 387L, 402T, 429V, 430R, 431E, 432F, 456A, 486C, 492S, 610R,L, 624S, 631S, 632C, 665I and 699R.

Embodiment 72

The pullulanase variant according to any of embodiments 64-71, further comprising an N-terminal part comprising at least one of the domains selected from a CBM41 domain, an X45 domain and a CBM48 domain.

Embodiment 73

The pullulanase variant according to embodiment 72, comprising an N-terminal part comprising a CBM41 domain, an X45 domain and a CBM48 domain.

Embodiment 74

The pullulanase variant according to embodiment 72-73, further comprising a X25 domain.

Embodiment 75

The pullulanase variant according to any of embodiments 64-74, wherein the variant comprises one or more substitutions selected from the group consisting of 393A, 368G, 486C, 492S,A, 610R,L, 624S, 631S, 632C, 431E, 432F.

Embodiment 76

The pullulanase variant according to embodiment 75, wherein the variant comprises at least one of the following substitutions or combinations of substitutions:
368G+393A+492S,A;
368G+393A+492A,S+610R+624S;
393A+492S,A+610R+624S+631 S+632C;
368G+393A+492S,A+610R+624S+631S+632C;
368G+393A+492S,A+610R+624S+631 S+632C+431E+432F;
368G+393A+610R+624S+631 S+632C; or
368G+393A+610R+624S+631S+632C+431E+432F.

Embodiment 77

The pullulanase variant according to any of embodiments 1-76, selected from SEQ ID NO: 20 or a pullulanase having at least 85%, at least 90%, at least 95%, at least 96%, at least 97%, at least 98%, or at least 99%, or 100% sequence identity to the polypeptide of SEQ ID NO: 20; SEQ ID NO: 21 or a pullulanase having at least 85%, at least 90%, at least 95%, at least 96%, at least 97%, at least 98%, or at least 99%, or 100% sequence identity to the polypeptide of SEQ ID NO: 21; SEQ ID NO: 22 or a pullulanase having at least 85%, at least 90%, at least 95%, at least 96%, at least 97%, at least 98%, or at least 99%, or 100% sequence identity to the polypeptide of SEQ ID NO: 22; SEQ ID NO: 23 or a pullulanase having at least 85%, at least 90%, at least 95%, at least 96%, at least 97%, at least 98%, or at least 99%, or 100% sequence identity to the polypeptide of SEQ ID NO: 23; SEQ ID NO: 24 or a pullulanase having at least 85%, at least 90%, at least 95%, at least 96%, at least 97%, at least 98%, or at least 99%, or 100% sequence identity to the polypeptide of SEQ ID NO: 24; SEQ ID NO: 25 or a pullulanase having at least 85%, at least 90%, at least 95%, at least 96%, at least 97%, at least 98%, or at least 99%, or 100% sequence identity to the polypeptide of SEQ ID NO: 25; SEQ ID NO: 26 or a pullulanase having at least 85%, at least 90%, at least 95%, at least 96%, at least 97%, at least 98%, or at least 99%, or 100% sequence identity to the polypeptide of SEQ ID NO: 26; SEQ ID NO: 27 or a pullulanase having at least 85%, at least 90%, at least 95%, at least 96%, at least 97%, at least 98%, or at least 99%, or 100% sequence identity to the polypeptide of SEQ ID NO: 27; SEQ ID NO: 28 or a pullulanase having at least 85%, at least 90%, at least 95%, at least 96%, at least 97%, at least 98%, or at least 99%, or 100% sequence identity to the polypeptide of SEQ ID NO: 28.

Embodiment 78

The variants according to embodiments 1-77, which have an improved property relative to the parent, wherein the improved property is increased thermoactivity.

Embodiment 79

The variant according to embodiments 1-78, wherein the variant has increased specific activity toward starch or maltodextrin compared to any of SEQ ID NO: 3, SEQ ID NO:6, SEQ ID NO:9, SEQ ID NO:16, or SEQ ID NO:17.

Embodiment 80

The variants according to embodiment 79, wherein the variant is selected from SEQ ID NO: 20 or a pullulanase having at least 85%, at least 90%, at least 95%, at least 96%, at least 97%, at least 98%, or at least 99%, or 100% sequence identity to the polypeptide of SEQ ID NO: 20; SEQ ID NO: 21 or a pullulanase having at least 85%, at least 90%, at least 95%, at least 96%, at least 97%, at least 98%, or at least 99%, or 100% sequence identity to the polypeptide of SEQ ID NO: 21; SEQ ID NO: 22 or a pullulanase having at least 85%, at least 90%, at least 95%, at least 96%, at least 97%, at least 98%, or at least 99%, or 100% sequence identity to the polypeptide of SEQ ID NO: 22. SEQ ID NO: 23 or a pullulanase having at least 85%, at least 90%, at least 95%, at least 96%, at least 97%, at least 98%, or at least 99%, or 100% sequence identity to the polypeptide of SEQ ID NO: 23; SEQ ID NO: 25 or a pullulanase having at least 85%, at least 90%, at least 95%, at least 96%, at least 97%, at least 98%, or at least 99%, or 100% sequence identity to the polypeptide of SEQ ID NO: 25; SEQ ID NO: 26 or a pullulanase having at least 85%, at least 90%, at least 95%, at least 96%, at least 97%, at least 98%, or at least 99%, or 100% sequence identity to the polypeptide of SEQ ID NO: 26; SEQ ID NO: 27 or a pullulanase having at least 85%, at least 90%, at least 95%, at least 96%, at least 97%, at least 98%, or at least 99%, or 100% sequence identity to the polypeptide of SEQ ID NO: 27. SEQ ID NO: 28 or a pullulanase having at least 85%, at least 90%, at least 95%, at least 96%, at least 97%, at least 98%, or at least 99%, or 100% sequence identity to the polypeptide of SEQ ID NO: 28.

Embodiment 81

The variants according to any of the preceding embodiments, wherein the varaints further comprises one of the following substitutions or combinations of substitutions (using SEQ ID NO: 6 for numbering):
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+Q356R;
Y27K+H79Y+H186A+V212I+Q258A+Q287R+N322P+Q352A+Q356R;
Y27K+H79Y+H186A+V212I+Q258A+Q287R+N322P+Q352A+Q356R+D686S;
N19G+Y27K+H79Y+H186A+V212I+Q258A+Q287R+N322P+Q352A+Q356R+D686S;
N19G+Y27K+H79Y+H186A+V212I+Q258A+Q287R+G296R+N322P+Q352A+Q356R+D686S;
Y27K+H79Y+H186A+V212I+Q258A+Q287R+N322P+Q352A+Q356R+V586A+D686S;
Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+V586A+D686S;
N19G+Y27K+H79Y+H186A+V212I+Q258A+Q287R+N322P+Q352A+Q356R+D686S+E799R;
N19G+Y27K+H79Y+H186A+V212I+Q258A+Q287R+N322P+Q352A+Q356R+Q485E+D686S+E799R;
N19G+Y27K+H79Y+H186A+V212I+Q258A+Q287R+N322P+Q352A+Q356R+Q487L+D686S+E799R;
N19G+Y27K+H79Y+H186A+V212I+Q258A+Q287R+N322P+Q352A+Q356R+V586A+D686S+E799R;
N19G+Y27K+H79Y+H186A+V212I+Q258A+Q287R+G296R+N322P+Q352A+Q356R+V586A+D686S+E799R;
N19G+Y27K+H79Y+H186A+V212I+Q258A+Q287R+G296R+N322P+Q352A+Q356R+Q487L+V586A+D686S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+D686S+C732S+E799R;
N19G+Y27K+H79Y+H186A+V212I+Q258A+Q287R+N322P+Q352A+Q356R+Q487L+S557A+L559G+D686S+E799R;
N19G+Y27K+H79Y+H186A+V212I+Q258A+Q287R+N322P+Q352A+Q356R+H421E+Q487L+S557A+L559G+V586A+D686S+E799R.

Embodiment 82

The variants according to claim 81, wherein the variants are selected from a pullulanase having at least 85%, at least 90%, at least 95%, at least 96%, at least 97%, at least 98%, or at least 99% sequence identity to the polypeptide of SEQ ID NO: 26, and comprising the substitutions (using SEQ ID NO: 6 for numbering): N468G+N493A+N710R+G724S+T731S+S732C+Q531E+L532F, and wherein the variants further comprises one of the following substitutions or combinations of substitutions:
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+Q356R;
Y27K+H79Y+H186A+V212I+Q258A+Q287R+N322P+Q352A+Q356R;
Y27K+H79Y+H186A+V212I+Q258A+Q287R+N322P+Q352A+Q356R+D686S;
N19G+Y27K+H79Y+H186A+V212I+Q258A+Q287R+N322P+Q352A+Q356R+D686S;
N19G+Y27K+H79Y+H186A+V212I+Q258A+Q287R+G296R+N322P+Q352A+Q356R+D686S;

Y27K+H79Y+H186A+V212I+Q258A+Q287R+N322P+
Q352A+Q356R+V586A+D686S;
Y27K+H79Y+H186A+V212I+Q258A+Q287R+N322P+
Q352A+Q356R+D686S+E799R;
N19G+Y27K+H79Y+H186A+V212I+Q258A+Q287R+
N322P+Q352A+Q356R+V586A+D686S;
N19G+Y27K+H79Y+H186A+V212I+Q258A+Q287R+
N322P+Q352A+Q356R+D686S+E799R;
N19G+Y27K+H79Y+H186A+V212I+Q258A+Q287R+
N322P+Q352A+Q356R+Q485E+D686S+E799R;
N19G+Y27K+H79Y+H186A+V212I+Q258A+Q287R+
N322P+Q352A+Q356R+Q487L+D686S+E799R;
N19G+Y27K+H79Y+H186A+V212I+Q258A+Q287R+
N322P+Q352A+Q356R+V586A+D686S+E799R;
N19G+Y27K+H79Y+H186A+V212I+Q258A+Q287R+
G296R+N322P+Q352A+Q356R+V586A+D686S+E799R;
N19G+Y27K+H79Y+H186A+V212I+Q258A+Q287R+
G296R+N322P+Q352A+Q356R+Q487L+V586A+D686S+
E799R;
N19G+Y27K+H79Y+H186A+V212I+Q258A+Q287R+
N322P+Q352A+Q356R+Q487L+D686S+C732S+E799R;
N19G+Y27K+H79Y+H186A+V212I+Q258A+Q287R+
N322P+Q352A+Q356R+Q487L+D686S+C732S+E799R;
N19G+Y27K+H79Y+H186A+V212I+Q258A+Q287R+
N322P+Q352A+Q356R+Q487L+S557A+L559G+D686S+
E799R;
N19G+Y27K+H79Y+H186A+V212I+Q258A+Q287R+
N322P+Q352A+Q356R+H421E+Q487L+S557A+L559G+
V586A+D686S+E799R; said variants having at least 60% relative activity when measured at 72° C. relative to activity at 65° C. using the PHADEBAS assay.

Embodiment 83

The variants according to embodiment 82, wherein the variants further comprises one of the following combinations of substitutions:
N19G+Y27K+H79Y+H186A+V212I+Q258A+Q287R+
N322P+Q352A+Q356R+Q487L+D686S+E799R.

Embodiment 84

The variants according to embodiment 81, wherein the variants are selected from a pullulanase having at least 85%, at least 90%, at least 95%, at least 96%, at least 97%, at least 98%, or at least 99% sequence identity to the polypeptide of SEQ ID NO: 27, and comprising the substitutions (using SEQ ID NO: 6 for numbering) N468G+N493A+T492S,A+
N710R+G724S+T731S+S732C+Q531E+L532F, and wherein the variants further comprises one of the following substitutions or combinations of substitutions:
Q258A;
Q287R;
Q352A;
Q356R;
Q258A+Q352A+Q356R;
Q258A+Q287R+Q352A+Q356R;
V212I;
H186A;
V212I+Q258A+Q287R+Q352A+Q356R;
H186A+V212I+Q258A+Q287R+Q352A+Q356R;
Y27K+H79Y+V212I+Q258A+Q287R+Q352A+Q356R;
Q258A+Q287R+N322P+Q352A+Q356R;
H186A+V212I+Q258A+Q287R+N322P+Q352A+Q356R;
H186A+V212I+Q258A+Q287R+Q352A+Q356R;
H186A+V212I+Q258A+Q287R+N322P+Q352A+Q356R;
Y27K+H79Y+H186A+V212I+Q258A+Q287R+Q352A+
Q356R;
Y27K+H79Y+H186A+V212I+Q258A+Q287R+N322P+
Q352A+Q356R;
Y27K+H79Y+H186A+V212I+Q258A+Q287R+N322P+
Q352A+Q356R+D686S;
N19G+Y27K+H79Y+H186A+V212I+Q258A+Q287R+
N322P+Q352A+Q356R+D686S;
N19G+Y27K+H79Y+H186A+V212I+Q258A+Q287R+
G296R+N322P+Q352A+Q356R+D686S;
Y27K+H79Y+H186A+V212I+Q258A+Q287R+N322P+
Q352A+Q356R+V586A+D686S;
Y27K+H79Y+H186A+V212I+Q258A+Q287R+N322P+
Q352A+Q356R+D686S+E799R;
N19G+Y27K+H79Y+H186A+V212I+Q258A+Q287R+
N322P+Q352A+Q356R+V586A+D686S;
N19G+Y27K+H79Y+H186A+V212I+Q258A+Q287R+
N322P+Q352A+Q356R+D686S+E799R;
N19G+Y27K+H79Y+H186A+V212I+Q258A+Q287R+
N322P+Q352A+Q356R+Q485E+D686S+E799R;
N19G+Y27K+H79Y+H186A+V212I+Q258A+Q287R+
N322P+Q352A+Q356R+Q487L+D686S+E799R;
N19G+Y27K+H79Y+H186A+V212I+Q258A+Q287R+
N322P+Q352A+Q356R+V586A+D686S+E799R;
N19G+Y27K+H79Y+H186A+V212I+Q258A+Q287R+
G296R+N322P+Q352A+Q356R+V586A+D686S+E799R;
N19G+Y27K+H79Y+H186A+V212I+Q258A+Q287R+
G296R+N322P+Q352A+Q356R+Q487L+V586A+D686S+
E799R;
N19G+Y27K+H79Y+H186A+V212I+Q258A+Q287R+
N322P+Q352A+Q356R+Q487L+D686S+C732S+E799R;
N19G+Y27K+H79Y+H186A+V212I+Q258A+Q287R+
N322P+Q352A+Q356R+Q487L+D686S+C732S+E799R;
N19G+Y27K+H79Y+H186A+V212I+Q258A+Q287R+
N322P+Q352A+Q356R+Q487L+S557A+L559G+D686S+
E799R;
N19G+Y27K+H79Y+H186A+V212I+Q258A+Q287R+
N322P+Q352A+Q356R+H421E+Q487L+S557A+L559G+
V586A+D686S+E799R; said variants having at least 60% relative activity when measured at 72° C. relative to activity at 65° C. using the PHADEBAS assay.

Embodiment 85

The variants according to claim 84, wherein the variants further comprise one of the following combinations of substitutions:
N19G+Y27K+H79Y+H186A+V212I+Q258A+Q287R+
N322P+Q352A+Q356R+Q487L+D686S+E799R.

Embodiment 86

The pullulanase variants according to any of the embodiments 1-80, wherein the variants further comprises one of the following substitutions or combinations of substitutions:
Y27K+H79Y+Q187R+S798R;
Y27K+H79Y+Q187R+D586S+S798R;
Y27K+H79Y+Q187R+D586S+E699R+S798R;
Y27K+H79Y+Q187R+T486S+D586S+S798R;
N19G+Y27K+H79Y+Q187R+T486C+D586S+E699R+
S798R;
N19G+Y27K+H79Y+Q187R+Q385E+T486C+D586S+
E699R+S798R;
N19G+Y27K+H79Y+Q187R+Q387L+T486C+D586S+
E699R+S798R;
N19G+Y27K+H79Y+Q187R+Q387L+Q459G+T486C+
D586S+C632S+E699R+S798R;

N19G+Y27K+H79Y+Q187R+Q387L+T486C+D586S+
C632S+Q675L+E699R+S798R;
N19G+Y27K+H79Y+Q187R+V196R+Q387L+T486C+
D586S+C632S+E699R+S798R;
N19G+Y27K+H79Y+Q187R+V196R+Q387L+T486C+
D586S+C632S+Q675L+E699R+S798R;
N19G+Y27K+H79Y+Q187R+V196R+Q387L+Q459G+
T486C+D586S+C632S+Q675L+E699R+S798R;
N19G+Y27K+H79Y+Q187R+Q387L+D586S+E699R+
S798R;
N19G+Y27K+H79Y+Q187R+H321E+Q387L+D586S+
E699R+S798R;
N19G+Y27K+H79Y+Q187R+Q387L+Q459G+D586S+
E699R+S798R;
N19G+Y27K+H79Y+Q187R+Q387L+D586S+C632S+
E699R+S798R;
N19G+Y27K+H79Y+Q187R+E310A+D311K+Q387L+
D586S+E699R+S798R;
N19G+Y27K+H79Y+Q187R+E310A+D311K+Q387L+
Q459G+D586S+E699R+S798R.

Embodiment 87

The variants according to claim 86, wherein the variants are selected from a pullulanase having at least 85%, at least 90%, at least 95%, at least 96%, at least 97%, at least 98%, or at least 99% sequence identity to the polypeptide of SEQ ID NO: 28, and comprising the substitutions N368G+N393A+T492S,A+N610R+G624S+T631 S+S632C+Q431E+L432F, and wherein the variants further comprises one of the following substitutions or combinations of substitutions:
Y27K+H79Y+Q187R+S798R;
Y27K+H79Y+Q187R+D586S+S798R;
Y27K+H79Y+Q187R+D586S+E699R+S798R;
Y27K+H79Y+Q187R+T486S+D586S+S798R;
N19G+Y27K+H79Y+Q187R+T486C+D586S+E699R+
S798R;
N19G+Y27K+H79Y+Q187R+Q385E+T486C+D586S+
E699R+S798R;
N19G+Y27K+H79Y+Q187R+Q387L+T486C+D586S+
E699R+S798R;
N19G+Y27K+H79Y+Q187R+Q387L+Q459G+T486C+
D586S+C632S+E699R+S798R;
N19G+Y27K+H79Y+Q187R+Q387L+T486C+D586S+
C632S+Q675L+E699R+S798R;
N19G+Y27K+H79Y+Q187R+V196R+Q387L+T486C+
D586S+C632S+E699R+S798R;
N19G+Y27K+H79Y+Q187R+V196R+Q387L+T486C+
D586S+C632S+Q675L+E699R+S798R;
N19G+Y27K+H79Y+Q187R+V196R+Q387L+Q459G+
T486C+D586S+C632S+Q675L+E699R+S798R;
N19G+Y27K+H79Y+Q187R+Q387L+D586S+E699R+
S798R;
N19G+Y27K+H79Y+Q187R+H321E+Q387L+D586S+
E699R+S798R;
N19G+Y27K+H79Y+Q187R+Q387L+Q459G+D586S+
E699R+S798R;
N19G+Y27K+H79Y+Q187R+Q387L+D586S+C632S+
E699R+S798R;
N19G+Y27K+H79Y+Q187R+E310A+D311K+Q387L+
D586S+E699R+S798R;
N19G+Y27K+H79Y+Q187R+E310A+D311K+Q387L+
Q459G+D586S+E699R+S798R, said variants having at least 30% relative activity when measured at 76° C. relative to activity at 65° C. using the PHADEBAS assay.

Embodiment 88

The variants according to embodiment 87, wherein the variants further comprises one of the following combinations of substitutions:
N19G+Y27K+H79Y+Q187R+E310A+D311K+Q387L+
D586S+E699R+S798R; or
N19G+Y27K+H79Y+Q187R+E310A+D311K+Q387L+
Q459G+D586S+E699R+S798R.

Embodiment 89

A method for producing a variant pullulanase of a parent pullulanase comprising substitution of the parent pullulanase at one or more positions corresponding to positions 393, 143, 150, 243, 244, 345, 346, 368, 370, 373, 381, 382, 385, 387, 402, 429, 430, 431, 432, 456, 486, 492, 610, 624, 631, 632, 665 and 699 of the polypeptide of SEQ ID NO: 3 wherein the variant has pullulanase activity; and;
a) wherein the variant has at least 85%, at least 90%, at least 95%, at least 96%, at least 97%, at least 98%, or at least 99%, but less than 100% sequence identity to the polypeptide of SEQ ID NO: 3; or
b) wherein the variant has at least 85%, at least 90%, at least 95%, at least 96%, at least 97%, at least 98%, or at least 99%, but less than 100% sequence identity to the polypeptide of SEQ ID NO: 6; or
c) wherein the variant has at least 85%, at least 90%, at least 95%, at least 96%, at least 97%, at least 98%, or at least 99%, but less than 100% sequence identity to the polypeptide of SEQ ID NO: 9; or
d) wherein the variant has at least 85%, at least 90%, at least 95%, at least 96%, at least 97%, at least 98%, or at least 99%, but less than 100% sequence identity to the polypeptide of SEQ ID NO: 16; or
e) wherein the variant has at least 85%, at least 90%, at least 95%, at least 96%, at least 97%, at least 98%, or at least 99%, but less than 100% sequence identity to the polypeptide of SEQ ID NO: 17

Embodiment 90

A variant pullulanase produced by the method of embodiment 89.

Embodiment 91

A composition comprising the variant pullulanase of any of embodiments 1-90.

Embodiment 92

The composition according to embodiment 91, comprising one or more enzymes selected from the group consisting of: glucoamylase, alpha-amylase, beta-amylase, and protease.

Embodiment 93

The composition according to any of embodiments 91 and 92 comprising a pullulanase of polypeptide of any of embodiments 1-84 and: i) a glucoamylase, an alpha-amylase and a protease; ii) an alpha-amylase and a protease; iii) a glucoamylase and an alpha-amylase; iv) a beta-amylase; or v) a glucoamylase.

Embodiment 94

A use of a variant pullulanase of any of embodiments 1-90 for production of a syrup and/or a fermentation product, e.g., ethanol, from a starch containing material.

Embodiment 95

The use according to embodiment 94, wherein the starch material is gelatinized or un-gelatinized starch material.

Embodiment 96

A process of producing a fermentation product from starch-containing material comprising the steps of:
(a) liquefying starch-containing material in the presence of an alpha amylase;
(b) saccharifying the liquefied material in the presence of a glucoamylase; and
(c) fermenting with a fermenting organism; wherein step (a) and/or step (b) is carried out in the presence of a variant pullulanase of any of embodiments 1-90.

Embodiment 97

A process of producing a fermentation product from starch-containing material, comprising the steps of:
(a) saccharifying starch-containing material at a temperature below the initial gelatinization temperature of said starch-containing material; and
(b) fermenting with a fermenting organism
wherein step (a) is carried out using at least a glucoamylase, and a variant pullulanase of any of embodiments 1-90.

Embodiment 98

The process according to embodiment 97, wherein an alpha amylase is added in step (a).

Embodiment 99

The process according to embodiment 97, wherein saccharification and fermentation is carried out simultaneously.

Embodiment 100

The process according to any of embodiments 96-99, wherein the fermentation product is an alcohol, particularly ethanol.

Embodiment 101

A polynucleotide encoding the variant pullulanase of any of embodiments 1-90.

Embodiment 102

A nucleic acid construct comprising the polynucleotide of embodiment 101.

Embodiment 103

An expression vector comprising the polynucleotide of embodiment 101.

Embodiment 104

A host cell comprising the polynucleotide of embodiment 101.

Embodiment 105

A method of producing a pullulanase variant of any of embodiments 1-90, comprising cultivating the host cell of embodiment 104 under conditions conducive for production of the polypeptide.

Embodiment 106

The method of embodiment 105, further comprising recovering the polypeptide.

Embodiment 107

A whole broth formulation or cell culture composition comprising a polypeptide of any of embodiments 1-90.

The present invention is further described by the following examples that should not be construed as limiting the scope of the invention.

Materials and Methods

Determination of Sugar Profile and Solubilised Dry Solids

The sugar composition of the starch hydrolysates is determined by HPLC and glucose yield is subsequently calculated as DX. ° BRIX, solubilized (soluble) dry solids of the starch hydrolysates are determined by refractive index measurement.

EXAMPLES

Example 1: Construction of Pullulanase Libraries

Genomic DNAs from *Bacillus subtilis* strains harboring pullulanase genes from *Bacillus* sp. NCIB11777 (SEQ ID NO: 7 and 8), *Bacillus deramificans* NN18718 (SEQ ID NO: 4 and 5) and hybrid pullulanase P8, (SEQ ID NO: 1 and 2) which is a hybrid enzyme obtained by combining an N-terminal fragment of the pullulanase derived from *Bacillus acidopullulyticus* described in WO 2009/075682 (SEQ ID NO: 4 in WO2009/075682; GENESEQP: AXB71624), fused to a C-terminal fragment of a pullulanase derived from a *Bacillus deramificans* strain isolated from a humus sample collected in Denmark (a homologous pullulanase from *Bacillus deramificans* was disclosed in U.S. Pat. Nos. 6,074,854 and 5,817,498) were isolated using NucleoSpin® Tissue kit [MACHEREY-NAGEL]. Pullulanase genes were amplified from the genomic DNAs using primers having 15 bp overlaps with an expression vector comprising the genetic elements for *Bacillus* expression and *E. coli* amplification as described in WO 99/43835 using Primer F1 and R1, Primer F2 and R2, and Primer F1 and R2 under the following conditions.

```
Primer F1:
                                      (SEQ ID NO: 10)
ATGTATTATGGAGCTCTATAAAAATGAGGAGGGAACCGAATGTCCCTAAT

ACGTTCTAG

Primer R1:
                                      (SEQ ID NO: 11)
TTATTGATTAACGCGTTTAATTTTGATCAATGACATC
```

-continued

Primer F2:
(SEQ ID NO: 12)
ATGTATTATGGAGCTCTATAAAAATGAGGAGGGAACCGAATGGCTAAAAA
ACTAATTTATG Primer R2:
(SEQ ID NO: 13)
TTATTGATTAACGCGTTTACTTTTTACCGTGGTCTG Phusion polymerase (thermo scientific): Total 20 µl: 1.0 µl Template (100 ng/µl), 4.8 µl H₂O, 4 µl, Phusion HF Buffer: 1.6 µl dNTP (2.5 mM): 0.2 µl Reverse primer (20 µM), 0.4 µl Phusion (2U/µl), 8.0 µl Forward mutation primer (1 µM). PCR-program: 98° C./30 sec, 30×(98° C./10 sec, 60° C./20 sec, 72° C./3 min), 72° C./5 min, 4° C./∞

The resultant PCR fragments were purified by Nucleo-Spin® Gel and PCR Clean-up kit [MACHEREY-NAGEL] and ligated to the vector by In fusion cloning (Clontech). The in fusion mixture was then introduced into *E. coli* DH5a, Jet Competent *E. coli* Cell, BDL. The resultant plasmids were confirmed to have designed sequences and named pGMM, pD2 homolog and p008 and used as templates for library construction. All libraries were constructed by the following steps. A reverse or forward primer having NNK or desired mutation(s) at target site(s) with 15 bp overlaps each other were designed and two PCRs were carried out using Primer1F or 2F and the reverse primer and the forward primer and Primer 1R or 2R using appropriate templates (pGMM, pD' or p008). The resultant PCR fragments were purified by NucleoSpin® Gel and PCR Clean-up kit [MACHEREY-NAGEL] and mixed with an expression vector digested with Sacl and MIul and in fusion mixture to introduce into *E. coli*. The resultant *E. coli* libraries were recovered and transformed into *Bacillus subtilis* to construct *Bacillus* libraries having desired mutations as shown in Table 1a and Table 1b.

TABLE 1a

Substitutions of thermostabilized variants of P008 (SEQ ID NO: 3)

| Position | Substitution(s) |
|---|---|
| P022 | V486C T492S |
| P035 | N368G |
| P040 | N368G M402T |
| P075 | E699R |
| P076 | E150R |
| P091 | T631S S632C |
| P092 | N346S |
| P097 | V486C T492S T631S S632C |
| P129 | N243E |
| P130 | S244K |
| P132 | V143G |
| P136 | N393A |
| P140 | N393A T631S S632C |
| P147 | N610R |
| P148 | N610L |
| P150 | T631S S632C E699R |
| P155 | G624S |
| P161 | N393A V486C T492S T631S S632C |
| P162 | N393A G624S S632C |
| P172 | N393A N610R T631S S632C |
| P173 | N393A G624S T631S S632C |
| P178 | F456A |
| P188 | N393A N610R G624S T631S S632C |
| P189 | N393A V486C T492S G624S T631S S632C |
| P190 | N393A V486C T492S N610R G624S T631S S632C |
| P191 | N368G N393A V486C T492S N610R G624S T631S S632C |
| P192 | N393A V486C T492S N610R G624S T631S S632C E699R |
| P193 | N346S N393A V486C T492S N610R G624S T631S S632C |
| P194 | N393A F456A V486C T492S N610R G624S T631S S632C |
| P199 | N393A T492S N610R G624S T631S S632C |

TABLE 1a-continued

Substitutions of thermostabilized variants of P008 (SEQ ID NO: 3)

| Position | Substitution(s) |
|---|---|
| P202 | N368G N393A T492S N610R G624S T631S S632C |
| P203 | A345P N393A V486C T492S N610R G624S T631S S632C |
| P204 | N368G K370S I373L N393A V486C T492S N610R G624S T631S S632C |
| P205 | I381V Q385E Q387L N393A V486C T492S N610R G624S T631S S632C |
| P206 | I381V N382T Q385E Q387L N393A V486C T492S N610R G624S T631S S632C |
| P212 | A345P N368G N393A T492S N610R G624S T631S S632C |
| P213 | N368G I381V Q385E Q387L N393A T492S N610R G624S T631S S632C |
| P222 | A345P N368G I381V Q385E Q387L N393A T492S N610R G624S T631S S632C |
| P223 | A345P N368G I381V Q385E Q387L N393A T492S N610R G624S T631S S632C V665I |
| P224 | N393A T430R Q431E L432F V486C T492S N610R G624S T631S S632C |
| P225 | N393A Q431E L432F V486C T492S N610R G624S T631S S632C |
| P226 | N393A I429V Q431E V486C T492S N610R G624S T631S S632C |
| P227 | N393A I429V T430R Q431E L432F V486C T492S N610R G624S T631S S632C |
| P229 | N368GI381V Q385E Q387L N393A Q431E L432F T492S N610R G624S T631S S632C |
| P230 | A345P N368GI381V Q385E Q387L N393A Q431E L432F T492S N610R G624ST631S S632C |
| P231 | A345P N368GI381V Q385E Q387L N393A Q431E L432F T492S N610R G624ST631S S632C V665I |
| P242 | A345P N368GI381V Q385E Q387L N393A T492S N610R G624S T631S S632C |

Substitutions shown to have thermoactivity improving effects in SEQ ID NO: 3 were tested in SEQ ID NO: 6 according to below tables 1b and ic. Table Ic use the numbering in SEQ ID NO: 3.

TABLE 1b

Substitutions of thermostabilized variants of *Bacillus deramificans* pullulanase (D2 homolog) (SEQ ID NO: 6) Position numbering is according to SEQ ID NO: 6.

| Variant No. | Substitution(s) |
|---|---|
| P233 | N468G |
| P234 | N493A |
| P235 | A592S |
| P236 | N710R |
| P237 | G724S |
| P238 | T731S S732C |
| P239 | N710R G724S T731S S732C |
| P240 | N468G N493A A592S |
| P241 | N468G N493A A592S N710R G724S T731S S732C |

TABLE 1c

Variants of SEQ ID NO: 6 using numbering according to SEQ ID NO: 3.

| Variant No. | Substitution referring to SEQ ID NO: 3. |
|---|---|
| P233 | N368G |
| P234 | N393A |
| P235 | A492S |
| P236 | N610R |
| P237 | G624S |
| P240 | N368G N393A A492S |
| P259 | N368G N393A |
| P261 | N393A N610R |

TABLE 1c-continued

Variants of SEQ ID NO: 6 using numbering according to SEQ ID NO: 3.

| Variant No. | Substitution referring to SEQ ID NO: 3. |
|---|---|
| P262 | N368G N393A N610R |
| P265 | N368G N393A N610R G624S T492A |

TABLE 1d

Variants of SEQ ID NO: 16 (P258).

| Variant No. | Substitution referring to SEQ ID NO: 3. |
|---|---|
| P219 | N368G N393A T492A N610R G624S T631S S632C |
| P306 | N368G N393A T492A N610R G624S T631S S632C Q431E L432F |

TABLE 1e

Variants of SEQ ID NO: 17 (P243).

| Variant No. | Substitution referring to SEQ ID NO: 3. |
|---|---|
| P252 | N368G N393A N610R G624S T631S S632C |
| P303 | N368G N393A N610R G624S T631S S632C Q431E L432F |

In order to test if the improved thermo-activity resulting from the introduced substitutions in the catalytic domain, could be maintained when N-terminal parts of the parent enzyme were replaced by N-terminal parts from other pullulanases the following hybrid pullulanases were constructed.

TABLE 2

Variants having substitutions in the catalytic domain were constructed by replacing N-terminal parts with equivalent parts from other pullulanases. The origin of the different N-terminal domains is shown by SEQ ID and for the CD both the origin and the specific substitutions are indicated.

| | CBM41 | X45a | X25 | X45b | CBM48 | Catalytic Domain, CD |
|---|---|---|---|---|---|---|
| P6 | SEQ ID 9 | SEQ ID 9 | No | SEQ ID 9 | SEQ ID 6 | SEQ ID 6 (or 19) |
| P8 | SEQ ID 9 (or 3) | SEQ ID 9 (or 3) | No | SEQ ID 9 (or 3) | SEQ ID 6 (or 3) | SEQ ID 6 (or 3) |
| P-proD' | SEQ ID 6 | SEQ ID 6 | SEQ ID 6 | SEQ ID 6 | SEQ ID 6 | SEQ ID 6 |
| P240 | SEQ ID 6 | SEQ ID 6 | SEQ ID 6 | SEQ ID 6 | SEQ ID 6 | N368G N393A A492S (SEQ ID 6) |
| P254 | SEQ ID 15 | SEQ ID 15 | SEQ ID 15 | SEQ ID 15 | SEQ ID 6 | N368G N393A A492S (SEQ ID 6) |
| P255 | SEQ ID 15 | SEQ ID 15 | SEQ ID 15 | SEQ ID 15 | SEQ ID 9 | N368G N393A A492S (SEQ ID 6) |
| P265* | SEQ ID 15 | SEQ ID 15 | SEQ ID 15 | SEQ ID 15 | SEQ ID 9 | N368G N393A T492A N610R G624S (SEQ ID 6) |
| P256 | SEQ ID 9 | SEQ ID 9 | No | SEQ ID 9 | SEQ ID 6 | N368G N393A A492S (SEQ ID 6) |
| P257 | SEQ ID 9 | SEQ ID 9 | No | SEQ ID 9 | SEQ ID 9 | N368G N393A A492S (SEQ ID 6) |
| P267* | SEQ ID 9 | SEQ ID 9 | No | SEQ ID 9 | SEQ ID 6 | N368G N393A T492A N610R G624S (SEQ ID 6) |
| P216 | SEQ ID 15 | SEQ ID 15 | SEQ ID 15 | SEQ ID 15 | SEQ ID 9 | N368G N393A T492S N610R G624S T631S S632C (SEQ ID 6) |
| P252 | SEQ ID 15 | SEQ ID 15 | SEQ ID 15 | SEQ ID 15 | SEQ ID 9 | N368G N393A N610R G624S T631S S632C (SEQ ID 17) |
| P303 | SEQ ID 15 | SEQ ID 15 | SEQ ID 15 | SEQ ID 15 | SEQ ID 9 | N368G N393A N610R G624S T631S S632C Q431E L432F (SEQ ID 17) |
| P219 | SEQ ID 15 | SEQ ID 15 | SEQ ID 15 | SEQ ID 15 | SEQ ID 9 | N368G N393A T492A N610R G624S T631S S632C (SEQ ID 16) |
| P306 | SEQ ID 15 | SEQ ID 15 | SEQ ID 15 | SEQ ID 15 | SEQ ID 9 | N368G N393A T492A N610R G624S T631S S632C Q431E L432F (SEQ ID 16) |

*P265 and P267 were borne with the A in position 492, however, this position is contributing to the observed effect and should not be modified unless the substitution is to S.

Example 2: Construction of Improved Variants of P303

The pullulanase variant, P303, was used as the starting point for further variant selection resulting in the below list of specific variants.

TABLE 3

Substitutions in addition to P303 substitutions (numbering refers to SEQ ID NO: 26)

| | |
|---|---|
| P316 | Q258A |
| P317 | Q287R |
| P318 | Q352A |
| P319 | Q356R |
| P323 | Q258A + Q352A + Q356R |
| P324 | Q258A + Q287R + Q352A + Q356R |
| P329 | V212I |
| P347 | H186A |
| P368 | V212I + Q258A + Q287R + Q352A + Q356R |
| P369 | H186A + V212I + Q258A + Q287R + Q352A + Q356R |
| P370 | Y27K + H79Y + V212I + Q258A + Q287R + Q352A + Q356R |
| P372 | Q258A + Q287R + N322P + Q352A + Q356R |
| P375 | H186A + V212I + Q258A + Q287R + N322P + Q352A + Q356R |
| P376 | H186A + V212I + Q258A + Q287R + Q352A + Q356R |
| P377 | H186A + V212I + Q258A + Q287R + N322P + Q352A + Q356R |
| P378 | Y27K + H79Y + H186A + V212I + Q258A + Q287R + Q352A + Q356R |
| P385 | Y27K + H79Y + H186A + V212I + Q258A + Q287R + N322P + Q352A + Q356R |
| P397 | Y27K + H79Y + H186A + V212I + Q258A + Q287R + N322P + Q352A + Q356R + D686S |
| P415 | N19G + Y27K + H79Y + H186A + V212I + Q258A + Q287R + N322P + Q352A + Q356R + D686S |
| P416 | N19G + Y27K + H79Y + H186A + V212I + Q258A + Q287R + G296R + N322P + Q352A + Q356R + D686S |
| P417 | Y27K + H79Y + H186A + V212I + Q258A + Q287R + N322P + Q352A + Q356R + V586A + D686S |
| P418 | Y27K + H79Y + H186A + V212I + Q258A + Q287R + N322P + Q352A + Q356R + D686S + E799R |
| P424 | N19G + Y27K + H79Y + H186A + V212I + Q258A + Q287R + N322P + Q352A + Q356R + V586A + D686S |

TABLE 3-continued

Substitutions in addition to P303 substitutions (numbering refers to SEQ ID NO: 26)

| | |
|---|---|
| P425 | N19G + Y27K + H79Y + H186A + V212I + Q258A + Q287R + N322P + Q352A + Q356R + D686S + E799R |
| P426 | N19G + Y27K + H79Y + H186A + V212I + Q258A + Q287R + N322P + Q352A + Q356R + Q485E + D686S + E799R |
| P427 | N19G + Y27K + H79Y + H186A + V212I + Q258A + Q287R + N322P + Q352A + Q356R + Q487L + D686S + E799R |
| P428 | N19G + Y27K + H79Y + H186A + V212I + Q258A + Q287R + N322P + Q352A + Q356R + V586A + D686S + E799R |
| P435 | N19G + Y27K + H79Y + H186A + V212I + Q258A + Q287R + G296R + N322P + Q352A + Q356R + V586A + D686S + E799R |
| P436 | N19G + Y27K + H79Y + H186A + V212I + Q258A + Q287R + G296R + N322P + Q352A + Q356R + Q487L + V586A + D686S + E799R |
| P472 | N19G + Y27K + H79Y + H186A + V212I + Q258A + Q287R + N322P + Q352A + Q356R + Q487L + D686S + C732S + E799R |
| P484 | N19G + Y27K + H79Y + H186A + V212I + Q258A + Q287R + N322P + Q352A + Q356R + Q487L + D686S + C732S + E799R |

TABLE 3-continued

Substitutions in addition to P303 substitutions (numbering refers to SEQ ID NO: 26)

| | |
|---|---|
| P485 | N19G + Y27K + H79Y + H186A + V212I + Q258A + Q287R + N322P + Q352A + Q356R + Q487L + S557A + L559G + D686S + E799R |
| P486 | N19G + Y27K + H79Y + H186A + V212I + Q258A + Q287R + N322P + Q352A + Q356R + H421E + Q487L + S557A + L559G + V586A + D686S + E799R |

Example 3: Construction of Variants P287 and P380

Starting from P202, described in example 1 above, three further substitutions, N222P+Q252A+Q256R, were introduced in order to generate P287.

Thus, P287, is SEQ ID NO: 3 comprising the substitutions: N222P+Q252A+Q256R+N368G+N393A+T492S+N610R+G624S+T631S+S632C.

Another variant, P380, was generated by replacing the catalytic domain of P008 with the catalytic domain from P306. P380 is included herein as SEQ ID NO: 28.

Thus, P380, has the structure as shown below:

| | CBM41 | X45a | X25 | X45b | CBM48 | Catalytic Domain, CD |
|---|---|---|---|---|---|---|
| P380 | SEQ ID 9 (or 3) | SEQ ID 9 (or 3) | No | SEQ ID 9 (or 3) | SEQ ID 9 (or 3) | N368G N393A T492A N610R G624S T631S S632C Q431E L432F (SEQ ID 16) |

Example 4: Construction of Improved Variants of P380

The pullulanase variant, P380, was used as the starting point for further variant selection resulting in the below list of specific variants.

TABLE 4

Substitution in addition to P380 substitutions (numbering refers to SEQ ID NO: 3)

| | |
|---|---|
| P388 | Y27K + H79Y + Q187R + S798R |
| P398 | Y27K + H79Y + Q187R + D586S + S798R |
| P403 | Y27K + H79Y + Q187R + D586S + E699R + S798R |
| P408 | Y27K + H79Y + Q187R + T486S + D586S + S798R |
| P423 | N19G + Y27K + H79Y + Q187R + T486C + D586S + E699R + S798R |
| P430 | N19G + Y27K + H79Y + Q187R + Q385E + T486C + D586S + E699R + S798R |
| P431 | N19G + Y27K + H79Y + Q187R + Q387L + T486C + D586S + E699R + S798R |
| P443 | N19G + Y27K + H79Y + Q187R + Q387L + Q459G + T486C + D586S + C632S + E699R + S798R |
| P444 | N19G + Y27K + H79Y + Q187R + Q387L + T486C + D586S + C632S + Q675L + E699R + S798R |
| P448 | N19G + Y27K + H79Y + Q187R + V196R + Q387L + T486C + D586S + C632S + E699R + S798R |
| P449 | N19G + Y27K + H79Y + Q187R + V196R + Q387L + T486C + D586S + C632S + Q675L + E699R + S798R |
| P450 | N19G + Y27K + H79Y + Q187R + V196R + Q387L + Q459G + T486C + D586S + C632S + Q675L + E699R + S798R |
| P470 | N19G + Y27K + H79Y + Q187R + Q387L + D586S + E699R + S798R |
| P481 | N19G + Y27K + H79Y + Q187R + H321E + Q387L + D586S + E699R + S798R |
| P482 | N19G + Y27K + H79Y + Q187R + Q387L + Q459G + D586S + E699R + S798R |
| P483 | N19G + Y27K + H79Y + Q187R + Q387L + D586S + C632S + E699R + S798R |
| P493 | N19G + Y27K + H79Y + Q187R + E310A + D311K + Q387L + D586S + E699R + S798R |
| P507 | N19G + Y27K + H79Y + Q187R + E310A + D311K + Q387L + Q459G + D586S + E699R + S798R |

Example 5: Pullulanase Assay

Red-Pullulan Assay (Meqazyme)
Substrate Solution
0.1 g red-pullulan (megazyme S-RPUL)
0.75 ml 2M sodium acetate, pH5.5
14.25 ml H2O 10 μl of enzyme samples were mixed with 80 μl of substrate solution and incubated at set temperatures (ex. 55, 60, 650C) for 20 min. 50 μl of ethanol was added to the reaction mixtures and centrifuge for 10 min. at 3500 rpm.

The supernatants were carefully taken out and the absorbance, A510 was determined.

PAHBAH-Pullulan Assay
Substrate Solution
0.15 g BH4-pullulan
25 ml 50 mM Na acetate buffer, pH5.5
PAHBAH solution
0.0552 g Bismuth (III)-acetate
0.2 g PAHBAH 0.5 g Potassium sodium tartrate, tetrahydrate
10 ml 500 mM NaOH 10 µl of enzyme samples were mixed with 110 µl of substrate solution and incubated at set temperatures (e.g., 55, 60, 65OC) for 20 min. 40 µl of PAHBAH solution was added to the reaction mixtures, incubated for another 20 min at 50° C. and the absorbance, A405 was determined.

Lintner Soluble Waxy Starch Assay

Substrate Solution 0.2 g Lintner's waxy corn starch
2.5 ml 2M sodium acetate
97.5 ml $H_2O$ 5 µl of enzyme samples were mixed with 100 µl of substrate solution and incubated at set temperatures (e.g., 55, 60, 65, 70, 75OC) for 20 min. 100 µl of 0.15% $I_2$/1.5% KI solution was added to the reaction mixtures and the absorbance, A610 was determined.

PHADEBAS Assay

Substrate Soln.

1 tablet of PHADEBAS alpha-amylase tablet
5 ml 50 mM Na acetate buffer, pH5
40 sec. microwave oven up to boiling Stop Soln.

18% acetic acid

Assay Method

Enzyme Reaction in 96 Well PCR Tube 10 ul of enzyme samples were mixed with 100 ul of substrate solution and incubated at set temperatures (eg. 55, 60, 65OC) for 20 min. 50 ul of stop solution was added to the reaction mixtures and centrifuge for 10 minutes at 3500 rpm. The supernatants were carefully taken out and the absorbance at A600 was read.

Example 6: Evaluation of Thermoactivity

*Bacillus* libraries constructed as in example 1 were fermented in 96 well MTPs containing TB-gly medium (13.3 g/L Bacto™ Tryptone, 26.6 g/L Bacto™ Yeast extract D, 4.4 g/L Glycerol) with 6 mg/L chloramphenicol at 220 rpm, 370C and pullulanase activities were measured at several temperatures by Lintner soluble starch assay and/or Phadebas assay described in EXAMPLE 2. Relative activity of pullulanase variants showing higher thermoactivity compared to parental pullulanases as shown in tables.

| | Relative activity of 70° C./65° C. (%) | Relative activity of 72° C./65° C. (%) | Relative activity of 74° C./65° C. (%) |
|---|---|---|---|
| SEQ ID NO: 9 | 15 | 6 | |
| SEQ ID NO: 3 | 54 | 6 | 2 |
| P091 | 98 | 31 | |
| P092 | 86 | 4 | |
| P129 | 83 | 8 | |
| P130 | 71 | 10 | |
| P132 | 69 | 11 | |
| P136 | 115 | 61 | |
| P147 | 74 | 58 | |
| P148 | 64 | 51 | |
| P155 | 87 | 14 | |
| P178 | 62 | 11 | |
| P097 | 118 | 71 | |
| P140 | 106 | 81 | |
| P150 | 82 | 44 | 10 |
| P173 | 95 | 75 | 37 |

| | Relative activity of 68° C./60° C. (%) | Relative activity of 70° C./60° C. (%) |
|---|---|---|
| SEQ ID NO: 3 | 67 | 35 |
| P022 | 90 | 57 |
| P035 | 113 | 119 |
| P040 | 104 | 105 |
| P075 | 86 | 72 |
| P076 | 80 | 55 |

| | Relative activity (%) | | | | | | | |
|---|---|---|---|---|---|---|---|---|
| | 70/65 | 72/65 | 74/65 | 76/65 | 78/65 | 72/70 | 74/70 | 76/70° C. |
| SEQ ID NO: 9 | 6% | 3% | 1% | | | | | |
| SEQ ID NO: 3 | 28% | 5% | 1% | | | 52% | 8% | 5% |
| P091 | | | | | | 72% | 12% | 6% |
| P136 | | | | | | 75% | 9% | 6% |
| P147 | | | | | | 53% | 5% | 4% |
| P155 | 59% | 6% | 0% | | | 59% | 8% | 6% |
| P140 | | | | | | 91% | 26% | 8% |
| P161 | 118% | 82% | 31% | | | 97% | 54% | 10% |
| P162 | | | | | | 88% | 27% | 7% |
| P172 | 111% | 75% | 19% | | | 95% | 52% | 8% |
| P173 | 108% | 84% | 26% | | | 96% | 53% | 9% |
| P188 | 97% | 100% | 36% | | | | | |
| P189 | 107% | 81% | 34% | | | | | |
| P190 | 122% | 106% | 61% | 13% | | | | |
| P191 | 148% | 134% | 87% | 30% | | | | |
| P193 | 135% | 112% | 21% | | | | | |
| P194 | 124% | 68% | 9% | | | | | |
| P199 | 147% | 106% | 55% | 7% | | | | |
| P202 | | 112% | 68% | 12% | | | | |
| P203 | | 115% | 76% | 29% | | | | |
| P204 | | 110% | 66% | 18% | | | | |
| P205 | | 103% | 63% | 42% | | | | |
| P206 | | 91% | 71% | 34% | | | | |
| P212 | | 97% | 84% | 22% | | | | |
| P213 | | 86% | 70% | 44% | | | | |
| P222 | | 98% | 71% | 8% | | | | |
| P223 | | 92% | 16% | 0% | | | | |
| P224 | | | 99% | 43% | 4% | | | |
| P225 | | | 108% | 76% | 8% | | | |
| P226 | | | 113% | 66% | 6% | | | |
| P227 | | | 99% | 29% | 3% | | | |
| P230 | | 102% | 78% | 64% | 12% | | | |
| P231 | | 101% | 65% | 50% | 12% | | | |
| P242 | | | 84% | 55% | 4% | | | |

| | Relative activity (%) | |
|---|---|---|
| | 65° C./60° C. | 67° C./60° C. |
| *Bacillus deramificans* pullulanase (SEQ ID NO: 6) | 70% | 20% |
| P233 | 100% | 79% |
| P234 | 102% | 81% |
| P235 | 92% | 25% |
| P236 | 100% | 64% |
| P240 | 101% | 86% |

| | Relative activity 65° C./60° C. |
|---|---|
| *Bacillus deramificans* pullulanase (SEQ ID NO: 6) | 65% |
| P261 | 69% |
| P262 | 77% |
| P265 | 84% |

|  | Relative activity 70° C./60° C. |
|---|---|
| *Bacillus deramificans* pullulanase (SEQ ID NO: 6) | 36% |
| P259 | 106% |
| P240 | 95% |

Example 7: Fermentation of the *Bacillus* Strains

*B. subtilis* strains were fermented on a rotary shaking table in 500 ml baffled flasks containing 100 ml TB-gly with 6 mg/L chloramphenicol at 220 rpm, 37° C. The culture was centrifuged (20000×g, 20 min) and the supernatants were carefully decanted from the precipitates. The supernatants were filtered through a 0.45 um filter unit to remove the rest of the *Bacillus* host cells.

Example 8: Purification of Pullulanases

Purification of pullulanases was carried out by β-cyclodextrin affinity column and followed by anion exchange column chromatography. After purification, pullulanases were dialyzed against 20 mM sodium acetate buffer (pH 5.5) and concentrated.

Example 9: Enzyme Thermostability Measurement

Purified enzyme was diluted with 50 mM sodium acetate pH 5.0 or 4.3 to 0.5 mg/ml and mixed with the equal volume of SYPRO Orange (Invitrogen) diluted with Milli-Q water. Thirty microliters of mixture solution was transfer to Light-Cycler 480 Multiwell Plate 96 (Roche Diagnostics) and the plate was sealed.

Equipment parameters of TSA:
Apparatus: LightCycler 480 Real-Time PCR System (Roche *Applied Science*)
Scan rate: 0.02° C./sec
Scan range: 37-96° C.
Scan rate: 1.26° C./min
Integration time: 0.5 sec
Excitation wave length 465 nm
Emission wave length 580 nm The obtained fluorescence signal was normalized into a range of 0 and 1. The Melting temperature (Tm) was defined as the temperature where the normalized value is closest to 0.5.

|  | TSA Tm (° C.) | |
|---|---|---|
|  | pH 4.3 | pH 5.0 |
| SEQ ID NO: 9 | 69 | 68 |
| SEQ ID NO: 3 | 72.5 | 72.7 |
| P091 | 76.5 | 77 |
| P136 | 76.9 | 76.5 |
| P155 | 76 | 76.3 |
| P097 | 77.7 | 77.4 |
| P140 | 78.1 | 77.5 |
| P161 | 79.2 | 78.5 |
| P172 | 78.1 | 77.8 |
| P173 | 78.5 | 77.6 |
| P190 | 79.2 | 78.5 |

Example 10: Temperature Activity Measurement

Activity measurement of pullulanases was carried out in the range of 55-77.5° C. at pH 5.0 by PHADEBAS assay described in EXAMPLE 2. The temperature optimum of the variants were higher than the parental P008, around 70-72.5° C. as shown in the below table.

|  | Temperature (° C.) | | | | | | | |
|---|---|---|---|---|---|---|---|---|
|  | 55 | 60 | 65 | 67.5 | 70 | 72.5 | 75 | 77.5 |
| SEQ ID NO: 3 | 53% | 79% | 89% | 100% | 93% | 15% | 2% | 1% |
| P161 | 25% | 46% | 99% | 91% | 98% | 100% | 20% | 2% |
| P172 | 38% | 56% | 68% | 90% | 100% | 85% | 17% | 1% |
| P173 | 35% | 55% | 81% | 97% | 100% | 89% | 15% | 1% |
| P190 | 23% | 36% | 62% | 88% | 98% | 100% | 34% | 2% |

Example 11: Catalytic Domain Variants Having N-Terminal Parts Replaced

Two variants having substitutions in the catalytic domain, P240 and P265, described in example 3 were tested after replacement of the N-terminal domains. The replacement resulted in P256 and P267.

*Bacillus* clones were fermented in 96 well MTPs containing TB-gly medium (13.3 g/L Bacto™ Tryptone, 26.6 g/L Bacto™ Yeast extract D, 4.4 g/L Glycerol) with 6 mg/L chloramphenicol at 220 rpm, 37° C. and pullulanase activities were measured at several temperatures by Phadebas assay described in EXAMPLE 2. Relative activity of pullulanase variants showing higher thermoactivity compared to parental pullulanases as shown in below table.

|  | Relative activity at indicated temp (° C.) | | | |
|---|---|---|---|---|
|  | 65/60 | 67/60 | 70/60 | 72/60 |
| SEQ ID NO: 19 | 88% | 50% | 9% | 9% |
| P256 | 105% | 90% | 17% | 9% |
| P267 | 96% | 101% | 28% | 10% |

Example 12: Relative Activity of Selected Variants

Purified enzyme was diluted to a fixed concentration with dilution buffer. Ten microliters of enzyme solution was added to 110 ul of preincubated 0.5% substrate solution (at 60-75° C. at 5° C. intervals) and incubated for 30 min. The reaction was stopped by adding 10 ul of 500 mM NaOH and 40 ul of PAHBAH solution was added there. After 20 min incubation at 55° C., the absorbance at A405 was read.

|  | Relative activity | | |
|---|---|---|---|
|  | 65° C./60° C. | 70° C./60° C. | 70° C./75° C. |
| Commercial PromozymeD | 65% | 0% | 0% |
| P008 | 112% | 117% | 28% |
| P199 | 122% | 141% | 119% |
| P202 | 123% | 141% | 125% |
| P216 | 123% | 137% | 75% |
| P219 | 118% | 121% | 62% |
| P240 | 114% | 58% | 3% |
| P252 | 132% | 136% | 22% |
| P254 | 115% | 21% | 6% |
| P256 | 112% | 40% | 6% |
| P303 | 125% | 135% | 68% |

| | Relative activity | |
|---|---|---|
| | 72° C./60° C. | 74° C./60° C. |
| P303 | 37% | 12% |
| P306 | 82% | 29% |
| P219 | 65% | 20% |
| Commercial PromozymeD | 0% | 0% |

Example 13: Improved Specific Activity for Selected Variants

Specific activities toward Pindex100 (DE3) were determined using the method described in a modified method of PAHBAH-Pullulan assay described in EXAMPLE 2 using purified pullulanase samples (2 µg/ml) at 60° C. and 65° C. Instead of using pullulan, Pindex100 was used in this experiment. The specific activities are listed as relative activity to that of purified commercial product, Promozyme® D2 (Sigma E2412)

| Specific activity toward maltodextrin (100% at promozyme D at 60° C.) | | |
|---|---|---|
| | 60° C. | 65° C. |
| Commercial PromozymeD2 | 100% | 65% |
| P199 | 108% | 132% |
| P202 | 110% | 135% |
| P219 | 127% | 150% |
| P240 | 141% | 161% |
| P252 | 108% | 143% |
| P254 | 122% | 140% |
| P256 | 128% | 143% |
| P303 | 110% | 137% |
| P380 | 97% | 116% |

Example 14: Relative Activity Measurements of Selected Pullulanase Variants

Relative activity measurements of selected pullulanase variants was carried out in the range of 65-79° C. at pH 5.0 by the PHADEBAS assay described in EXAMPLE 2. The results are shown in the tables below.

| | Relative activity | | | |
|---|---|---|---|---|
| | 72° C./65° C. | 74° C./65° C. | 76° C./65° C. | 78° C./65° C. |
| P303 | 75% | 12% | 1% | 0% |
| P316 | 91% | 36% | | |
| P317 | 97% | 42% | | |
| P318 | 91% | 39% | | |
| P319 | 93% | 40% | | |
| P323 | 86% | 27% | | |
| P324 | 74% | 17% | 2% | |
| P329 | 76% | 21% | | |
| P347 | 75% | 13% | | |
| P368 | 88% | 62% | | |
| P369 | 92% | 59% | 2% | |
| P370 | 105% | 81% | 11% | |
| P372 | 109% | 87% | 10% | |
| P375 | 113% | 93% | 4% | |
| P376 | 112% | 98% | 4% | |
| P377 | 93% | 78% | 16% | |
| P378 | 108% | 86% | | |
| P385 | 104% | 63% | 5% | |
| P397 | 90% | 46% | 3% | |
| P415 | | 46% | 6% | |
| P416 | | 32% | | |
| P417 | 52% | 8% | | |
| P418 | 48% | | | |
| P424 | 60% | 12% | | |
| P425 | 49% | 7% | | |
| P426 | 25% | 3% | | |
| P427 | 67% | 20% | | |
| P428 | 61% | 14% | | |
| P435 | | 4% | | 2% |
| P436 | | 15% | | 4% |
| P472 | 47% | 27% | | |
| P484 | 45% | 24% | | |
| P485 | 80% | 60% | | |
| P486 | 79% | 68% | | |

| | Relative activity | | | |
|---|---|---|---|---|
| | 72° C./65° C. | 74° C./65° C. | 76° C./65° C. | 78° C./65° C. |
| P202 | 109% | 96% | 26% | 2% |
| P287 | 107% | 96% | 42% | 3% |
| P380 | 101% | 97% | 78% | 7% |

| | Relative activity | | |
|---|---|---|---|
| | 76° C./65° C. | 78° C./65° C. | 79° C./65° C. |
| P202 | 26% | 2% | |
| P380 | 32% | 7% | |
| P388 | 68% | | |
| P398 | 51% | 19% | |
| P403 | 70% | 46% | |
| P408 | 92% | 57% | |
| P423 | 87% | 73% | |
| P430 | 90% | 79% | |
| P431 | 93% | 95% | |
| P443 | 100% | 62% | |
| P444 | 77% | 71% | |
| P448 | 81% | 60% | |
| P449 | 70% | 60% | |
| P450 | 73% | | |
| P470 | 84% | 68% | |
| P481 | 89% | 63% | |
| P482 | 78% | 59% | |
| P483 | 62% | 35% | |
| P493 | 87% | 71% | 33% |
| P507 | 88% | 74% | 38% |

Example 15: Enzyme Thermostability Measurement (TSA)

The thermo-stability measured as melting temperature (Tm) was determined as described in example 9.

Purified enzyme was diluted with 50 mM sodium acetate pH 5.0 or 4.3 to 0.5 mg/ml and mixed with the equal volume of SYPRO Orange (Invitrogen) diluted with Milli-Q water. Thirty microliters of mixture solution was transfer to Light-Cycler 480 Multiwell Plate 96 (Roche Diagnostics) and the plate was sealed.

Equipment parameters of TSA:
Apparatus: LightCycler 480 Real-Time PCR System (Roche Applied Science)
Scan rate: 0.02° C./sec
Scan range: 37-96° C.
Scan rate: 1.26° C./min Integration time: 0.5 sec
Excitation wave length 465 nm
Emission wave length 580 nm
The obtained fluorescence signal was normalized into a range of 0 and 1. The Melting temperature (Tm) was defined as the temperature where the normalized value is closest to 0.5. Tm analysis by TSA

|  | Tm (° C.) | |
|---|---|---|
|  | pH 4.3 | pH 5.0 |
| SEQ ID NO: 9 | 69 | 68 |
| P202 | 75.7 | 76.07 |
| P199 | 75.05 | 75.5 |
| P213 | 78.55 | 78.7 |
| P225 | 80.29 | 80.74 |
| P216 | 72.68 | 73.49 |
| P217 | 73.08 | 74.1 |
| P218 | 72.05 | 72.65 |
| P219 | 72.11 | 72.89 |
| P252 | 71.53 | 72.08 |
| P303 | 72.58 | 73.54 |
| P380 | 75.5 | 76.7 |
| P370 | 74.1 | 74.6 |
| P379 | 72.2 | 73.2 |
| P368 | 73.4 | 73.9 |
| P385 | 73.5 | 73.3 |
| P408 | 77.2 | 78.5 |
| P423 | 71.6 | 74.7 |
| P425 | 71.7 | 72.7 |
| P470 | 80.1 | 80.3 |
| P472 | 76.2 | 75.7 |

Example 16: Saccharification Test of Selected Variants

Maltodextrin which dextrose equivalent (DE) was adjusted to 11 was prepared from a conventional starch liquefaction process using corn starch and spray-dried for this experiment. The maltodextrin powder was dissolved in hot milliQ water and the pH was adjusted by HCl/NaOH to be 4.3 at 65° C., and then the solid was adjusted to 40% dry solid (DS) by measuring refractive index (RI) of the syrup. The syrup was conducted in 25 ml glass vial, and saccharification was started at 65° C. by adding 2 ml enzyme mixture containing purified glucoamylase JGA098 and pullulanase so that the final dosage of glucoamylase was 0.194 AGU/gDS and that of pullulanase was 5.3 or 10.7 ug/gDS. The samples were incubated at 65° C. with stirring and were sampled at different time points. At each sampling, 0.75 ml of the syrup was heat-inactivated at 100° C. for 15 min, and then diluted 6-fold with distilled water and filtered through 0.2 pm nylon syringe filter prior to HPLC analysis. Twenty microliter of the syrup sample was applied to HPX-87C column (Bio-Rad) equilibrated with distilled water at flow rate of 0.5 ml/min at 85° C., and glucose and other oligosaccharides were fractionated under isocratic conditions and detected by a RI detector. Glucose yield (% DX) was calculated as the percentage of glucose peak area in total area detected. The enzyme dosages and the % DX against incubation time were shown in the Table below.

| % DX of the syrup at different time points. | | | | | | |
|---|---|---|---|---|---|---|
| Time [hr] | PromozymeD2 5.3 ug/gDS | P256 5.3 ug/gDS | P240 5.3 ug/gDS | PromozymeD2 10.7 ug/gDS | P256 10.7 ug/gDS | P240 10.7 ug/gDS |
| 8 | 62.7 | 62.4 | 62.8 | 63.6 | 63.3 | 63.3 |
| 16 | 79.7 | 80.8 | 81.1 | 83.1 | 83.0 | 83.8 |
| 24 | 86.7 | 87.8 | 88.8 | 90.5 | 90.7 | 91.3 |
| 36 | 91.3 | 92.5 | 93.3 | 94.5 | 94.9 | 95.2 |
| 48 | 93.5 | 94.5 | 95.1 | 95.8 | 96.1 | 95.9 |
| 60 | 94.5 | 95.4 | 95.7 | 96.0 | 96.3 | 96.2 |
| 72 | 95.0 | 95.6 | 95.8 | 96.1 | 96.2 | 96.2 |
| 90 | 95.2 | 95.7 | 95.7 | 95.9 | 96.1 | 96.0 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A pullulanase variant comprising a substitution at one or more positions corresponding to positions 368, 393, 492, 610, 631, and 632, of the polypeptide of SEQ ID NO: 3, wherein the pullulanase variant has:
   (a) pullulanase activity,
   (b) at least 85%, but less than 100% sequence identity to the polypeptide of SEQ ID NO: 3,
   (c) has increased thermoactivity compared to the pullulanase of SEQ ID NO: 3; and
   (d) the substitution is selected from the group consisting of:
      (i) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
      (ii) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
      (iii) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
      (iv) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
      (v) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
      (vi) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

2. The pullulanase variant of claim 1, comprising at least two of the following substitutions:
   (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
   (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
   (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
   (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
   (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
   (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

3. The pullulanase variant of claim 1, comprising at least three of the following substitutions:
   (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
   (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
   (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
   (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val, (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val, (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

4. The pullulanase variant of claim 1, comprising at least four of the following substitutions:

(a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val, (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val, (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val, (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val, (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val, (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

5. The pullulanase variant of claim 1, comprising at least five of the following substitutions:

(a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val, (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val, (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val, (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val, (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val, (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

6. The pullulanase variant of claim 1, comprising each of the following substitutions:

(a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val, (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val, (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val, (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val, (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val, (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

7. The pullulanase variant of claim 1, which has at least 90% sequence identity to the polypeptide of SEQ ID NO: 3.

8. The pullulanase variant of claim 1, which has at least 95% sequence identity to the polypeptide of SEQ ID NO: 3.

9. A composition comprising a pullulanase variant of claim 1 and one or more enzymes selected from the group consisting of: alpha-amylase, beta-amylase, glucoamylase, and protease.

10. A process of producing a fermentation product, comprising:

(a) liquefying a starch-containing material in the presence of an alpha amylase;

(b) saccharifying the liquefied material in the presence of a glucoamylase; and (c) fermenting with a fermenting organism; wherein step (a) and/or step (b) is carried out in the presence of a pullulanase variant of claim 1.

11. A process of producing a fermentation product, comprising:

(a) saccharifying a starch-containing material at a temperature below the initial gelatinization temperature of said starch-containing material using at least a glucoamylase, and a pullulanase variant of claim 1; and (b) fermenting with a fermenting organism.

12. A pullulanase variant, which has:

(a) at least 90% sequence identity to the polypeptide of SEQ ID NO: 28, wherein the pullulanase variant has (b) pullulanase activity, (c) increased thermoactivity compared to the pullulanase of SEQ ID NO: 3, and (d) the following amino acid residues at the following positions corresponding to the positions of SEQ ID NO: 3

(i) a glycine residue at position 368, (ii) an alanine residue at position 393, (iii) a glutamic acid residue at position 431, (iv) a phenylalanine residue at position 432, (v) an alanine or serine residue at position 492, (vi) an arginine residue at position 610, (vii) a serine residue at position 624, (viii) a serine residue at position 631, and (ix) a cysteine residue at position 632.

13. The pullulanase variant of claim 12, which has at least 95% sequence identity to the polypeptide of SEQ ID NO: 28.

14. The pullulanase variant of claim 12, which comprises SEQ ID NO: 28.

15. A composition comprising a pullulanase variant of claim 12 and one or more enzymes selected from the group consisting of: alpha-amylase, beta-amylase, glucoamylase, and protease.

16. A process of producing a fermentation product, comprising:

(a) liquefying a starch-containing material in the presence of an alpha amylase;

(b) saccharifying the liquefied material in the presence of a glucoamylase; and (c) fermenting with a fermenting organism; wherein step (a) and/or step (b) is carried out in the presence of a pullulanase variant of claim 12.

17. A process of producing a fermentation product, comprising:

(a) saccharifying a starch-containing material at a temperature below the initial gelatinization temperature of said starch-containing material using at least a glucoamylase, and a pullulanase variant of claim 12; and (b) fermenting with a fermenting organism.

18. A pullulanase variant comprising a variant catalytic domain, wherein the variant catalytic domain comprises a substitution at one or more positions corresponding to positions 368, 393, 492, 610, 631, and 632 of the polypeptide of SEQ ID NO: 3, wherein:
  (a) the pullulanase variant has pullulanase activity,
  (b) the variant catalytic domain at least 85%, but less than 100% sequence identity to amino acids 330 to 828 of SEQ ID NO: 3,
  (c) the pullulanase variant has increased thermoactivity compared to the pullulanase of SEQ ID NO: 3; and
  (d) the substitution is selected from the group consisting of:
    (i) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
    (ii) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
    (iii) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
    (iv) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
    (v) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
    (vi) a substitution at a position corresponding to position 632 with Ala, Arg, Asn, Asp, Cys, Glu, Gln Gly, His, Ile Leu, Lys, Met, Phe, Pro, Thr, Trp, Tyr or Val.

19. The pullulanase variant of claim 18, wherein the variant catalytic domain comprises at least two of the following substitutions:
  (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
  (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
  (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
  (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
  (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
  (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

20. The pullulanase variant of claim 18, wherein the variant catalytic domain comprises at least three of the following substitutions:
  (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
  (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
  (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
  (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
  (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
  (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

21. The pullulanase variant of claim 18, wherein the variant catalytic domain comprises at least four of the following substitutions:
  (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
  (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
  (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
  (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
  (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
  (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

22. The pullulanase variant of claim 18, wherein the variant catalytic domain comprises at least five of the following substitutions:
  (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
  (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
  (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
  (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
  (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val,
  (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

23. The pullulanase variant of claim 18, wherein the variant catalytic domain comprises each of the following substitutions:
  (a) a substitution at a position corresponding to position 368 with Ala, Arg, Asp, Cys, Glu, Gln, Gly, His, Ile, Leu, Lys, Met, Phe, Pro, Ser, Thr, Trp, Tyr or Val,
  (b) a substitution at a position corresponding to position 393 with Ala, Arg, Asp, Cyt, Glu, Gln, Gly, His, Ile, Leu, Lys, Met, Phe, Pro, Ser, Thr, Trp, Tyr or Val,
  (c) a substitution at a position corresponding to position 492 with Ala, Arg, Asn, Asp, Cys, Glu, Gln, Gly, His, Ile, Leu, Lys, Met, Phe, Pro, Ser, Trp, Tyr or Val,
  (d) a substitution at a position corresponding to position 610 with Ala, Arg, Asp, Cys, Glu, Gln, Gly, His, Ile, Leu, Lys, Met, Phe, Pro, Ser, Thr, Trp, Tyr or Val,
  (e) a substitution at a position corresponding to position 631 with Ala, Arg, Asn, Asp, Cys, Glu, Gln, Gly, His, Ile, Leu, Lys, Met, Phe, Pro, Ser, Trp, Tyr or Val, (f) a substitution at a position corresponding to position 632 with Ala, Arg, Asn, Asp, Cys, Glu, Gln, Gly, His, Ile, Leu, Lys, Met, Phe, Pro, Thr, Trp, Tyr or Val.

24. The pullulanase variant of claim 18, wherein the catalytic domain has at least 90% sequence identity to amino acids 330 to 828 of SEQ ID NO: 3.

25. The pullulanase variant of claim 18, wherein the catalytic domain has at least 95% sequence identity to amino acids 330 to 828 of SEQ ID NO: 3.

26. A composition comprising a pullulanase variant of claim 18 and one or more enzymes selected from the group consisting of: alpha-amylase, beta-amylase, glucoamylase, and protease.

27. A process of producing a fermentation product, comprising:
(a) liquefying a starch-containing material in the presence of an alpha amylase;
(b) saccharifying the liquefied material in the presence of a glucoamylase; and
(c) fermenting with a fermenting organism; wherein step (a) and/or step (b) is carried out in the presence of a pullulanase variant of claim 18.

28. A process of producing a fermentation product, comprising:
(a) saccharifying a starch-containing material at a temperature below the initial gelatinization temperature of said starch-containing material using at least a glucoamylase, and a pullulanase variant of claim 18; and
(b) fermenting with a fermenting organism.

* * * * *

UNITED STATES PATENT AND TRADEMARK OFFICE
CERTIFICATE OF CORRECTION

PATENT NO. : 10,640,755 B2  
APPLICATION NO. : 16/016950  
DATED : May 5, 2020  
INVENTOR(S) : Matsui et al.

Page 1 of 1

It is certified that error appears in the above-identified patent and that said Letters Patent is hereby corrected as shown below:

In the Claims

In Claim 1, Line 16, delete "Cyt" and replace with --Cys--.

In Claim 2, Line 7, delete "Cyt" and replace with --Cys--.

In Claim 3, Line 7, delete "Cyt" and replace with --Cys--.

In Claim 4, Line 7, delete "Cyt" and replace with --Cys--.

In Claim 5, Line 7, delete "Cyt" and replace with --Cys--.

In Claim 6, Line 7, delete "Cyt" and replace with --Cys--.

In Claim 18, Line 7, after "the variant catalytic domain", insert --has--.

In Claim 18, Line 18, delete "Cyt" and replace with --Cys--.

In Claim 18, Line 31, delete "Ile" and replace with --Ile,--.

In Claim 19, Line 8, delete "Cyt" and replace with --Cys--.

In Claim 20, Line 8, delete "Cyt" and replace with --Cys--.

In Claim 21, Line 8, delete "Cyt" and replace with --Cys--.

In Claim 22, Line 8, delete "Cyt" and replace with --Cys--.

In Claim 23, Line 8, delete "Cyt" and replace with --Cys--.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 28

<210> SEQ ID NO 1
<211> LENGTH: 2586
<212> TYPE: DNA
<213> ORGANISM: Artificial Sequence
<220> FEATURE:

<223> OTHER INFORMATION: Hybrid- Bacillus deramificans and Bacillus
       acidopullulyticus

<400> SEQUENCE: 1

| | | | | | | |
|---|---|---|---|---|---|---|
| atgtccctaa | tacgttctag | gtataatcat | tttgtcattc | ttttactgt | cgccataatg | 60 |
| tttctaacag | tttgtttccc | cgcttataaa | gctttagcag | attctacctc | gacagaagtc | 120 |
| attgtgcatt | atcatcgttt | tgattctaac | tatgcaaatt | gggatctatg | gatgtggcca | 180 |
| tatcaaccag | ttaatggtaa | tggagcagca | tacgagtttt | ctggaaagga | tgattttggc | 240 |
| gttaaagcag | atgttcaagt | gcctggggat | gatacacagg | taggtctgat | tgtccgtaca | 300 |
| aatgattgga | gccaaaaaaa | tacatcagac | gatctccata | ttgatctgac | aaagggggcat | 360 |
| gaaatatgga | ttgttcaggg | ggatcccaat | atttattaca | atctgagtga | tgcgcaggct | 420 |
| gcagcgactc | caaaggtttc | gaatgcgtat | ttggataatg | aaaaaacagt | attggcaaag | 480 |
| ctaactaatc | caatgacatt | atcagatgga | tcaagcggct | ttacggttac | agataaaaca | 540 |
| acagggggaac | aaattccagt | taccgctgca | acaaatgcga | actcagcctc | ctcgtctgag | 600 |
| cagacagact | tggttcaatt | gacgttagcc | agtgcaccgg | atgtttccca | tacaatacaa | 660 |
| gtaggagcag | ccggttatga | agcagtcaat | ctcataccac | gaaatgtatt | aaatttgcct | 720 |
| cgttattatt | acagcggaaa | tgatttaggt | aacgtttatt | caaataaggc | aacggccttc | 780 |
| cgtgtatggg | ctccaactgc | ttcggatgtc | caattacttt | tatacaatag | tgaaacagga | 840 |
| cctgtaacca | aacagcttga | aatgcaaaag | agtgataacg | gtacatggaa | actgaaggtc | 900 |
| cctggtaatc | tgaaaaattg | gtattatctc | tatcaggtaa | cggtgaatgg | gaagacacaa | 960 |
| acagccgttg | acccttatgt | gcgtgctatt | tcagtcaatg | caacacgtgg | tatgatagtc | 1020 |
| gatttagaag | atacgaatcc | tcctggatgg | aaagaagatc | atcaacagac | acctgcgaac | 1080 |
| ccagtggatg | aagtaatcta | cgaagtgcat | gtgcgtgatt | tttcgattga | tgctaattca | 1140 |
| ggcatgaaaa | ataaagggaa | atatcttgcc | tttacagaac | atggcacaaa | aggccctgat | 1200 |
| aacgtgaaaa | cgggtattga | tagtttgaag | gaattaggaa | tcaatgctgt | tcaattacag | 1260 |
| ccgattgaag | aatttaacag | cattgatgaa | acccaaccaa | atatgtataa | ctggggctat | 1320 |
| gacccaagaa | actacaacgt | ccctgaagga | gcgtatgcaa | ctacaccaga | aggaacggct | 1380 |
| cgcattaccc | agttaaagca | actgattcaa | agcattcata | agatcggat | tgctatcaat | 1440 |
| atggatgtgg | tctataacca | tacctttaac | gtaggagtgt | ctgattttga | taagattgtt | 1500 |
| ccgcaatact | attatcggac | agacagcgca | ggtaattata | cgaacggctc | aggtgtaggt | 1560 |
| aatgaaattg | cgaccgagcg | tccgatggtc | caaaagttcg | ttctggattc | tgttaaatat | 1620 |
| tgggtaaagg | aataccatat | cgacggcttc | cgtttcgatc | ttatggctct | tttaggaaaa | 1680 |
| gacaccatgc | caaaatatc | aaaagagctt | catgctatta | atcctggcat | tgtcctgtat | 1740 |
| ggagaaccat | ggactggcgg | tacctctgga | ttatcaagcg | accaactcgt | tacgaaaggt | 1800 |
| cagcaaaagg | gcttgggaat | tggcgtgttt | aatgacaatt | tacgaaacgc | gttgacggc | 1860 |
| aatgtctttg | attcttccgc | tcaaggtttt | gcgacaggtg | caacaggctt | aactgatgca | 1920 |
| attaagaatg | gcgttgaggg | gagtattaat | gactttacct | cttcaccagg | tgagacaatt | 1980 |
| aactatgtca | caagtcatga | taactacacc | ctttgggaca | aaatagccct | aagcaaccct | 2040 |
| aatgattccg | aagcggatcg | gattaaaatg | gatgaactcg | cacaagcagt | tgttatgacc | 2100 |
| tcacaaggtg | ttccattcat | gcaaggcggg | gaagaaatgc | ttcgtacaaa | aggcggcaac | 2160 |
| gacaatagtt | ataatgcagg | cgatacggtc | aatgagtttg | attggagcag | gaaagctcaa | 2220 |

-continued

```
tatccagatg ttttcaacta ttatagcggg ctaatccacc ttcgtcttga tcacccagcc    2280
ttccgcatga cgacagctaa tgaaatcaat agccacctcc aattcctaaa tagtccagag    2340
aacacagtgg cctatgaatt aactgatcat gttaataaag acaaatgggg aaatatcatt    2400
gttgtttata acccaaataa aactgcagca accattaatt tgccgagcgg gaaatgggca    2460
atcaatgcta cgagcggtaa ggtaggagaa tccaccccttg gtcaagcaga gggaagtgtt    2520
caagtcccag gtatatctat gatgatcctt catcaagagg taagcccaga ccacggtaaa    2580
aagtaa                                                               2586
```

<210> SEQ ID NO 2
<211> LENGTH: 861
<212> TYPE: PRT
<213> ORGANISM: Artificial Sequence
<220> FEATURE:
<223> OTHER INFORMATION: Hybrid- Bacillus deramificans and Bacillus
      acidopullulyticus

<400> SEQUENCE: 2

```
Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
            20                  25                  30

Ala Asp Ser Thr Ser Thr Glu Val Ile Val His Tyr His Arg Phe Asp
        35                  40                  45

Ser Asn Tyr Ala Asn Trp Asp Leu Trp Met Trp Pro Tyr Gln Pro Val
    50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu
                85                  90                  95

Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
        115                 120                 125

Pro Asn Ile Tyr Tyr Asn Leu Ser Asp Ala Gln Ala Ala Ala Thr Pro
    130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175

Thr Asp Lys Thr Thr Gly Glu Gln Ile Pro Val Thr Ala Ala Thr Asn
            180                 185                 190

Ala Asn Ser Ala Ser Ser Glu Gln Thr Asp Leu Val Gln Leu Thr
        195                 200                 205

Leu Ala Ser Ala Pro Asp Val Ser His Thr Ile Gln Val Gly Ala Ala
    210                 215                 220

Gly Tyr Glu Ala Val Asn Leu Ile Pro Arg Asn Val Leu Asn Leu Pro
225                 230                 235                 240

Arg Tyr Tyr Tyr Ser Gly Asn Asp Leu Gly Asn Val Tyr Ser Asn Lys
                245                 250                 255

Ala Thr Ala Phe Arg Val Trp Ala Pro Thr Ala Ser Asp Val Gln Leu
            260                 265                 270

Leu Leu Tyr Asn Ser Glu Thr Gly Pro Val Thr Lys Gln Leu Glu Met
        275                 280                 285
```

```
Gln Lys Ser Asp Asn Gly Thr Trp Lys Leu Lys Val Pro Gly Asn Leu
    290                 295                 300

Lys Asn Trp Tyr Tyr Leu Tyr Gln Val Thr Val Asn Gly Lys Thr Gln
305                 310                 315                 320

Thr Ala Val Asp Pro Tyr Val Arg Ala Ile Ser Val Asn Ala Thr Arg
                325                 330                 335

Gly Met Ile Val Asp Leu Glu Asp Thr Asn Pro Pro Gly Trp Lys Glu
            340                 345                 350

Asp His Gln Gln Thr Pro Ala Asn Pro Val Asp Glu Val Ile Tyr Glu
        355                 360                 365

Val His Val Arg Asp Phe Ser Ile Asp Ala Asn Ser Gly Met Lys Asn
    370                 375                 380

Lys Gly Lys Tyr Leu Ala Phe Thr Glu His Gly Thr Lys Gly Pro Asp
385                 390                 395                 400

Asn Val Lys Thr Gly Ile Asp Ser Leu Lys Glu Leu Gly Ile Asn Ala
                405                 410                 415

Val Gln Leu Gln Pro Ile Glu Glu Phe Asn Ser Ile Asp Glu Thr Gln
            420                 425                 430

Pro Asn Met Tyr Asn Trp Gly Tyr Asp Pro Arg Asn Tyr Asn Val Pro
        435                 440                 445

Glu Gly Ala Tyr Ala Thr Thr Pro Glu Gly Thr Ala Arg Ile Thr Gln
    450                 455                 460

Leu Lys Gln Leu Ile Gln Ser Ile His Lys Asp Arg Ile Ala Ile Asn
465                 470                 475                 480

Met Asp Val Val Tyr Asn His Thr Phe Asn Val Gly Val Ser Asp Phe
                485                 490                 495

Asp Lys Ile Val Pro Gln Tyr Tyr Arg Thr Asp Ser Ala Gly Asn
            500                 505                 510

Tyr Thr Asn Gly Ser Gly Val Gly Asn Glu Ile Ala Thr Glu Arg Pro
        515                 520                 525

Met Val Gln Lys Phe Val Leu Asp Ser Val Lys Tyr Trp Val Lys Glu
    530                 535                 540

Tyr His Ile Asp Gly Phe Arg Phe Asp Leu Met Ala Leu Leu Gly Lys
545                 550                 555                 560

Asp Thr Met Ala Lys Ile Ser Lys Glu Leu His Ala Ile Asn Pro Gly
                565                 570                 575

Ile Val Leu Tyr Gly Glu Pro Trp Thr Gly Thr Ser Gly Leu Ser
            580                 585                 590

Ser Asp Gln Leu Val Thr Lys Gly Gln Gln Lys Gly Leu Gly Ile Gly
        595                 600                 605

Val Phe Asn Asp Asn Leu Arg Asn Ala Leu Asp Gly Asn Val Phe Asp
    610                 615                 620

Ser Ser Ala Gln Gly Phe Ala Thr Gly Ala Thr Gly Leu Thr Asp Ala
625                 630                 635                 640

Ile Lys Asn Gly Val Glu Gly Ser Ile Asn Asp Phe Thr Ser Ser Pro
                645                 650                 655

Gly Glu Thr Ile Asn Tyr Val Thr Ser His Asp Asn Tyr Thr Leu Trp
            660                 665                 670

Asp Lys Ile Ala Leu Ser Asn Pro Asn Asp Ser Glu Ala Asp Arg Ile
        675                 680                 685

Lys Met Asp Glu Leu Ala Gln Ala Val Val Met Thr Ser Gln Gly Val
    690                 695                 700

Pro Phe Met Gln Gly Gly Glu Glu Met Leu Arg Thr Lys Gly Gly Asn
```

```
                705                 710                 715                 720
Asp Asn Ser Tyr Asn Ala Gly Asp Thr Val Asn Glu Phe Asp Trp Ser
                    725                 730                 735

Arg Lys Ala Gln Tyr Pro Asp Val Phe Asn Tyr Tyr Ser Gly Leu Ile
                740                 745                 750

His Leu Arg Leu Asp His Pro Ala Phe Arg Met Thr Thr Ala Asn Glu
                755                 760                 765

Ile Asn Ser His Leu Gln Phe Leu Asn Ser Pro Glu Asn Thr Val Ala
            770                 775                 780

Tyr Glu Leu Thr Asp His Val Asn Lys Asp Lys Trp Gly Asn Ile Ile
785                 790                 795                 800

Val Val Tyr Asn Pro Asn Lys Thr Ala Ala Thr Ile Asn Leu Pro Ser
                805                 810                 815

Gly Lys Trp Ala Ile Asn Ala Thr Ser Gly Lys Val Gly Glu Ser Thr
                820                 825                 830

Leu Gly Gln Ala Glu Gly Ser Val Gln Val Pro Gly Ile Ser Met Met
                835                 840                 845

Ile Leu His Gln Glu Val Ser Pro Asp His Gly Lys Lys
                850                 855                 860

<210> SEQ ID NO 3
<211> LENGTH: 828
<212> TYPE: PRT
<213> ORGANISM: Artificial Sequence
<220> FEATURE:
<223> OTHER INFORMATION: Hybrid- Bacillus deramificans and Bacillus
      acidopullulyticus

<400> SEQUENCE: 3

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
                20                  25                  30

Gly Asn Gly Ala Ala Tyr Glu Phe Ser Gly Lys Asp Asp Phe Gly Val
            35                  40                  45

Lys Ala Asp Val Gln Val Pro Gly Asp Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
            115                 120                 125

Thr Asn Pro Met Thr Leu Ser Asp Gly Ser Ser Gly Phe Thr Val Thr
130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
            165                 170                 175

Ala Ser Ala Pro Asp Val Ser His Thr Ile Gln Val Gly Ala Ala Gly
                180                 185                 190

Tyr Glu Ala Val Asn Leu Ile Pro Arg Asn Val Leu Asn Leu Pro Arg
            195                 200                 205
```

-continued

Tyr Tyr Tyr Ser Gly Asn Asp Leu Gly Asn Val Tyr Ser Asn Lys Ala
210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Asn
        355                 360                 365

Val Lys Thr Gly Ile Asp Ser Leu Lys Glu Leu Gly Ile Asn Ala Val
370                 375                 380

Gln Leu Gln Pro Ile Glu Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
        435                 440                 445

Asp Val Val Tyr Asn His Thr Phe Asn Val Gly Val Ser Asp Phe Asp
450                 455                 460

Lys Ile Val Pro Gln Tyr Tyr Arg Thr Asp Ser Ala Gly Asn Tyr
465                 470                 475                 480

Thr Asn Gly Ser Gly Val Gly Asn Glu Ile Ala Thr Glu Arg Pro Met
            485                 490                 495

Val Gln Lys Phe Val Leu Asp Ser Val Lys Tyr Trp Val Lys Glu Tyr
        500                 505                 510

His Ile Asp Gly Phe Arg Phe Asp Leu Met Ala Leu Leu Gly Lys Asp
    515                 520                 525

Thr Met Ala Lys Ile Ser Lys Glu Leu His Ala Ile Asn Pro Gly Ile
530                 535                 540

Val Leu Tyr Gly Glu Pro Trp Thr Gly Gly Thr Ser Gly Leu Ser Ser
545                 550                 555                 560

Asp Gln Leu Val Thr Lys Gly Gln Gln Lys Gly Leu Gly Ile Gly Val
                565                 570                 575

Phe Asn Asp Asn Leu Arg Asn Ala Leu Asp Gly Asn Val Phe Asp Ser
            580                 585                 590

Ser Ala Gln Gly Phe Ala Thr Gly Ala Thr Gly Leu Thr Asp Ala Ile
        595                 600                 605

Lys Asn Gly Val Glu Gly Ser Ile Asn Asp Phe Thr Ser Ser Pro Gly
610                 615                 620

Glu Thr Ile Asn Tyr Val Thr Ser His Asp Asn Tyr Thr Leu Trp Asp

```
                625                630                635                640
        Lys Ile Ala Leu Ser Asn Pro Asn Asp Ser Glu Ala Asp Arg Ile Lys
                            645                650                655

Met Asp Glu Leu Ala Gln Ala Val Val Met Thr Ser Gln Gly Val Pro
                    660                665                670

Phe Met Gln Gly Gly Glu Met Leu Arg Thr Lys Gly Gly Asn Asp
                        675                680                685

Asn Ser Tyr Asn Ala Gly Asp Thr Val Asn Glu Phe Asp Trp Ser Arg
                690                695                700

Lys Ala Gln Tyr Pro Asp Val Phe Asn Tyr Tyr Ser Gly Leu Ile His
        705                710                715                720

Leu Arg Leu Asp His Pro Ala Phe Arg Met Thr Thr Ala Asn Glu Ile
                            725                730                735

Asn Ser His Leu Gln Phe Leu Asn Ser Pro Glu Asn Thr Val Ala Tyr
                        740                745                750

Glu Leu Thr Asp His Val Asn Lys Asp Lys Trp Gly Asn Ile Ile Val
                    755                760                765

Val Tyr Asn Pro Asn Lys Thr Ala Ala Thr Ile Asn Leu Pro Ser Gly
                770                775                780

Lys Trp Ala Ile Asn Ala Thr Ser Gly Lys Val Gly Glu Ser Thr Leu
        785                790                795                800

Gly Gln Ala Glu Gly Ser Val Gln Val Pro Gly Ile Ser Met Met Ile
                            805                810                815

Leu His Gln Glu Val Ser Pro Asp His Gly Lys Lys
                        820                825
```

```
<210> SEQ ID NO 4
<211> LENGTH: 2874
<212> TYPE: DNA
<213> ORGANISM: Bacillus deramificans

<400> SEQUENCE: 4
atggctaaaa aactaattta tgtgtgttta agtgtttgct tagtgttgac ctgggctttt      60
aatgtaaaag gcaatctgc tcatgctgat gggagcacga caacgatcat tgtccactat     120
tttcgccctg ctggtgatta tcaaccttgg agtctatgga tgtggcctga aggagggagt     180
ggagctgaat atgattttaa cgggacagat tcatatgggg aagtcgccaa tgtttccatc     240
ccaggaaacc caagtcaggt aggaattatc gttcgcactc aagattggac caaggatgtg     300
agcgctgacc gctacataga tttaagcaaa ggacatgagg tatggctggt ccaaggaaac     360
agccaaattt tctataatga aaaggatgct gaagatgccg ctaaaccgc tgtaagcaac      420 gcttatttag atgcttcaaa ccaagtttta gttaagctta gccaaccgtt tacactcggt     480
gaaggagcaa gcggcttcac ggttcatgat gacaccgtaa ataaggatat cccagtgaca     540
tctgtgacgg atgcaagtct tggtcaaaat gtaaccgctg ttttggcagg taccttccaa     600 catattttg gaggttccga ttgggcacct gataatcaca gtactttatt aaaaaaggtg      660
aataacaatc tctatcaatt ctcaggagat cttcctgaag gaaactacca atataaagtg     720
gctttaaatg atagctggaa taatccgagt taccttcaa acaatatcga tttaaccgta      780
ccaacaggcg gtgcccatgt cacctttcc tatgtcccct caacgcatgc cgtctacgac      840
agtattaaca accctggcgc cgatttacct gtaaatggca gcggggttaa aacggatctc     900
gtgacggtta ctctagggga agatccagat gtgagccata ctctgtccat tcaaacagat     960
ggctatcaag caaagcaggt gatatctcgt aatgtgcttg attcatcaca gtattactat    1020
```

```
tcaggagatg atcttggaaa tacctataca cataaagcaa ctacctttaa ggtctgggca    1080
cctacttcta ctcaagtaaa tgttcttctt tataatagtg caacgggttc tgtaacaaaa    1140
accgtaccta tgacggcatc gggccatggt gtgtgggaag caacggttaa tcaaaacctt    1200
gaaaattggt attacatgta tgaggtaaca ggccaaggct ctacccgaac ggctgttgat    1260
ccttatgcaa ctgcgattgc accaaatgga acgagaggca tgattgtgga cctggctaaa    1320
acagatcctg ctggctggaa cagtgataaa catattacgc caaagaatat agaagatgag    1380
gtcatctatg aaatggatgt ccgtgacttt tccattgacc ctaattcggg tatgaaaaat    1440
aaagggaagt atttggctct tacagaaaaa ggaacaaagg gccctgacaa cgtaaagacg    1500
gggatagatt ccttaaaaca acttgggatt actcatgttc agcttatgcc tgttttcgca    1560
tttaacagtg tcgatgaaac tgatccaacc caagataatt ggggttatga ccctcgcaac    1620
tatgatgttc ctgaagggca gtatgctaca aatgcgaatg gtacggctcg tataaaagag    1680
tttaaggaaa tggttctttc actccatcgt gaacacattg gggttaacat ggatgttgtc    1740
tataatcata cctttgccac gcaaatctct gacttcgata aaattgtacc agaatattat    1800
taccgtacgg atgatgcagg taattatacc aacggatcag gtactggaaa tgaaatcgca    1860
gccgaaaggc caatggttca aaaatttatt attgattccc ttaagtattg ggtcaatgag    1920
tatcatattg acggcttccg ttttgactta atggcgctgc ttggaaaaga cacgatgtcg    1980
aaagctgcct cggagcttca tgctattaat ccaggaattg cactttacgg tgagccatgg    2040
acgggtggaa cctctgcact gccagaagat cagcttctga caaaaggagc tcaaaaaggc    2100
atgggagtag cggtgtttaa tgacaattta cgaaacgcgt tggacggcaa tgtctttgat    2160
tcttccgctc aaggttttgc gacaggtgca acaggcttaa ctgatgcaat taagaatggc    2220
gttgagggga gtattaatga ctttacctct tcaccaggtg agacaattaa ctatgtcaca    2280
agtcatgata actacaccct ttgggacaaa atagccctaa gcaaccctaa tgattccgaa    2340
gcggatcgga ttaaaatgga tgaactcgca caagcagttg ttatgacctc acaaggtgtt    2400
ccattcatgc aaggcgggga agaaatgctt cgtacaaaag gcggcaacga caatagttat    2460
aatgcaggcg atacggtcaa tgagtttgat tggagcagga agctcaata tccagatgtt    2520 ttcaactatt atagcgggct aatccacctt cgtcttgatc acccagcctt ccgcatgacg    2580
acagctaatg aaatcaatag ccacctccaa ttcctaaata gtccagagaa cacagtggcc    2640
tatgaattaa ctgatcatgt taataaagac aaatggggaa atatcattgt tgtttataac    2700
ccaaataaaa ctgcagcaac cattaatttg ccgagcggga atgggcaat caatgctacg    2760 agcggtaagg taggagaatc cacccttggt caagcagagg gaagtgtcca agtaccaggt    2820
atatctatga tgatccttca tcaagaggta agcccagacc acggtaaaaa gtaa          2874
```

<210> SEQ ID NO 5
<211> LENGTH: 957
<212> TYPE: PRT
<213> ORGANISM: Bacillus deramificans

<400> SEQUENCE: 5

Met Ala Lys Lys Leu Ile Tyr Val Cys Leu Ser Val Cys Leu Val Leu
1               5                   10                  15

Thr Trp Ala Phe Asn Val Lys Gly Gln Ser Ala His Ala Asp Gly Ser
            20                  25                  30

Thr Thr Thr Ile Ile Val His Tyr Phe Arg Pro Ala Gly Asp Tyr Gln
        35                  40                  45

-continued

```
Pro Trp Ser Leu Trp Met Trp Pro Glu Gly Gly Ser Gly Ala Glu Tyr
     50                  55                  60
Asp Phe Asn Gly Thr Asp Ser Tyr Gly Glu Val Ala Asn Val Ser Ile
 65                  70                  75                  80
Pro Gly Asn Pro Ser Gln Val Gly Ile Ile Val Arg Thr Gln Asp Trp
                 85                  90                  95
Thr Lys Asp Val Ser Ala Asp Arg Tyr Ile Asp Leu Ser Lys Gly His
             100                 105                 110
Glu Val Trp Leu Val Gln Gly Asn Ser Gln Ile Phe Tyr Asn Glu Lys
             115                 120                 125
Asp Ala Glu Ala Ala Lys Pro Ala Val Ser Asn Ala Tyr Leu Asp
         130                 135                 140
Ala Ser Asn Gln Val Leu Val Lys Leu Ser Gln Pro Phe Thr Leu Gly
145                 150                 155                 160
Glu Gly Ala Ser Gly Phe Thr Val His Asp Asp Thr Val Asn Lys Asp
                 165                 170                 175
Ile Pro Val Thr Ser Val Thr Asp Ala Ser Leu Gly Gln Asn Val Thr
             180                 185                 190
Ala Val Leu Ala Gly Thr Phe Gln His Ile Phe Gly Ser Asp Trp
         195                 200                 205
Ala Pro Asp Asn His Ser Thr Leu Leu Lys Lys Val Asn Asn Leu
    210                 215                 220
Tyr Gln Phe Ser Gly Asp Leu Pro Glu Gly Asn Tyr Gln Tyr Lys Val
225                 230                 235                 240
Ala Leu Asn Asp Ser Trp Asn Asn Pro Ser Tyr Pro Ser Asn Asn Ile
                 245                 250                 255
Asp Leu Thr Val Pro Thr Gly Gly Ala His Val Thr Phe Ser Tyr Val
             260                 265                 270
Pro Ser Thr His Ala Val Tyr Asp Ser Ile Asn Asn Pro Gly Ala Asp
         275                 280                 285
Leu Pro Val Asn Gly Ser Gly Val Lys Thr Asp Leu Val Thr Val Thr
290                 295                 300
Leu Gly Glu Asp Pro Asp Val Ser His Thr Leu Ser Ile Gln Thr Asp
305                 310                 315                 320
Gly Tyr Gln Ala Lys Gln Val Ile Ser Arg Asn Val Leu Asp Ser Ser
                 325                 330                 335
Gln Tyr Tyr Tyr Ser Gly Asp Asp Leu Gly Asn Thr Tyr Thr His Lys
             340                 345                 350
Ala Thr Thr Phe Lys Val Trp Ala Pro Thr Ser Thr Gln Val Asn Val
         355                 360                 365
Leu Leu Tyr Asn Ser Ala Thr Gly Ser Val Thr Lys Thr Val Pro Met
370                 375                 380
Thr Ala Ser Gly His Gly Val Trp Glu Ala Thr Val Asn Gln Asn Leu
385                 390                 395                 400
Glu Asn Trp Tyr Tyr Met Tyr Glu Val Thr Gly Gln Gly Ser Thr Arg
                 405                 410                 415
Thr Ala Val Asp Pro Tyr Ala Thr Ala Ile Ala Pro Asn Gly Thr Arg
             420                 425                 430
Gly Met Ile Val Asp Leu Ala Lys Thr Asp Pro Ala Gly Trp Asn Ser
         435                 440                 445
Asp Lys His Ile Thr Pro Lys Asn Ile Glu Asp Glu Val Ile Tyr Glu
    450                 455                 460
```

-continued

```
Met Asp Val Arg Asp Phe Ser Ile Asp Pro Asn Ser Gly Met Lys Asn
465                 470                 475                 480

Lys Gly Lys Tyr Leu Ala Leu Thr Glu Lys Gly Thr Lys Gly Pro Asp
            485                 490                 495

Asn Val Lys Thr Gly Ile Asp Ser Leu Lys Gln Leu Gly Ile Thr His
            500                 505                 510

Val Gln Leu Met Pro Val Phe Ala Phe Asn Ser Val Asp Glu Thr Asp
            515                 520                 525

Pro Thr Gln Asp Asn Trp Gly Tyr Asp Pro Arg Asn Tyr Asp Val Pro
            530                 535                 540

Glu Gly Gln Tyr Ala Thr Asn Ala Asn Gly Thr Ala Arg Ile Lys Glu
545                 550                 555                 560

Phe Lys Glu Met Val Leu Ser Leu His Arg Glu His Ile Gly Val Asn
                565                 570                 575

Met Asp Val Val Tyr Asn His Thr Phe Ala Thr Gln Ile Ser Asp Phe
                580                 585                 590

Asp Lys Ile Val Pro Glu Tyr Tyr Tyr Arg Thr Asp Asp Ala Gly Asn
            595                 600                 605

Tyr Thr Asn Gly Ser Gly Thr Gly Asn Glu Ile Ala Ala Glu Arg Pro
            610                 615                 620

Met Val Gln Lys Phe Ile Ile Asp Ser Leu Lys Tyr Trp Val Asn Glu
625                 630                 635                 640

Tyr His Ile Asp Gly Phe Arg Phe Asp Leu Met Ala Leu Leu Gly Lys
                645                 650                 655

Asp Thr Met Ser Lys Ala Ala Ser Glu Leu His Ala Ile Asn Pro Gly
            660                 665                 670

Ile Ala Leu Tyr Gly Glu Pro Trp Thr Gly Gly Thr Ser Ala Leu Pro
            675                 680                 685

Glu Asp Gln Leu Leu Thr Lys Gly Ala Gln Lys Gly Met Gly Val Ala
690                 695                 700

Val Phe Asn Asp Asn Leu Arg Asn Ala Leu Asp Gly Asn Val Phe Asp
705                 710                 715                 720

Ser Ser Ala Gln Gly Phe Ala Thr Gly Ala Thr Gly Leu Thr Asp Ala
            725                 730                 735

Ile Lys Asn Gly Val Glu Gly Ser Ile Asn Asp Phe Thr Ser Ser Pro
            740                 745                 750

Gly Glu Thr Ile Asn Tyr Val Thr Ser His Asp Asn Tyr Thr Leu Trp
            755                 760                 765

Asp Lys Ile Ala Leu Ser Asn Pro Asn Asp Ser Glu Ala Asp Arg Ile
            770                 775                 780

Lys Met Asp Glu Leu Ala Gln Ala Val Val Met Thr Ser Gln Gly Val
785                 790                 795                 800

Pro Phe Met Gln Gly Gly Glu Met Leu Arg Thr Lys Gly Gly Asn
                805                 810                 815

Asp Asn Ser Tyr Asn Ala Gly Asp Thr Val Asn Glu Phe Asp Trp Ser
            820                 825                 830

Arg Lys Ala Gln Tyr Pro Asp Val Phe Asn Tyr Tyr Ser Gly Leu Ile
            835                 840                 845

His Leu Arg Leu Asp His Pro Ala Phe Arg Met Thr Thr Ala Asn Glu
            850                 855                 860

Ile Asn Ser His Leu Gln Phe Leu Asn Ser Pro Glu Asn Thr Val Ala
865                 870                 875                 880

Tyr Glu Leu Thr Asp His Val Asn Lys Asp Lys Trp Gly Asn Ile Ile
```

```
                885                 890                 895
Val Val Tyr Asn Pro Asn Lys Thr Ala Ala Thr Ile Asn Leu Pro Ser
            900                 905                 910

Gly Lys Trp Ala Ile Asn Ala Thr Ser Gly Lys Val Gly Glu Ser Thr
        915                 920                 925

Leu Gly Gln Ala Glu Gly Ser Val Gln Val Pro Gly Ile Ser Met Met
    930                 935                 940

Ile Leu His Gln Glu Val Ser Pro Asp His Gly Lys Lys
945                 950                 955

<210> SEQ ID NO 6
<211> LENGTH: 928
<212> TYPE: PRT
<213> ORGANISM: Bacillus deramifican

<400> SEQUENCE: 6

Asp Gly Ser Thr Thr Ile Ile Val His Tyr Phe Arg Pro Ala Gly
1               5                   10                  15

Asp Tyr Gln Pro Trp Ser Leu Trp Met Trp Pro Glu Gly Gly Ser Gly
            20                  25                  30

Ala Glu Tyr Asp Phe Asn Gly Thr Asp Ser Tyr Gly Glu Val Ala Asn
        35                  40                  45

Val Ser Ile Pro Gly Asn Pro Ser Gln Val Gly Ile Ile Val Arg Thr
    50                  55                  60

Gln Asp Trp Thr Lys Asp Val Ser Ala Asp Arg Tyr Ile Asp Leu Ser
65                  70                  75                  80

Lys Gly His Glu Val Trp Leu Val Gln Gly Asn Ser Gln Ile Phe Tyr
            85                  90                  95

Asn Glu Lys Asp Ala Glu Asp Ala Ala Lys Pro Ala Val Ser Asn Ala
        100                 105                 110

Tyr Leu Asp Ala Ser Asn Gln Val Leu Val Lys Leu Ser Gln Pro Phe
    115                 120                 125

Thr Leu Gly Glu Gly Ala Ser Gly Phe Thr Val His Asp Asp Thr Val
130                 135                 140

Asn Lys Asp Ile Pro Val Thr Ser Val Thr Asp Ala Ser Leu Gly Gln
145                 150                 155                 160

Asn Val Thr Ala Val Leu Ala Gly Thr Phe Gln His Ile Phe Gly Gly
            165                 170                 175

Ser Asp Trp Ala Pro Asp Asn His Ser Thr Leu Leu Lys Lys Val Asn
        180                 185                 190

Asn Asn Leu Tyr Gln Phe Ser Gly Asp Leu Pro Glu Gly Asn Tyr Gln
    195                 200                 205

Tyr Lys Val Ala Leu Asn Asp Ser Trp Asn Asn Pro Ser Tyr Pro Ser
210                 215                 220

Asn Asn Ile Asp Leu Thr Val Pro Thr Gly Gly Ala His Val Thr Phe
225                 230                 235                 240

Ser Tyr Val Pro Ser Thr His Ala Val Tyr Asp Ser Ile Asn Asn Pro
            245                 250                 255

Gly Ala Asp Leu Pro Val Asn Gly Ser Gly Val Lys Thr Asp Leu Val
        260                 265                 270

Thr Val Thr Leu Gly Glu Asp Pro Asp Val Ser His Thr Leu Ser Ile
    275                 280                 285

Gln Thr Asp Gly Tyr Gln Ala Lys Gln Val Ile Ser Arg Asn Val Leu
290                 295                 300
```

```
Asp Ser Ser Gln Tyr Tyr Tyr Ser Gly Asp Asp Leu Gly Asn Thr Tyr
305                 310                 315                 320

Thr His Lys Ala Thr Thr Phe Lys Val Trp Ala Pro Thr Ser Thr Gln
            325                 330                 335

Val Asn Val Leu Leu Tyr Asn Ser Ala Thr Gly Ser Val Thr Lys Thr
                340                 345                 350

Val Pro Met Thr Ala Ser Gly His Gly Val Trp Glu Ala Thr Val Asn
            355                 360                 365

Gln Asn Leu Glu Asn Trp Tyr Tyr Met Tyr Glu Val Thr Gly Gln Gly
    370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
        435                 440                 445

Met Lys Asn Lys Gly Lys Tyr Leu Ala Leu Thr Glu Lys Gly Thr Lys
450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Phe Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Thr Ala Arg
        515                 520                 525

Ile Lys Glu Phe Lys Glu Met Val Leu Ser Leu His Arg Glu His Ile
530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Glu Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
        675                 680                 685

Val Phe Asp Ser Ser Ala Gln Gly Phe Ala Thr Gly Ala Thr Gly Leu
        690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
```

```
              725                 730                 735
Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
            770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
            915                 920                 925

<210> SEQ ID NO 7
<211> LENGTH: 2586
<212> TYPE: DNA
<213> ORGANISM: Bacillus acidopullulyticus

<400> SEQUENCE: 7
atgtccctaa tacgttctag gtataatcat tttgtcattc tttttactgt cgccataatg      60
tttctaacag tttgtttccc cgcttataaa gctttagcag attctacctc gacagaagtc     120
attgtgcatt atcatcgttt tgattctaac tatgcaaatt gggatctatg gatgtggcca     180
tatcaaccag ttaatggtaa tggagcagca tacgagtttt ctggaaagga tgattttggc     240
gttaaagcag atgttcaagt gcctggggat gatacacagg taggtctgat tgtccgtaca     300
aatgattgga gccaaaaaaa tacatcagac gatctcccata ttgatctgac aaaggggcat     360
gaaatatgga ttgttcaggg ggatcccaat atttattaca atctgagtga tgcgcaggct     420
gcagcgactc caaaggtttc gaatgcgtat ttggataatg aaaaaacagt attggcaaag     480
ctaactaatc caatgacatt atcagatgga tcaagcggct ttacggttac agataaaaca     540
acaggggaac aaattccagt taccgctgca acaaatgcga actcagcctc ctcgtctgag     600
cagacagact tggttcaatt gacgttagcc agtgcaccgg atgtttccca tacaatacaa     660
gtaggagcag ccggttatga agcagtcaat ctcataccac gaaatgtatt aaatttgcct     720
cgttattatt acagcggaaa tgatttaggt aacgtttatt caaataaggc aacggccttc     780
cgtgtatggg ctccaactgc ttcggatgtc caattacttt tatacaatag tgaaacagga     840
cctgtaacca aacagcttga aatgcaaaag agtgataacg tacatggaa actgaaggtc     900 cctggtaatc tgaaaaattg gtattatctc tatcaggtaa cggtgaatgg gaagacacaa     960
acagccgttg acccttatgt gcgtgctatt tcagtcaatg caacacgtgg tatgatagtc    1020
```

```
gatttagaag atacgaatcc tcctggatgg aaagaagatc atcaacagac acctgcgaac    1080
ccagtggatg aagtaatcta cgaagtgcat gtgcgtgatt tttcgattga tgctaattca    1140
ggcatgaaaa ataaagggaa atatcttgcc tttacagaac atggcacaaa aggccctgat    1200
aacgtgaaaa cgggtattga tagtttgaag gaattaggaa tcaatgctgt tcaattacag    1260
ccgattgaag aatttaacag cattgatgaa acccaaccaa atatgtataa ctggggctat    1320
gacccaagaa actacaacgt ccctgaagga gcgtatgcaa ctacaccaga aggaacggct    1380
cgcattaccc agttaaagca actgattcaa agcattcata agatcggat  tgctatcaat    1440 atggatgtgg tctataacca tacctttaac gtaggagtgt ctgattttga taagattgtt    1500
ccgcaatact attatcggac agacagcgca ggtaattata cgaacggctc aggtgtaggt    1560
aatgaaattg cgaccgagcg tccgatggtc aaaagttcg  ttctggattc tgttaaatat    1620
tgggtaaagg aataccatat cgacggcttc cgtttcgatc ttatggctct tttaggaaaa    1680
gacaccatgg ccaaaatatc aaaagagctt catgctatta tcctggcat  gtcctgtat     1740 ggagaaccat ggactggcgg tacctctgga ttatcaagcg accaactcgt tacgaaaggt    1800
cagcaaaagg gcttgggaat tggcgtattc aacgataata ttcggaacgg actcgatggt    1860 aacgttttg  ataaatcggc acaaggattt gcaacaggag atccaaacca agttaatgtc    1920
attaaaaatg gagttatggg aagtatttca gatttcactt cggcacctag cgaaaccatt    1980
aactatgtaa caagccatga taatatgaca ttgtgggata aaattagcgc aagtaatccg    2040
aacgatacac aagcagatcg aattaagatg gatgaattgg ctcaagctgt ggtatttact    2100
tcacaagggg taccatttat gcaaggtgga gaagaaatgc tgcggacaaa aggcggtaat    2160
gataatagtt acaatgccgg ggatagcgtg aatcagttcg attggtcaag aaaagcacaa    2220
tttgaaaatg tattcgacta ctattcttgg ttgattcatc tacgtgataa tcacccagca    2280
ttccgtatga cgacagcgga tcaaatcaaa caaaatctca ctttcttgga tagcccaacg    2340
aacactgtag catttgaatt aaaaaatcat gccaatcatg ataaatggaa aacattata     2400 gttatgtata atccaaataa aactgcacaa actctcactc taccaagtgg aaattggaca    2460
attgtaggat taggcaatca agtaggtgag aaatcactag gccatgtaaa tggcacggtt    2520
gaggtgccag ctcttagtac gatcattctt catcagggta catctgaaga tgtcattgat    2580
caaaat                                                                2586
```

<210> SEQ ID NO 8
<211> LENGTH: 862
<212> TYPE: PRT
<213> ORGANISM: Bacillus acidopullulyticus

<400> SEQUENCE: 8

Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
            20                  25                  30

Ala Asp Ser Thr Ser Thr Glu Val Ile Val His Tyr His Arg Phe Asp
        35                  40                  45

Ser Asn Tyr Ala Asn Trp Asp Leu Trp Met Trp Pro Tyr Gln Pro Val
    50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu

```
            85                  90                  95
Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
            115                 120                 125

Pro Asn Ile Tyr Tyr Asn Leu Ser Asp Ala Gln Ala Ala Thr Pro
            130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                    165                 170                 175

Thr Asp Lys Thr Thr Gly Glu Gln Ile Pro Val Thr Ala Ala Thr Asn
            180                 185                 190

Ala Asn Ser Ala Ser Ser Glu Gln Thr Asp Leu Val Gln Leu Thr
            195                 200                 205

Leu Ala Ser Ala Pro Asp Val Ser His Thr Ile Gln Val Gly Ala Ala
210                 215                 220

Gly Tyr Glu Ala Val Asn Leu Ile Pro Arg Asn Val Leu Asn Leu Pro
225                 230                 235                 240

Arg Tyr Tyr Tyr Ser Gly Asn Asp Leu Gly Asn Val Tyr Ser Asn Lys
                    245                 250                 255

Ala Thr Ala Phe Arg Val Trp Ala Pro Thr Ala Ser Asp Val Gln Leu
                    260                 265                 270

Leu Leu Tyr Asn Ser Glu Thr Gly Pro Val Thr Lys Gln Leu Glu Met
                    275                 280                 285

Gln Lys Ser Asp Asn Gly Thr Trp Lys Leu Lys Val Pro Gly Asn Leu
290                 295                 300

Lys Asn Trp Tyr Tyr Leu Tyr Gln Val Thr Val Asn Gly Lys Thr Gln
305                 310                 315                 320

Thr Ala Val Asp Pro Tyr Val Arg Ala Ile Ser Val Asn Ala Thr Arg
                    325                 330                 335

Gly Met Ile Val Asp Leu Glu Asp Thr Asn Pro Pro Gly Trp Lys Glu
                    340                 345                 350

Asp His Gln Gln Thr Pro Ala Asn Pro Val Asp Glu Val Ile Tyr Glu
            355                 360                 365

Val His Val Arg Asp Phe Ser Ile Asp Ala Asn Ser Gly Met Lys Asn
            370                 375                 380

Lys Gly Lys Tyr Leu Ala Phe Thr Glu His Gly Thr Lys Gly Pro Asp
385                 390                 395                 400

Asn Val Lys Thr Gly Ile Asp Ser Leu Lys Glu Leu Gly Ile Asn Ala
                    405                 410                 415

Val Gln Leu Gln Pro Ile Glu Glu Phe Asn Ser Ile Asp Glu Thr Gln
                    420                 425                 430

Pro Asn Met Tyr Asn Trp Gly Tyr Asp Pro Arg Asn Tyr Asn Val Pro
                    435                 440                 445

Glu Gly Ala Tyr Ala Thr Thr Pro Glu Gly Thr Ala Arg Ile Thr Gln
            450                 455                 460

Leu Lys Gln Leu Ile Gln Ser Ile His Lys Asp Arg Ile Ala Ile Asn
465                 470                 475                 480

Met Asp Val Val Tyr Asn His Thr Phe Asn Val Gly Val Ser Asp Phe
                    485                 490                 495

Asp Lys Ile Val Pro Gln Tyr Tyr Arg Thr Asp Ser Ala Gly Asn
                    500                 505                 510
```

Tyr Thr Asn Gly Ser Gly Val Gly Asn Glu Ile Ala Thr Glu Arg Pro
        515                 520                 525

Met Val Gln Lys Phe Val Leu Asp Ser Val Lys Tyr Trp Val Lys Glu
    530                 535                 540

Tyr His Ile Asp Gly Phe Arg Phe Asp Leu Met Ala Leu Leu Gly Lys
545                 550                 555                 560

Asp Thr Met Ala Lys Ile Ser Lys Glu Leu His Ala Ile Asn Pro Gly
                565                 570                 575

Ile Val Leu Tyr Gly Glu Pro Trp Thr Gly Thr Ser Gly Leu Ser
            580                 585                 590

Ser Asp Gln Leu Val Thr Lys Gly Gln Lys Gly Leu Gly Ile Gly
    595                 600                 605

Val Phe Asn Asp Asn Ile Arg Asn Gly Leu Asp Gly Asn Val Phe Asp
    610                 615                 620

Lys Ser Ala Gln Gly Phe Ala Thr Gly Asp Pro Asn Gln Val Asn Val
625                 630                 635                 640

Ile Lys Asn Gly Val Met Gly Ser Ile Ser Asp Phe Thr Ser Ala Pro
                645                 650                 655

Ser Glu Thr Ile Asn Tyr Val Thr Ser His Asp Asn Met Thr Leu Trp
            660                 665                 670

Asp Lys Ile Ser Ala Ser Asn Pro Asn Asp Thr Gln Ala Asp Arg Ile
        675                 680                 685

Lys Met Asp Glu Leu Ala Gln Ala Val Val Phe Thr Ser Gln Gly Val
    690                 695                 700

Pro Phe Met Gln Gly Gly Glu Glu Met Leu Arg Thr Lys Gly Gly Asn
705                 710                 715                 720

Asp Asn Ser Tyr Asn Ala Gly Asp Ser Val Asn Gln Phe Asp Trp Ser
                725                 730                 735

Arg Lys Ala Gln Phe Glu Asn Val Phe Asp Tyr Tyr Ser Trp Leu Ile
            740                 745                 750

His Leu Arg Asp Asn His Pro Ala Phe Arg Met Thr Thr Ala Asp Gln
        755                 760                 765

Ile Lys Gln Asn Leu Thr Phe Leu Asp Ser Pro Thr Asn Thr Val Ala
    770                 775                 780

Phe Glu Leu Lys Asn His Ala Asn His Asp Lys Trp Lys Asn Ile Ile
785                 790                 795                 800

Val Met Tyr Asn Pro Asn Lys Thr Ala Gln Thr Leu Thr Leu Pro Ser
                805                 810                 815

Gly Asn Trp Thr Ile Val Gly Leu Gly Asn Gln Val Gly Glu Lys Ser
            820                 825                 830

Leu Gly His Val Asn Gly Thr Val Glu Val Pro Ala Leu Ser Thr Ile
        835                 840                 845

Ile Leu His Gln Gly Thr Ser Glu Asp Val Ile Asp Gln Asn
    850                 855                 860

<210> SEQ ID NO 9
<211> LENGTH: 829
<212> TYPE: PRT
<213> ORGANISM: Bacillus acidopullulyticus

<400> SEQUENCE: 9

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn

```
                 20                  25                  30
Gly Asn Gly Ala Ala Tyr Glu Phe Ser Gly Lys Asp Asp Phe Gly Val
             35                  40                  45

Lys Ala Asp Val Gln Val Pro Gly Asp Asp Thr Gln Val Gly Leu Ile
 50                  55                  60

Val Arg Thr Asn Asp Trp Ser Gln Lys Asn Thr Ser Asp Asp Leu His
 65                  70                  75                  80

Ile Asp Leu Thr Lys Gly His Glu Ile Trp Ile Val Gln Gly Asp Pro
                 85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
            115                 120                 125

Thr Asn Pro Met Thr Leu Ser Asp Gly Ser Ser Phe Thr Val Thr
            130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
            165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
            195                 200                 205

Tyr Tyr Tyr Ser Gly Asn Asp Leu Gly Asn Val Tyr Ser Asn Lys Ala
            210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
            275                 280                 285

Ala Val Asp Pro Tyr Val Arg Ala Ile Ser Val Asn Ala Thr Arg Gly
            290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
            325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Asn
            355                 360                 365

Val Lys Thr Gly Ile Asp Ser Leu Lys Glu Leu Gly Ile Asn Ala Val
            370                 375                 380

Gln Leu Gln Pro Ile Glu Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
            405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
            435                 440                 445
```

Asp Val Val Tyr Asn His Thr Phe Asn Val Gly Val Ser Asp Phe Asp
450                 455                 460

Lys Ile Val Pro Gln Tyr Tyr Arg Thr Asp Ser Ala Gly Asn Tyr
465                 470                 475                 480

Thr Asn Gly Ser Gly Val Gly Asn Glu Ile Ala Thr Glu Arg Pro Met
                485                 490                 495

Val Gln Lys Phe Val Leu Asp Ser Val Lys Tyr Trp Val Lys Glu Tyr
            500                 505                 510

His Ile Asp Gly Phe Arg Phe Asp Leu Met Ala Leu Leu Gly Lys Asp
                515                 520                 525

Thr Met Ala Lys Ile Ser Lys Glu Leu His Ala Ile Asn Pro Gly Ile
530                 535                 540

Val Leu Tyr Gly Glu Pro Trp Thr Gly Gly Thr Ser Gly Leu Ser Ser
545                 550                 555                 560

Asp Gln Leu Val Thr Lys Gly Gln Gln Lys Gly Leu Gly Ile Gly Val
                565                 570                 575

Phe Asn Asp Asn Ile Arg Asn Gly Leu Asp Gly Asn Val Phe Asp Lys
                580                 585                 590

Ser Ala Gln Gly Phe Ala Thr Gly Asp Pro Asn Gln Val Asn Val Ile
            595                 600                 605

Lys Asn Gly Val Met Gly Ser Ile Ser Asp Phe Thr Ser Ala Pro Ser
610                 615                 620

Glu Thr Ile Asn Tyr Val Thr Ser His Asp Asn Met Thr Leu Trp Asp
625                 630                 635                 640

Lys Ile Ser Ala Ser Asn Pro Asn Asp Thr Gln Ala Asp Arg Ile Lys
                645                 650                 655

Met Asp Glu Leu Ala Gln Ala Val Val Phe Thr Ser Gln Gly Val Pro
                660                 665                 670

Phe Met Gln Gly Gly Glu Glu Met Leu Arg Thr Lys Gly Gly Asn Asp
            675                 680                 685

Asn Ser Tyr Asn Ala Gly Asp Ser Val Asn Gln Phe Asp Trp Ser Arg
690                 695                 700

Lys Ala Gln Phe Glu Asn Val Phe Asp Tyr Tyr Ser Trp Leu Ile His
705                 710                 715                 720

Leu Arg Asp Asn His Pro Ala Phe Arg Met Thr Thr Ala Asp Gln Ile
                725                 730                 735

Lys Gln Asn Leu Thr Phe Leu Asp Ser Pro Thr Asn Thr Val Ala Phe
            740                 745                 750

Glu Leu Lys Asn His Ala Asn His Asp Lys Trp Lys Asn Ile Ile Val
            755                 760                 765

Met Tyr Asn Pro Asn Lys Thr Ala Gln Thr Leu Thr Leu Pro Ser Gly
770                 775                 780

Asn Trp Thr Ile Val Gly Leu Gly Asn Gln Val Gly Glu Lys Ser Leu
785                 790                 795                 800

Gly His Val Asn Gly Thr Val Glu Val Pro Ala Leu Ser Thr Ile Ile
                805                 810                 815

Leu His Gln Gly Thr Ser Glu Asp Val Ile Asp Gln Asn
            820                 825

<210> SEQ ID NO 10
<211> LENGTH: 59
<212> TYPE: DNA
<213> ORGANISM: Artificial Sequence
<220> FEATURE:

<223> OTHER INFORMATION: Primer F1

<400> SEQUENCE: 10
atgtattatg gagctctata aaaatgagga gggaaccgaa tgtccctaat acgttctag    59

<210> SEQ ID NO 11
<211> LENGTH: 37
<212> TYPE: DNA
<213> ORGANISM: Artificial Sequence
<220> FEATURE:
<223> OTHER INFORMATION: Primer R1

<400> SEQUENCE: 11
ttattgatta acgcgtttaa ttttgatcaa tgacatc    37

<210> SEQ ID NO 12
<211> LENGTH: 61
<212> TYPE: DNA
<213> ORGANISM: Artificial Sequence
<220> FEATURE:
<223> OTHER INFORMATION: Primer F2

<400> SEQUENCE: 12
atgtattatg gagctctata aaaatgagga gggaaccgaa tggctaaaaa actaatttat    60
g    61

<210> SEQ ID NO 13
<211> LENGTH: 36
<212> TYPE: DNA
<213> ORGANISM: Artificial Sequence
<220> FEATURE:
<223> OTHER INFORMATION: Primer R2

<400> SEQUENCE: 13
ttattgatta acgcgtttac tttttaccgt ggtctg    36

<210> SEQ ID NO 14
<211> LENGTH: 2760
<212> TYPE: DNA
<213> ORGANISM: Bacillus acidopullulyticus

<400> SEQUENCE: 14
gcttcttcca cagaggtaat tgtccattac caccgttttg acgcgaatta tgcaaattgg    60
gatttgtgga tgtggcccta tcagccggta aatgggaatg gggcggccta tgagttcagc    120
ggaaccgatg aatttggcgt tacggcagat gtccaggttc cagggataaa cacccaggtt    180
gggctaattg tccgaaaaaa cgactggagc cagaaaaata cacctgacga tctccatatt    240
gatctttcaa aggggcatga agtctggatt aaccaggggg atcctaccat ctattacaat    300
ttgaacgacg cggaggcagc agcagtacct gctgtttcca atgcctatct ggacaatgaa    360
aaaactgttc tagcgaaact cagcagcccg atgacattaa cagatggcgc aagcgggttt    420
accgtaaccg atgaaacaac tggagagcaa atcccggtcg tctctgccga atcggcaaac    480
cctgtgactg ctgtccttgt cggggatttc agcaggcat tggggcgtc aggaaattgg    540 tcgccggatg atgatcacac gaagctttca aaaatcaatt ccaaccttta tcaatttaca    600
ggaacgctcc cggcaggtac ctaccaatac aaagtggcat tggaccactc ctggagtgcg    660
tcatacccta taataatgt aaaccttact gtccctgcag gaggtacgaa ggtgacttt    720 acgtatattc cttcaaccca tcaggtgttt gattcgataa acaatccgga tcagacgttt    780
ccttcttcct ccgccggcac ccagtcagat cttgttcagc tgacattggc aagtgcgccc    840

-continued

```
gatatcacgc atgatttgca ggtcgttgca gacggatata aaggaggtaa aattctgccg    900
cggaatgttc tgaacctttc gcgctactat tatagcggca atgacctggg caacgtatat    960
tccaaggatg ccacttcttt cagagtctgg gcgccgactg cttcagatgt agaggtgctt   1020
ttatacaata gtgaaacagg tcctttaact aaacaagtta aaatggaaaa aagcgataat   1080
ggaacatgga agctcgaggt tcccggcaat ctgaaaaatt ggtattatct ctaccaggtg   1140
acggtaaaca gcaagactca aaccgctgtg gatccatatg tcagggcgat tgctgtgaat   1200
gccgcaaggg gaatgatcgt ggatttgact gaaacaaacc ctccagggtg gaacggggac   1260
aagcaggaaa ctccttccaa acctgtggat gaagttattt acgaagcaca tgtaagggac   1320
ttttccatcg acccgaattc cggcatgaag aataaaggaa agtatttagc cttcaccgaa   1380
catggcacta agggccctga tcaagtgaaa acgggtgtcg acagtttgaa ggaattggga   1440
atcaatgctg tccaattgca gcctgtccag gagtttaaca gcattgatga acccagcca    1500 aacacttata actggggata tgatccgagg aactacaatg tcccggaagg agcgtatgcc   1560
acaacgccag agggaacggc gcgcattact gaattaaagc agctggttga aagcctgcac   1620
cgcgacaaaa tagccgtcaa tatggacgtt gtttataatc acaccttcag tacgctcatt   1680
tctgattttg ataagattgt tcctcagtat tattaccgga cagatgatgc gggaaactat   1740
acaaatggct caggggtcgg caatgaattt gcgaccgaac atccgatggc ccggaaattt   1800
gttcttgact ctcttaaata ttgggtgacg caataccaca ttgatggatt ccgcttcgat   1860
ctgatggcgc ttttaggcaa gaatacaatg gcggaagcat cgaaagaact ccatgccatt   1920
aatcctggca tcgtttttata cggggaacca tggacgggcg gcacctcagg aatcacaggt   1980
gaccaattgc tgacaaaagg cgtccaaaaa ggcttgggaa taggagtgtt caatgataat   2040
atccgtaatg gccttgatgg ttctgttttt gatcgggcgg cacaggggtt tgccacaggc   2100
gatcctaatc aggtggatgt catcaaaaat ggcgtaatgg gaagcatcaa cgatttttaca   2160 tcggccccaa gtgaaaccat caactatgta acaagccatg ataatatgac gctttgggat   2220
aaaattacgg caagcaatcc ggatgattct atggctgacc atattaaaat ggacgagctg   2280
gcccaggcgg ttgtcttcac ttcgcagggt gtaccgttta tgcagggcgg ggaagaaatg   2340
ctccggacca agggcggaaa tgacaacagc tataacgccg gagatcaagt caatcaattt   2400
gactggtcaa gaaaagcgca atataaacaa gtgtttgact attacgccgc tttgattcat   2460
ttgcggaatg agcatcctgc cttccgtatg acaactgcag atcaaatcaa ccagcatttg   2520 gcgttttga atagcccgga aaacacggtt gctttcgaac tgaaagatca tgcaaacggc   2580
gataagtgga aaaatatcat cgtgatgtat aacccgaata aaacatccca aacaatcaac   2640
ctgcctgaag ggaattggac aatagaagga ttgggcggcc aatcaggcga aaaatcgctt   2700
ggccttgtgt cagggaaggt ggatgtaccg gccataagta cgatcgttct gaagcaatag   2760
```

<210> SEQ ID NO 15
<211> LENGTH: 919
<212> TYPE: PRT
<213> ORGANISM: Bacillus acidopullulyticus

<400> SEQUENCE: 15

```
Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30
```

-continued

```
Asn Gly Ala Ala Tyr Glu Phe Ser Gly Thr Asp Glu Phe Gly Val Thr
             35                  40                  45
Ala Asp Val Gln Val Pro Gly Asp Asn Thr Gln Val Gly Leu Ile Val
 50                  55                  60
Arg Lys Asn Asp Trp Ser Gln Lys Asn Thr Pro Asp Asp Leu His Ile
 65                  70                  75                  80
Asp Leu Ser Lys Gly His Glu Val Trp Ile Asn Gln Gly Asp Pro Thr
                 85                  90                  95
Ile Tyr Tyr Asn Leu Asn Asp Ala Glu Ala Ala Val Pro Ala Val
                100                 105                 110
Ser Asn Ala Tyr Leu Asp Asn Glu Lys Thr Val Leu Ala Lys Leu Ser
                115                 120                 125
Ser Pro Met Thr Leu Thr Asp Gly Ala Ser Gly Phe Thr Val Thr Asp
                130                 135                 140
Glu Thr Thr Gly Glu Gln Ile Pro Val Val Ser Ala Glu Ser Ala Asn
145                 150                 155                 160
Pro Val Thr Ala Val Leu Val Gly Asp Phe Gln Gln Ala Leu Gly Ala
                165                 170                 175
Ser Gly Asn Trp Ser Pro Asp Asp His Thr Lys Leu Ser Lys Ile
                180                 185                 190
Asn Ser Asn Leu Tyr Gln Phe Thr Gly Thr Leu Pro Ala Gly Thr Tyr
                195                 200                 205
Gln Tyr Lys Val Ala Leu Asp His Ser Trp Ser Ala Ser Tyr Pro Asn
                210                 215                 220
Asn Asn Val Asn Leu Thr Val Pro Ala Gly Gly Thr Lys Val Thr Phe
225                 230                 235                 240
Thr Tyr Ile Pro Ser Thr His Gln Val Phe Asp Ser Ile Asn Asn Pro
                245                 250                 255
Asp Gln Thr Phe Pro Ser Ser Ala Gly Thr Gln Ser Asp Leu Val
                260                 265                 270
Gln Leu Thr Leu Ala Ser Ala Pro Asp Ile Thr His Asp Leu Gln Val
                275                 280                 285
Val Ala Asp Gly Tyr Lys Gly Gly Lys Ile Leu Pro Arg Asn Val Leu
                290                 295                 300
Asn Leu Ser Arg Tyr Tyr Tyr Ser Gly Asn Asp Leu Gly Asn Val Tyr
305                 310                 315                 320
Ser Lys Asp Ala Thr Ser Phe Arg Val Trp Ala Pro Thr Ala Ser Asp
                325                 330                 335
Val Glu Val Leu Leu Tyr Asn Ser Glu Thr Gly Pro Leu Thr Lys Gln
                340                 345                 350
Val Lys Met Glu Lys Ser Asp Asn Gly Thr Trp Lys Leu Glu Val Pro
                355                 360                 365
Gly Asn Leu Lys Asn Trp Tyr Tyr Leu Tyr Gln Val Thr Val Asn Ser
                370                 375                 380
Lys Thr Gln Thr Ala Val Asp Pro Tyr Val Arg Ala Ile Ala Val Asn
385                 390                 395                 400
Ala Ala Arg Gly Met Ile Val Asp Leu Thr Glu Thr Asn Pro Pro Gly
                405                 410                 415
Trp Asn Gly Asp Lys Gln Glu Thr Pro Ser Lys Pro Val Asp Glu Val
                420                 425                 430
Ile Tyr Glu Ala His Val Arg Asp Phe Ser Ile Asp Pro Asn Ser Gly
                435                 440                 445
Met Lys Asn Lys Gly Lys Tyr Leu Ala Phe Thr Glu His Gly Thr Lys
```

```
            450                 455                 460
Gly Pro Asp Gln Val Lys Thr Gly Val Asp Ser Leu Lys Glu Leu Gly
465                 470                 475                 480

Ile Asn Ala Val Gln Leu Gln Pro Val Gln Glu Phe Asn Ser Ile Asp
                485                 490                 495

Glu Thr Gln Pro Asn Thr Tyr Asn Trp Gly Tyr Asp Pro Arg Asn Tyr
                500                 505                 510

Asn Val Pro Glu Gly Ala Tyr Ala Thr Thr Pro Glu Gly Thr Ala Arg
                515                 520                 525

Ile Thr Glu Leu Lys Gln Leu Val Glu Ser Leu His Arg Asp Lys Ile
                530                 535                 540

Ala Val Asn Met Asp Val Val Tyr Asn His Thr Phe Ser Thr Leu Ile
545                 550                 555                 560

Ser Asp Phe Asp Lys Ile Val Pro Gln Tyr Tyr Arg Thr Asp Asp
                565                 570                 575

Ala Gly Asn Tyr Thr Asn Gly Ser Gly Val Gly Asn Glu Phe Ala Thr
                580                 585                 590

Glu His Pro Met Ala Arg Lys Phe Val Leu Asp Ser Leu Lys Tyr Trp
                595                 600                 605

Val Thr Gln Tyr His Ile Asp Gly Phe Arg Phe Asp Leu Met Ala Leu
                610                 615                 620

Leu Gly Lys Asn Thr Met Ala Glu Ala Ser Lys Glu Leu His Ala Ile
625                 630                 635                 640

Asn Pro Gly Ile Val Leu Tyr Gly Glu Pro Trp Thr Gly Gly Thr Ser
                645                 650                 655

Gly Ile Thr Gly Asp Gln Leu Leu Thr Lys Gly Val Gln Lys Gly Leu
                660                 665                 670

Gly Ile Gly Val Phe Asn Asp Asn Ile Arg Asn Gly Leu Asp Gly Ser
                675                 680                 685

Val Phe Asp Arg Ala Ala Gln Gly Phe Ala Thr Gly Asp Pro Asn Gln
690                 695                 700

Val Asp Val Ile Lys Asn Gly Val Met Gly Ser Ile Asn Asp Phe Thr
705                 710                 715                 720

Ser Ala Pro Ser Glu Thr Ile Asn Tyr Val Thr Ser His Asp Asn Met
                725                 730                 735

Thr Leu Trp Asp Lys Ile Thr Ala Ser Asn Pro Asp Asp Ser Met Ala
                740                 745                 750

Asp His Ile Lys Met Asp Glu Leu Ala Gln Ala Val Val Phe Thr Ser
                755                 760                 765

Gln Gly Val Pro Phe Met Gln Gly Gly Glu Glu Met Leu Arg Thr Lys
                770                 775                 780

Gly Gly Asn Asp Asn Ser Tyr Asn Ala Gly Asp Gln Val Asn Gln Phe
785                 790                 795                 800

Asp Trp Ser Arg Lys Ala Gln Tyr Lys Gln Val Phe Asp Tyr Tyr Ala
                805                 810                 815

Ala Leu Ile His Leu Arg Asn Glu His Pro Ala Phe Arg Met Thr Thr
                820                 825                 830

Ala Asp Gln Ile Asn Gln His Leu Ala Phe Leu Asn Ser Pro Glu Asn
                835                 840                 845

Thr Val Ala Phe Glu Leu Lys Asp His Ala Asn Gly Asp Lys Trp Lys
                850                 855                 860

Asn Ile Ile Val Met Tyr Asn Pro Asn Lys Thr Ser Gln Thr Ile Asn
865                 870                 875                 880
```

Leu Pro Glu Gly Asn Trp Thr Ile Glu Gly Leu Gly Gly Gln Ser Gly
                885                 890                 895

Glu Lys Ser Leu Gly Leu Val Ser Gly Lys Val Asp Val Pro Ala Ile
            900                 905                 910

Ser Thr Ile Val Leu Lys Gln
        915

<210> SEQ ID NO 16
<211> LENGTH: 928
<212> TYPE: PRT
<213> ORGANISM: Artificial
<220> FEATURE:
<223> OTHER INFORMATION: Hybrid pullulanase

<400> SEQUENCE: 16

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
    50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
            115                 120                 125

Ser Pro Met Thr Leu Thr Asp Gly Ala Ser Gly Phe Thr Val Thr Asp
        130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
        195                 200                 205

Gln Tyr Lys Val Ala Leu Asp His Ser Trp Ser Ala Ser Tyr Pro Asn
    210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
            260                 265                 270

Gln Leu Thr Leu Ala Ser Ala Pro Asp Ile Thr His Asp Leu Gln Val
        275                 280                 285

Val Ala Asp Gly Tyr Lys Gly Gly Lys Ile Leu Pro Arg Asn Val Leu
    290                 295                 300

Asn Leu Pro Arg Tyr Tyr Tyr Ser Gly Asn Asp Leu Gly Asn Val Tyr
305                 310                 315                 320

```
Ser Asn Lys Ala Thr Ala Phe Arg Val Trp Ala Pro Thr Ala Ser Asp
            325                 330                 335

Val Gln Leu Leu Leu Tyr Asn Ser Glu Thr Gly Pro Val Thr Lys Gln
                340                 345                 350

Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
        370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
                420                 425                 430

Ile Tyr Glu Val His Val Arg Asp Phe Ser Ile Asp Ala Asn Ser Gly
                435                 440                 445

Met Lys Asn Lys Gly Lys Tyr Leu Ala Phe Thr Glu His Gly Thr Lys
            450                 455                 460

Gly Pro Asp Asn Val Lys Thr Gly Ile Asp Ser Leu Lys Glu Leu Gly
465                 470                 475                 480

Ile Asn Ala Val Gln Leu Gln Pro Ile Glu Glu Phe Asn Ser Ile Asp
                485                 490                 495

Glu Thr Gln Pro Asn Met Tyr Asn Trp Gly Tyr Asp Pro Arg Asn Tyr
                500                 505                 510

Asn Val Pro Glu Gly Ala Tyr Ala Thr Thr Pro Glu Gly Thr Ala Arg
                515                 520                 525

Ile Thr Gln Leu Lys Gln Leu Ile Gln Ser Ile His Lys Asp Arg Ile
            530                 535                 540

Ala Ile Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
                580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Glu Asp Gln Leu Leu Thr Lys Gly Ala Gln Lys Gly Met
                660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
                725                 730                 735
```

```
Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Glu Glu Met Leu Arg Thr Lys
770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
            915                 920                 925

<210> SEQ ID NO 17
<211> LENGTH: 928
<212> TYPE: PRT
<213> ORGANISM: Artificial
<220> FEATURE:
<223> OTHER INFORMATION: Hybrid pullulanase

<400> SEQUENCE: 17

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
            85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
        115                 120                 125

Ser Pro Met Thr Leu Thr Asp Gly Ala Ser Gly Phe Thr Val Thr Asp
    130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
            165                 170                 175
```

-continued

Ser Gly Asn Trp Ser Pro Asp Asp His Thr Lys Leu Ser Lys Ile
            180             185             190

Asn Ser Asn Leu Tyr Gln Phe Thr Gly Thr Leu Pro Ala Gly Thr Tyr
195             200             205

Gln Tyr Lys Val Ala Leu Asp His Ser Trp Ser Ala Ser Tyr Pro Asn
    210             215             220

Asn Asn Val Asn Leu Thr Val Pro Ala Gly Gly Thr Lys Val Thr Phe
225             230             235             240

Thr Tyr Ile Pro Ser Thr His Gln Val Phe Asp Ser Ile Asn Asn Pro
            245             250             255

Asp Gln Thr Phe Pro Ser Ser Ala Gly Thr Gln Ser Asp Leu Val
    260             265             270

Gln Leu Thr Leu Ala Ser Ala Pro Asp Ile Thr His Asp Leu Gln Val
        275             280             285

Val Ala Asp Gly Tyr Lys Gly Gly Lys Ile Leu Pro Arg Asn Val Leu
    290             295             300

Asn Leu Pro Arg Tyr Tyr Tyr Ser Gly Asn Asp Leu Gly Asn Val Tyr
305             310             315             320

Ser Asn Lys Ala Thr Ala Phe Arg Val Trp Ala Pro Thr Ala Ser Asp
            325             330             335

Val Gln Leu Leu Leu Tyr Asn Ser Glu Thr Gly Pro Val Thr Lys Gln
        340             345             350

Leu Glu Met Gln Lys Ser Asp Asn Gly Thr Trp Lys Leu Lys Val Pro
            355             360             365

Gly Asn Leu Lys Asn Trp Tyr Tyr Leu Tyr Gln Val Thr Val Asn Gly
    370             375             380

Lys Thr Gln Thr Ala Val Asp Pro Tyr Val Arg Ala Ile Ser Val Asn
385             390             395             400

Ala Thr Arg Gly Met Ile Val Asp Leu Glu Asp Thr Asn Pro Pro Gly
            405             410             415

Trp Lys Glu Asp His Gln Gln Thr Pro Ala Asn Pro Val Asp Glu Val
        420             425             430

Ile Tyr Glu Val His Val Arg Asp Phe Ser Ile Asp Ala Asn Ser Gly
    435             440             445

Met Lys Asn Lys Gly Lys Tyr Leu Ala Phe Thr Glu His Gly Thr Lys
450             455             460

Gly Pro Asp Asn Val Lys Thr Gly Ile Asp Ser Leu Lys Glu Leu Gly
465             470             475             480

Ile Asn Ala Val Gln Leu Gln Pro Ile Glu Glu Phe Asn Ser Ile Asp
            485             490             495

Glu Thr Gln Pro Asn Met Tyr Asn Trp Gly Tyr Asp Pro Arg Asn Tyr
        500             505             510

Asn Val Pro Glu Gly Ala Tyr Ala Thr Thr Pro Glu Gly Thr Ala Arg
    515             520             525

Ile Thr Gln Leu Lys Gln Leu Ile Gln Ser Ile His Lys Asp Arg Ile
    530             535             540

Ala Ile Asn Met Asp Val Val Tyr Asn His Thr Phe Ser Thr Leu Ile
545             550             555             560

Ser Asp Phe Asp Lys Ile Val Pro Gln Tyr Tyr Arg Thr Asp Asp
            565             570             575

Ala Gly Asn Tyr Thr Asn Gly Ser Gly Val Gly Asn Glu Phe Ala Thr
        580             585             590

Glu His Pro Met Ala Arg Lys Phe Val Leu Asp Ser Leu Lys Tyr Trp

Val Thr Gln Tyr His Ile Asp Gly Phe Arg Phe Asp Leu Met Ala Leu
    610             615                 620
Leu Gly Lys Asn Thr Met Ala Glu Ala Ser Lys Glu Leu His Ala Ile
625                 630                 635                 640
Asn Pro Gly Ile Val Leu Tyr Gly Glu Pro Trp Thr Gly Gly Thr Ser
                645                 650                 655
Gly Ile Thr Gly Asp Gln Leu Leu Thr Lys Gly Val Gln Lys Gly Leu
            660                 665                 670
Gly Ile Gly Val Phe Asn Asp Asn Leu Arg Asn Ala Leu Asp Gly Asn
        675                 680                 685
Val Phe Asp Ser Ser Ala Gln Gly Phe Ala Thr Gly Ala Thr Gly Leu
    690                 695                 700
Thr Asp Ala Ile Lys Asn Gly Val Glu Gly Ser Ile Asn Asp Phe Thr
705                 710                 715                 720
Ser Ser Pro Asn Glu Thr Ile Asn Tyr Val Thr Ser His Asp Asn Tyr
                725                 730                 735
Thr Leu Trp Asp Lys Ile Ala Leu Ser Asn Pro Asn Asp Ser Glu Ala
            740                 745                 750
Asp Arg Ile Lys Met Asp Glu Leu Ala Gln Ala Val Val Met Thr Ser
        755                 760                 765
Gln Gly Val Pro Phe Met Gln Gly Gly Glu Glu Met Leu Arg Thr Lys
    770                 775                 780
Gly Gly Asn Asp Asn Ser Tyr Asn Ala Gly Asp Thr Val Asn Glu Phe
785                 790                 795                 800
Asp Trp Ser Arg Lys Ala Gln Tyr Pro Asp Val Phe Asn Tyr Tyr Ser
                805                 810                 815
Gly Leu Ile His Leu Arg Leu Asp His Pro Ala Phe Arg Met Thr Thr
            820                 825                 830
Ala Asn Glu Ile Asn Ser His Leu Gln Phe Leu Asn Ser Pro Glu Asn
        835                 840                 845
Thr Val Ala Tyr Glu Leu Thr Asp His Val Asn Lys Asp Lys Trp Gly
    850                 855                 860
Asn Ile Ile Val Val Tyr Asn Pro Asn Lys Thr Ala Ala Thr Ile Asn
865                 870                 875                 880
Leu Pro Ser Gly Lys Trp Ala Ile Asn Ala Thr Ser Gly Lys Val Gly
                885                 890                 895
Glu Ser Thr Leu Gly Gln Ala Glu Gly Ser Val Gln Val Pro Gly Ile
            900                 905                 910
Ser Met Met Ile Leu His Gln Glu Val Ser Pro Asp His Gly Lys Lys
        915                 920                 925

<210> SEQ ID NO 18
<211> LENGTH: 2586
<212> TYPE: DNA
<213> ORGANISM: Artificial
<220> FEATURE:
<223> OTHER INFORMATION: Hybrid pullulanase

<400> SEQUENCE: 18
atgtccctaa tacgttctag gtataatcat tttgtcattc tttttactgt cgccataatg     60
tttctaacag tttgtttccc cgcttataaa gctttagcag attctacctc gacagaagtc    120
attgtgcatt atcatcgttt tgattctaac tatgcaaatt gggatctatg gatgtggcca    180
tatcaaccag ttaatggtaa tggagcagca tacgagtttt ctggaaagga tgattttggc    240

```
gttaaagcag atgttcaagt gcctggggat gatacacagg taggtctgat tgtccgtaca    300
aatgattgga gccaaaaaaa tacatcagac gatctccata ttgatctgac aaagggcat     360 gaaatatgga ttgttcaggg ggatcccaat atttattaca atctgagtga tgcgcaggct    420
gcagcgactc caaaggtttc gaatgcgtat ttggataatg aaaaaacagt attggcaaag    480
ctaactaatc caatgacatt atcagatgga tcaagcggct ttacggttac agataaaaca    540 acagggaac aaattccagt taccgctgca acaaatgcga actcagcctc ctcgtctgag     600
cagacagact tggttcaatt gacgttagcc agtgcaccgg atgtttccca tacaatacaa    660
gtaggagcag ccggttatga agcagtcaat ctcataccac gtaatgtgct tgattcatca    720
cagtattact attcaggaga tgatcttgga aatacctata cacataaagc aactacccttt   780 aaggtctggg cacctacttc tactcaagta aatgttcttc tttataatag tgcaacgggt    840
tctgtaacaa aaccgtacc tatgacggca tcgggccatg gtgtgtggga agcaacggtt     900
aatcaaaacc ttgaaaattg gtattacatg tatgaggtaa caggccaagg ctctacccga    960
acggctgttg atccttatgc aactgcgatt gcaccaaatg gaacgagagg catgattgtg    1020
gacctggcta aaacagatcc tgctggctgg aacagtgata acatattac gccaaagaat     1080 atagaagatg aggtcatcta tgaaatggat gtccgtgact tttccattga ccctaattcg    1140
ggtatgaaaa ataaagggaa gtatttggct cttacagaaa aaggaacaaa gggccctgac    1200
aacgtaaaga cggggataga ttccttaaaa caacttggga ttactcatgt tcagcttatg    1260
cctgttttcg catttaacag tgtcgatgaa actgatccaa cccaagataa ttggggttat    1320
gaccctcgca actatgatgt tcctgaaggg cagtatgcta caaatgcgaa tggtacggct    1380
cgtataaaag agtttaagga aatggttctt tcactccatc gtgaacacat tggggttaac    1440
atggatgttg tctataatca tacctttgcc acgcaaatct ctgacttcga taaaattgta    1500
ccagaatatt attaccgtac ggatgatgca ggtaattata ccaacggatc aggtactgga    1560
aatgaaatcg cagccgaaag gccaatggtt caaaaattta ttattgattc ccttaagtat    1620
tgggtcaatg agtatcatat tgacggcttc cgttttgact taatggcgct gcttggaaaa    1680
gacacgatgt cgaaagctgc ctcggagctt catgctatta atccaggaat tgcactttac    1740
ggtgagccat ggacgggtgg aacctctgca ctgccagaag atcagcttct gacaaaagga    1800
gctcaaaaag gcatgggagt agcggtgttt aatgacaatt tacgaaacgc gttggacggc    1860
aatgtctttg attcttccgc tcaaggtttt gcgacaggtg caacaggctt aactgatgca    1920
attaagaatg gcgttgaggg gagtattaat gactttacct cttcaccagg tgagacaatt    1980
aactatgtca caagtcatga taactacacc ctttgggaca aaatagccct aagcaaccct    2040
aatgattccg aagcggatcg gattaaaatg gatgaactcg cacaagcagt tgttatgacc    2100
tcacaaggtg ttccattcat gcaaggcggg gaagaaatgc ttcgtacaaa aggcggcaac    2160
gacaatagtt ataatgcagg cgatacggtc aatgagtttg attggagcag gaaagctcaa    2220
tatccagatg ttttcaacta ttatagcggg ctaatccacc ttcgtcttga tcacccagcc    2280
ttccgcatga cgacagctaa tgaaatcaat agccacctcc aattcctaaa tagtccagag    2340
aacacagtgg cctatgaatt aactgatcat gttaataaag acaaatgggg aaatatcatt    2400
gttgtttata acccaaataa aactgcagca accattaatt tgccgagcgg gaaatgggca    2460
atcaatgcta cgagcggtaa ggtaggagaa tccacccttg gtcaagcaga gggaagtgtc    2520
caagtaccag gtatatctat gatgatcctt catcaagagg taagcccaga ccacggtaaa    2580
``` aagtaa 2586

<210> SEQ ID NO 19
<211> LENGTH: 861
<212> TYPE: PRT
<213> ORGANISM: Artificial
<220> FEATURE:
<223> OTHER INFORMATION: Hybrid pullulanase

<400> SEQUENCE: 19

```
Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
            20                  25                  30

Ala Asp Ser Thr Ser Thr Glu Val Ile Val His Tyr His Arg Phe Asp
        35                  40                  45

Ser Asn Tyr Ala Asn Trp Asp Leu Trp Met Trp Pro Tyr Gln Pro Val
    50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu
                85                  90                  95

Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
        115                 120                 125

Pro Asn Ile Tyr Tyr Asn Leu Ser Asp Ala Gln Ala Ala Thr Pro
    130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175

Thr Asp Lys Thr Thr Gly Glu Gln Ile Pro Val Thr Ala Ala Thr Asn
            180                 185                 190

Ala Asn Ser Ala Ser Ser Ser Glu Gln Thr Asp Leu Val Gln Leu Thr
        195                 200                 205

Leu Ala Ser Ala Pro Asp Val Ser His Thr Ile Gln Val Gly Ala Ala
    210                 215                 220

Gly Tyr Glu Ala Val Asn Leu Ile Pro Arg Asn Val Leu Asp Ser Ser
225                 230                 235                 240

Gln Tyr Tyr Tyr Ser Gly Asp Asp Leu Gly Asn Thr Tyr Thr His Lys
                245                 250                 255

Ala Thr Thr Phe Lys Val Trp Ala Pro Thr Ser Thr Gln Val Asn Val
            260                 265                 270

Leu Leu Tyr Asn Ser Ala Thr Gly Ser Val Thr Lys Thr Val Pro Met
        275                 280                 285

Thr Ala Ser Gly His Gly Val Trp Glu Ala Thr Val Asn Gln Asn Leu
    290                 295                 300

Glu Asn Trp Tyr Tyr Met Tyr Glu Val Thr Gly Gln Gly Ser Thr Arg
305                 310                 315                 320

Thr Ala Val Asp Pro Tyr Ala Thr Ala Ile Ala Pro Asn Gly Thr Arg
                325                 330                 335

Gly Met Ile Val Asp Leu Ala Lys Thr Asp Pro Ala Gly Trp Asn Ser
            340                 345                 350

Asp Lys His Ile Thr Pro Lys Asn Ile Glu Asp Glu Val Ile Tyr Glu
```

-continued

```
            355                 360                 365
Met Asp Val Arg Asp Phe Ser Ile Asp Pro Asn Ser Gly Met Lys Asn
370                 375                 380
Lys Gly Lys Tyr Leu Ala Leu Thr Glu Lys Gly Thr Lys Gly Pro Asp
385                 390                 395                 400
Asn Val Lys Thr Gly Ile Asp Ser Leu Lys Gln Leu Gly Ile Thr His
                    405                 410                 415
Val Gln Leu Met Pro Val Phe Ala Phe Asn Ser Val Asp Glu Thr Asp
                420                 425                 430
Pro Thr Gln Asp Asn Trp Gly Tyr Asp Pro Arg Asn Tyr Asp Val Pro
            435                 440                 445
Glu Gly Gln Tyr Ala Thr Asn Ala Asn Gly Thr Ala Arg Ile Lys Glu
        450                 455                 460
Phe Lys Glu Met Val Leu Ser Leu His Arg His Ile Gly Val Asn
465                 470                 475                 480
Met Asp Val Val Tyr Asn His Thr Phe Ala Thr Gln Ile Ser Asp Phe
                485                 490                 495
Asp Lys Ile Val Pro Glu Tyr Tyr Arg Thr Asp Asp Ala Gly Asn
                500                 505                 510
Tyr Thr Asn Gly Ser Gly Thr Gly Asn Glu Ile Ala Ala Glu Arg Pro
            515                 520                 525
Met Val Gln Lys Phe Ile Ile Asp Ser Leu Lys Tyr Trp Val Asn Glu
        530                 535                 540
Tyr His Ile Asp Gly Phe Arg Phe Asp Leu Met Ala Leu Leu Gly Lys
545                 550                 555                 560
Asp Thr Met Ser Lys Ala Ala Ser Glu Leu His Ala Ile Asn Pro Gly
                565                 570                 575
Ile Ala Leu Tyr Gly Glu Pro Trp Thr Gly Thr Ser Ala Leu Pro
                580                 585                 590
Glu Asp Gln Leu Leu Thr Lys Gly Ala Gln Lys Gly Met Gly Val Ala
            595                 600                 605
Val Phe Asn Asp Asn Leu Arg Asn Ala Leu Asp Gly Asn Val Phe Asp
        610                 615                 620
Ser Ser Ala Gln Gly Phe Ala Thr Gly Ala Thr Gly Leu Thr Asp Ala
625                 630                 635                 640
Ile Lys Asn Gly Val Glu Gly Ser Ile Asn Asp Phe Thr Ser Ser Pro
                645                 650                 655
Gly Glu Thr Ile Asn Tyr Val Thr Ser His Asp Asn Tyr Thr Leu Trp
                660                 665                 670
Asp Lys Ile Ala Leu Ser Asn Pro Asn Asp Ser Glu Ala Asp Arg Ile
            675                 680                 685
Lys Met Asp Glu Leu Ala Gln Ala Val Val Met Thr Ser Gln Gly Val
        690                 695                 700
Pro Phe Met Gln Gly Gly Glu Glu Met Leu Arg Thr Lys Gly Gly Asn
705                 710                 715                 720
Asp Asn Ser Tyr Asn Ala Gly Asp Thr Val Asn Glu Phe Asp Trp Ser
                725                 730                 735
Arg Lys Ala Gln Tyr Pro Asp Val Phe Asn Tyr Ser Gly Leu Ile
                740                 745                 750
His Leu Arg Leu Asp His Pro Ala Phe Arg Met Thr Thr Ala Asn Glu
            755                 760                 765
Ile Asn Ser His Leu Gln Phe Leu Asn Ser Pro Glu Asn Thr Val Ala
        770                 775                 780
```

```
Tyr Glu Leu Thr Asp His Val Asn Lys Asp Lys Trp Gly Asn Ile Ile
785                 790                 795                 800

Val Val Tyr Asn Pro Asn Lys Thr Ala Ala Thr Ile Asn Leu Pro Ser
                805                 810                 815

Gly Lys Trp Ala Ile Asn Ala Ser Gly Lys Val Gly Glu Ser Thr
            820                 825                 830

Leu Gly Gln Ala Glu Gly Ser Val Gln Val Pro Gly Ile Ser Met Met
            835                 840                 845

Ile Leu His Gln Glu Val Ser Pro Asp His Gly Lys Lys
        850                 855                 860

<210> SEQ ID NO 20
<211> LENGTH: 928
<212> TYPE: PRT
<213> ORGANISM: Artificial
<220> FEATURE:
<223> OTHER INFORMATION: Hybrid pullulanase

<400> SEQUENCE: 20

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
    50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
        115                 120                 125

Ser Pro Met Thr Leu Thr Asp Gly Ala Ser Gly Phe Thr Val Thr Asp
    130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
        195                 200                 205

Gln Tyr Lys Val Ala Leu Asp His Ser Trp Ser Ala Ser Tyr Pro Asn
    210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
            260                 265                 270

Gln Leu Thr Leu Ala Ser Ala Pro Asp Ile Thr His Asp Leu Gln Val
        275                 280                 285
```

```
Val Ala Asp Gly Tyr Lys Gly Lys Ile Leu Pro Arg Asn Val Leu
        290                 295                 300

Asn Leu Pro Arg Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
                340                 345                 350

Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
        370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
                420                 425                 430

Ile Tyr Glu Val His Val Arg Asp Phe Ser Ile Asp Ala Asn Ser Gly
            435                 440                 445

Met Lys Asn Lys Gly Lys Tyr Leu Ala Phe Thr Glu His Gly Thr Lys
        450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
                485                 490                 495

Glu Thr Gln Pro Asn Met Tyr Asn Trp Gly Tyr Asp Pro Arg Asn Tyr
            500                 505                 510

Asn Val Pro Glu Gly Ala Tyr Ala Thr Thr Pro Glu Gly Thr Ala Arg
        515                 520                 525

Ile Thr Gln Leu Lys Gln Leu Ile Gln Ser Ile His Lys Asp Arg Ile
        530                 535                 540

Ala Ile Asn Met Asp Val Val Tyr Asn His Thr Phe Ser Thr Leu Ile
545                 550                 555                 560

Ser Asp Phe Asp Lys Ile Val Pro Gln Tyr Tyr Tyr Arg Thr Asp Asp
                565                 570                 575

Ala Gly Asn Tyr Thr Asn Gly Ser Gly Val Gly Asn Glu Phe Ala Thr
                580                 585                 590

Glu His Pro Met Ala Arg Lys Phe Val Leu Asp Ser Leu Lys Tyr Trp
            595                 600                 605

Val Thr Gln Tyr His Ile Asp Gly Phe Arg Phe Asp Leu Met Ala Leu
        610                 615                 620

Leu Gly Lys Asn Thr Met Ala Glu Ala Ser Lys Glu Leu His Ala Ile
625                 630                 635                 640

Asn Pro Gly Ile Val Leu Tyr Gly Glu Pro Trp Thr Gly Gly Thr Ser
                645                 650                 655

Gly Ile Thr Gly Asp Gln Leu Leu Thr Lys Gly Val Gln Lys Gly Leu
                660                 665                 670

Gly Ile Gly Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
        690                 695                 700
```

```
Thr Asp Ala Ile Lys Arg Gly Val Glu Gly Ser Ile Asn Asp Phe Thr
705                 710                 715                 720

Ser Ser Pro Ser Glu Thr Ile Asn Tyr Val Ser Cys His Asp Asn Tyr
            725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
        770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
    850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
        900                 905                 910

Ser Met Met Ile Leu His Gln Glu Val Ser Pro Asp His Gly Lys Lys
        915                 920                 925

<210> SEQ ID NO 21
<211> LENGTH: 828
<212> TYPE: PRT
<213> ORGANISM: Artificial
<220> FEATURE:
<223> OTHER INFORMATION: Hybrid pullulanase

<400> SEQUENCE: 21

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
            85                  90                  95

Asn Ile Tyr Tyr Asn Leu Ser Asp Ala Gln Ala Ala Thr Pro Lys
        100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140
```

```
Asp Lys Thr Thr Gly Glu Gln Ile Pro Val Thr Ala Ala Thr Asn Ala
145                 150                 155                 160
Asn Ser Ala Ser Ser Ser Glu Gln Thr Asp Leu Val Gln Leu Thr Leu
                165                 170                 175
Ala Ser Ala Pro Asp Val Ser His Thr Ile Gln Val Gly Ala Ala Gly
            180                 185                 190
Tyr Glu Ala Val Asn Leu Ile Pro Arg Asn Val Leu Asp Ser Ser Gln
        195                 200                 205
Tyr Tyr Tyr Ser Gly Asp Asp Leu Gly Asn Thr Tyr Thr His Lys Ala
    210                 215                 220
Thr Thr Phe Lys Val Trp Ala Pro Thr Ser Thr Gln Val Asn Val Leu
225                 230                 235                 240
Leu Tyr Asn Ser Ala Thr Gly Ser Val Thr Lys Thr Val Pro Met Thr
                245                 250                 255
Ala Ser Gly His Gly Val Trp Glu Ala Thr Val Asn Gln Asn Leu Glu
            260                 265                 270
Asn Trp Tyr Tyr Met Tyr Glu Val Thr Gly Gln Gly Ser Thr Arg Thr
        275                 280                 285
Ala Val Asp Pro Tyr Ala Thr Ala Ile Ala Pro Asn Gly Thr Arg Gly
    290                 295                 300
Met Ile Val Asp Leu Ala Lys Thr Asp Pro Ala Gly Trp Asn Ser Asp
305                 310                 315                 320
Lys His Ile Thr Pro Lys Asn Ile Glu Asp Glu Val Ile Tyr Glu Met
                325                 330                 335
Asp Val Arg Asp Phe Ser Ile Asp Pro Asn Ser Gly Met Lys Asn Lys
            340                 345                 350
Gly Lys Tyr Leu Ala Leu Thr Glu Lys Gly Thr Lys Gly Pro Asp Gly
        355                 360                 365
Val Lys Thr Gly Ile Asp Ser Leu Lys Gln Leu Gly Ile Thr His Val
    370                 375                 380
Gln Leu Met Pro Val Phe Ala Phe Ala Ser Val Asp Glu Thr Asp Pro
385                 390                 395                 400
Thr Gln Asp Asn Trp Gly Tyr Asp Pro Arg Asn Tyr Asp Val Pro Glu
                405                 410                 415
Gly Gln Tyr Ala Thr Asn Ala Asn Gly Thr Ala Arg Ile Lys Glu Phe
            420                 425                 430
Lys Glu Met Val Leu Ser Leu His Arg Glu His Ile Gly Val Asn Met
        435                 440                 445
Asp Val Val Tyr Asn His Thr Phe Ala Thr Gln Ile Ser Asp Phe Asp
450                 455                 460
Lys Ile Val Pro Glu Tyr Tyr Tyr Arg Thr Asp Asp Ala Gly Asn Tyr
465                 470                 475                 480
Thr Asn Gly Ser Gly Thr Gly Asn Glu Ile Ala Ser Glu Arg Pro Met
                485                 490                 495
Val Gln Lys Phe Ile Ile Asp Ser Leu Lys Tyr Trp Val Asn Glu Tyr
            500                 505                 510
His Ile Asp Gly Phe Arg Phe Asp Leu Met Ala Leu Leu Gly Lys Asp
        515                 520                 525
Thr Met Ser Lys Ala Ala Ser Glu Leu His Ala Ile Asn Pro Gly Ile
    530                 535                 540
Ala Leu Tyr Gly Glu Pro Trp Thr Gly Gly Thr Ser Ala Leu Pro Glu
545                 550                 555                 560
Asp Gln Leu Leu Thr Lys Gly Ala Gln Lys Gly Met Gly Val Ala Val
```

```
            565                 570                 575
Phe Asn Asp Asn Leu Arg Asn Ala Leu Asp Gly Asn Val Phe Asp Ser
            580                 585                 590

Ser Ala Gln Gly Phe Ala Thr Gly Ala Thr Gly Leu Thr Asp Ala Ile
            595                 600                 605

Lys Asn Gly Val Glu Gly Ser Ile Asn Asp Phe Thr Ser Ser Pro Gly
            610                 615                 620

Glu Thr Ile Asn Tyr Val Thr Ser His Asp Asn Tyr Thr Leu Trp Asp
625                 630                 635                 640

Lys Ile Ala Leu Ser Asn Pro Asn Asp Ser Glu Ala Asp Arg Ile Lys
                    645                 650                 655

Met Asp Glu Leu Ala Gln Ala Val Val Met Thr Ser Gln Gly Val Pro
            660                 665                 670

Phe Met Gln Gly Gly Glu Glu Met Leu Arg Thr Lys Gly Gly Asn Asp
            675                 680                 685

Asn Ser Tyr Asn Ala Gly Asp Thr Val Asn Glu Phe Asp Trp Ser Arg
            690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                    725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
            755                 760                 765

Val Tyr Asn Pro Asn Lys Thr Ala Ala Thr Ile Asn Leu Pro Ser Gly
            770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
            805                 810                 815

Leu His Gln Glu Val Ser Pro Asp His Gly Lys Lys
            820                 825

<210> SEQ ID NO 22
<211> LENGTH: 928
<212> TYPE: PRT
<213> ORGANISM: Artificial
<220> FEATURE:
<223> OTHER INFORMATION: Hybrid pullulanase

<400> SEQUENCE: 22

Asp Gly Ser Thr Thr Thr Ile Ile Val His Tyr Phe Arg Pro Ala Gly
1               5                   10                  15

Asp Tyr Gln Pro Trp Ser Leu Trp Met Trp Pro Glu Gly Gly Ser Gly
            20                  25                  30

Ala Glu Tyr Asp Phe Asn Gly Thr Asp Ser Tyr Gly Glu Val Ala Asn
            35                  40                  45

Val Ser Ile Pro Gly Asn Pro Ser Gln Val Gly Ile Ile Val Arg Thr
        50                  55                  60

Gln Asp Trp Thr Lys Asp Val Ser Ala Asp Arg Tyr Ile Asp Leu Ser
65              70                  75                  80

Lys Gly His Glu Val Trp Leu Val Gln Gly Asn Ser Gln Ile Phe Tyr
                85                  90                  95

Asn Glu Lys Asp Ala Glu Asp Ala Ala Lys Pro Ala Val Ser Asn Ala
```

```
                100             105                 110
Tyr Leu Asp Ala Ser Asn Gln Val Leu Val Lys Leu Ser Gln Pro Phe
            115                 120                 125
Thr Leu Gly Glu Gly Ala Ser Gly Phe Thr Val His Asp Thr Val
        130                 135                 140
Asn Lys Asp Ile Pro Val Thr Ser Val Thr Asp Ala Ser Leu Gly Gln
145                 150                 155                 160
Asn Val Thr Ala Val Leu Ala Gly Thr Phe Gln His Ile Phe Gly Gly
                165                 170                 175
Ser Asp Trp Ala Pro Asp Asn His Ser Thr Leu Leu Lys Lys Val Asn
            180                 185                 190
Asn Asn Leu Tyr Gln Phe Ser Gly Asp Leu Pro Glu Gly Asn Tyr Gln
        195                 200                 205
Tyr Lys Val Ala Leu Asn Asp Ser Trp Asn Asn Pro Ser Tyr Pro Ser
        210                 215                 220
Asn Asn Ile Asp Leu Thr Val Pro Thr Gly Gly Ala His Val Thr Phe
225                 230                 235                 240
Ser Tyr Val Pro Ser Thr His Ala Val Tyr Asp Ser Ile Asn Asn Pro
                245                 250                 255
Gly Ala Asp Leu Pro Val Asn Gly Ser Gly Val Lys Thr Asp Leu Val
            260                 265                 270
Thr Val Thr Leu Gly Glu Asp Pro Asp Val Ser His Thr Leu Ser Ile
        275                 280                 285
Gln Thr Asp Gly Tyr Gln Ala Lys Gln Val Ile Ser Arg Asn Val Leu
        290                 295                 300
Asp Ser Ser Gln Tyr Tyr Tyr Ser Gly Asp Asp Leu Gly Asn Thr Tyr
305                 310                 315                 320
Thr His Lys Ala Thr Thr Phe Lys Val Trp Ala Pro Thr Ser Thr Gln
                325                 330                 335
Val Asn Val Leu Leu Tyr Asn Ser Ala Thr Gly Ser Val Thr Lys Thr
            340                 345                 350
Val Pro Met Thr Ala Ser Gly His Gly Val Trp Glu Ala Thr Val Asn
        355                 360                 365
Gln Asn Leu Glu Asn Trp Tyr Tyr Met Tyr Glu Val Thr Gly Gln Gly
        370                 375                 380
Ser Thr Arg Thr Ala Val Asp Pro Tyr Ala Thr Ala Ile Ala Pro Asn
385                 390                 395                 400
Gly Thr Arg Gly Met Ile Val Asp Leu Ala Lys Thr Asp Pro Ala Gly
                405                 410                 415
Trp Asn Ser Asp Lys His Ile Thr Pro Lys Asn Ile Glu Asp Glu Val
            420                 425                 430
Ile Tyr Glu Met Asp Val Arg Asp Phe Ser Ile Asp Pro Asn Ser Gly
        435                 440                 445
Met Lys Asn Lys Gly Lys Tyr Leu Ala Leu Thr Glu Lys Gly Thr Lys
        450                 455                 460
Gly Pro Asp Gly Val Lys Thr Gly Ile Asp Ser Leu Lys Gln Leu Gly
465                 470                 475                 480
Ile Thr His Val Gln Leu Met Pro Val Phe Ala Phe Ala Ser Val Asp
                485                 490                 495
Glu Thr Asp Pro Thr Gln Asp Asn Trp Gly Tyr Asp Pro Arg Asn Tyr
            500                 505                 510
Asp Val Pro Glu Gly Gln Tyr Ala Thr Asn Ala Asn Gly Thr Ala Arg
        515                 520                 525
```

```
Ile Lys Glu Phe Lys Glu Met Val Leu Ser Leu His Arg Glu His Ile
    530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
                580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Glu Asp Gln Leu Leu Thr Lys Gly Ala Gln Lys Gly Met
                660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
690                 695                 700

Thr Asp Ala Ile Lys Arg Gly Val Glu Gly Ser Ile Asn Asp Phe Thr
705                 710                 715                 720

Ser Ser Pro Ser Glu Thr Ile Asn Tyr Val Thr Ser His Asp Asn Tyr
                725                 730                 735

Thr Leu Trp Asp Lys Ile Ala Leu Ser Asn Pro Asn Asp Ser Glu Ala
                740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
                820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
                900                 905                 910

Ser Met Met Ile Leu His Gln Glu Val Ser Pro Asp His Gly Lys Lys
            915                 920                 925

<210> SEQ ID NO 23
<211> LENGTH: 828
```

```
<212> TYPE: PRT
<213> ORGANISM: Artificial
<220> FEATURE:
<223> OTHER INFORMATION: Hybrid pullulanase

<400> SEQUENCE: 23
```

| | | | | | | | | | | | | | | |
|---|---|---|---|---|---|---|---|---|---|---|---|---|---|---|
| Asp | Ser | Thr | Ser | Thr | Glu | Val | Ile | Val | His | Tyr | His | Arg | Phe | Asp | Ser |
| 1 | | | | 5 | | | | | 10 | | | | | 15 |

Asn Tyr Ala Asn Trp Asp Leu Trp Met Trp Pro Tyr Gln Pro Val Asn
            20               25             30

Gly Asn Gly Ala Ala Tyr Glu Phe Ser Gly Lys Asp Asp Phe Gly Val
        35             40             45

Lys Ala Asp Val Gln Val Pro Gly Asp Asp Thr Gln Val Gly Leu Ile
 50                55             60

Val Arg Thr Asn Asp Trp Ser Gln Lys Asn Thr Ser Asp Asp Leu His
 65               70              75             80

Ile Asp Leu Thr Lys Gly His Glu Ile Trp Ile Val Gln Gly Asp Pro
            85             90            95

Asn Ile Tyr Tyr Asn Leu Ser Asp Ala Gln Ala Ala Thr Pro Lys
        100           105           110

Val Ser Asn Ala Tyr Leu Asp Asn Glu Lys Thr Val Leu Ala Lys Leu
        115           120           125

Thr Asn Pro Met Thr Leu Ser Asp Gly Ser Ser Gly Phe Thr Val Thr
130               135              140

Asp Lys Thr Thr Gly Glu Gln Ile Pro Val Thr Ala Ala Thr Asn Ala
145               150             155           160

Asn Ser Ala Ser Ser Ser Glu Gln Thr Asp Leu Val Gln Leu Thr Leu
        165           170           175

Ala Ser Ala Pro Asp Val Ser His Thr Ile Gln Val Gly Ala Ala Gly
        180           185           190

Tyr Glu Ala Val Asn Leu Ile Pro Arg Asn Val Leu Asp Ser Ser Gln
        195           200           205

Tyr Tyr Tyr Ser Gly Asp Asp Leu Gly Asn Thr Tyr Thr His Lys Ala
210               215             220

Thr Thr Phe Lys Val Trp Ala Pro Thr Ser Thr Gln Val Asn Val Leu
225               230             235           240

Leu Tyr Asn Ser Ala Thr Gly Ser Val Thr Lys Thr Val Pro Met Thr
        245           250           255

Ala Ser Gly His Gly Val Trp Glu Ala Thr Val Asn Gln Asn Leu Glu
        260           265           270

Asn Trp Tyr Tyr Met Tyr Glu Val Thr Gly Gln Gly Ser Thr Arg Thr
        275           280           285

Ala Val Asp Pro Tyr Ala Thr Ala Ile Ala Pro Asn Gly Thr Arg Gly
        290           295           300

Met Ile Val Asp Leu Ala Lys Thr Asp Pro Ala Gly Trp Asn Ser Asp
305               310             315           320

Lys His Ile Thr Pro Lys Asn Ile Glu Asp Val Ile Tyr Glu Met
        325           330           335

Asp Val Arg Asp Phe Ser Ile Asp Pro Asn Ser Gly Met Lys Asn Lys
        340           345           350

Gly Lys Tyr Leu Ala Leu Thr Glu Lys Gly Thr Lys Gly Pro Asp Gly
        355           360           365

Val Lys Thr Gly Ile Asp Ser Leu Lys Gln Leu Gly Ile Thr His Val
        370           375           380

```
Gln Leu Met Pro Val Phe Ala Phe Ala Ser Val Asp Glu Thr Asp Pro
385                 390                 395                 400

Thr Gln Asp Asn Trp Gly Tyr Asp Pro Arg Asn Tyr Asp Val Pro Glu
            405                 410                 415

Gly Gln Tyr Ala Thr Asn Ala Asn Gly Thr Ala Arg Ile Lys Glu Phe
            420                 425                 430

Lys Glu Met Val Leu Ser Leu His Arg Glu His Ile Gly Val Asn Met
            435                 440                 445

Asp Val Val Tyr Asn His Thr Phe Ala Thr Gln Ile Ser Asp Phe Asp
            450                 455                 460

Lys Ile Val Pro Glu Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
                485                 490                 495

Val Gln Lys Phe Ile Ile Asp Ser Leu Lys Tyr Trp Val Asn Glu Tyr
                500                 505                 510

His Ile Asp Gly Phe Arg Phe Asp Leu Met Ala Leu Leu Gly Lys Asp
            515                 520                 525

Thr Met Ser Lys Ala Ala Ser Glu Leu His Ala Ile Asn Pro Gly Ile
            530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
                565                 570                 575

Phe Asn Asp Asn Leu Arg Asn Ala Leu Asp Gly Asn Val Phe Asp Ser
                580                 585                 590

Ser Ala Gln Gly Phe Ala Thr Gly Ala Thr Gly Leu Thr Asp Ala Ile
            595                 600                 605

Lys Arg Gly Val Glu Gly Ser Ile Asn Asp Phe Thr Ser Ser Pro Ser
610                 615                 620

Glu Thr Ile Asn Tyr Val Thr Ser His Asp Asn Tyr Thr Leu Trp Asp
625                 630                 635                 640

Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
            660                 665                 670

Phe Met Gln Gly Gly Glu Glu Met Leu Arg Thr Lys Gly Gly Asn Asp
            675                 680                 685

Asn Ser Tyr Asn Ala Gly Asp Thr Val Asn Glu Phe Asp Trp Ser Arg
            690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
            755                 760                 765

Val Tyr Asn Pro Asn Lys Thr Ala Thr Ile Asn Leu Pro Ser Gly
            770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
```

```
                    805                 810                 815
Leu His Gln Glu Val Ser Pro Asp His Gly Lys Lys
                820                 825

<210> SEQ ID NO 24
<211> LENGTH: 928
<212> TYPE: PRT
<213> ORGANISM: Artificial
<220> FEATURE:
<223> OTHER INFORMATION: Hybrid pullulanase

<400> SEQUENCE: 24

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
    50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
        115                 120                 125

Ser Pro Met Thr Leu Thr Asp Gly Ala Ser Gly Phe Thr Val Thr Asp
    130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
        195                 200                 205

Gln Tyr Lys Val Ala Leu Asp His Ser Trp Ser Ala Ser Tyr Pro Asn
    210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
            260                 265                 270

Gln Leu Thr Leu Ala Ser Ala Pro Asp Ile Thr His Asp Leu Gln Val
        275                 280                 285

Val Ala Asp Gly Tyr Lys Gly Gly Lys Ile Leu Pro Arg Asn Val Leu
    290                 295                 300

Asn Leu Pro Arg Tyr Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
```

```
                    340                 345                 350
Leu Glu Met Gln Lys Ser Asp Asn Gly Thr Trp Lys Leu Lys Val Pro
            355                 360                 365
Gly Asn Leu Lys Asn Trp Tyr Tyr Leu Tyr Gln Val Thr Val Asn Gly
        370                 375                 380
Lys Thr Gln Thr Ala Val Asp Pro Tyr Val Arg Ala Ile Ser Val Asn
385                 390                 395                 400
Ala Thr Arg Gly Met Ile Val Asp Leu Glu Asp Thr Asn Pro Pro Gly
                405                 410                 415
Trp Lys Glu Asp His Gln Gln Thr Pro Ala Asn Pro Val Asp Glu Val
            420                 425                 430
Ile Tyr Glu Val His Val Arg Asp Phe Ser Ile Asp Ala Asn Ser Gly
        435                 440                 445
Met Lys Asn Lys Gly Lys Tyr Leu Ala Phe Thr Glu His Gly Thr Lys
    450                 455                 460
Gly Pro Asp Gly Val Lys Thr Gly Ile Asp Ser Leu Lys Glu Leu Gly
465                 470                 475                 480
Ile Asn Ala Val Gln Leu Gln Pro Ile Glu Glu Phe Ala Ser Ile Asp
                485                 490                 495
Glu Thr Gln Pro Asn Met Tyr Asn Trp Gly Tyr Asp Pro Arg Asn Tyr
            500                 505                 510
Asn Val Pro Glu Gly Ala Tyr Ala Thr Thr Pro Glu Gly Thr Ala Arg
        515                 520                 525
Ile Thr Gln Leu Lys Gln Leu Ile Gln Ser Ile His Lys Asp Arg Ile
    530                 535                 540
Ala Ile Asn Met Asp Val Val Tyr Asn His Thr Phe Asn Val Gly Val
545                 550                 555                 560
Ser Asp Phe Asp Lys Ile Val Pro Gln Tyr Tyr Arg Thr Asp Ser
                565                 570                 575
Ala Gly Asn Tyr Thr Asn Gly Ser Gly Val Gly Asn Glu Ile Ala Ser
            580                 585                 590
Glu Arg Pro Met Val Gln Lys Phe Val Leu Asp Ser Val Lys Tyr Trp
        595                 600                 605
Val Lys Glu Tyr His Ile Asp Gly Phe Arg Phe Asp Leu Met Ala Leu
    610                 615                 620
Leu Gly Lys Asp Thr Met Ala Lys Ile Ser Lys Glu Leu His Ala Ile
625                 630                 635                 640
Asn Pro Gly Ile Val Leu Tyr Gly Glu Pro Trp Thr Gly Gly Thr Ser
                645                 650                 655
Gly Leu Ser Ser Asp Gln Leu Val Thr Lys Gly Gln Gln Lys Gly Leu
            660                 665                 670
Gly Ile Gly Val Phe Asn Asp Asn Leu Arg Asn Ala Leu Asp Gly Asn
        675                 680                 685
Val Phe Asp Ser Ser Ala Gln Gly Phe Ala Thr Gly Ala Thr Gly Leu
    690                 695                 700
Thr Asp Ala Ile Lys Arg Gly Val Glu Gly Ser Ile Asn Asp Phe Thr
705                 710                 715                 720
Ser Ser Pro Ser Glu Thr Ile Asn Tyr Val Ser Cys His Asp Asn Tyr
                725                 730                 735
Thr Leu Trp Asp Lys Ile Ala Leu Ser Asn Pro Asn Asp Ser Glu Ala
            740                 745                 750
Asp Arg Ile Lys Met Asp Glu Leu Ala Gln Ala Val Val Met Thr Ser
        755                 760                 765
```

```
Gln Gly Val Pro Phe Met Gln Gly Gly Glu Met Leu Arg Thr Lys
            770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
            915                 920                 925

<210> SEQ ID NO 25
<211> LENGTH: 928
<212> TYPE: PRT
<213> ORGANISM: Artificial
<220> FEATURE:
<223> OTHER INFORMATION: Hybrid pullulanase

<400> SEQUENCE: 25

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
    50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
            115                 120                 125

Ser Pro Met Thr Leu Thr Asp Gly Ala Ser Gly Phe Thr Val Thr Asp
        130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
            195                 200                 205
```

-continued

```
Gln Tyr Lys Val Ala Leu Asp His Ser Trp Ser Ala Ser Tyr Pro Asn
        210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
            260                 265                 270

Gln Leu Thr Leu Ala Ser Ala Pro Asp Ile Thr His Asp Leu Gln Val
        275                 280                 285

Val Ala Asp Gly Tyr Lys Gly Gly Lys Ile Leu Pro Arg Asn Val Leu
290                 295                 300

Asn Leu Pro Arg Tyr Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
            340                 345                 350

Leu Glu Met Gln Lys Ser Asp Asn Gly Thr Trp Lys Leu Lys Val Pro
        355                 360                 365

Gly Asn Leu Lys Asn Trp Tyr Tyr Leu Tyr Gln Val Thr Val Asn Gly
370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
            420                 425                 430

Ile Tyr Glu Val His Val Arg Asp Phe Ser Ile Asp Ala Asn Ser Gly
        435                 440                 445

Met Lys Asn Lys Gly Lys Tyr Leu Ala Phe Thr Glu His Gly Thr Lys
450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
                485                 490                 495

Glu Thr Gln Pro Asn Met Tyr Asn Trp Gly Tyr Asp Pro Arg Asn Tyr
            500                 505                 510

Asn Val Pro Glu Gly Ala Tyr Ala Thr Thr Pro Glu Gly Thr Ala Arg
        515                 520                 525

Ile Thr Gln Leu Lys Gln Leu Ile Gln Ser Ile His Lys Asp Arg Ile
530                 535                 540

Ala Ile Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
610                 615                 620
```

```
Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
            645                 650                 655

Ala Leu Pro Glu Asp Gln Leu Leu Thr Lys Gly Ala Gln Lys Gly Met
        660                 665                 670

Gly Val Ala Val Phe Asn Asp Asn Leu Arg Asn Ala Leu Asp Gly Asn
                675                 680                 685

Val Phe Asp Ser Ser Ala Gln Gly Phe Ala Thr Gly Ala Thr Gly Leu
690                 695                 700

Thr Asp Ala Ile Lys Arg Gly Val Gly Gly Ser Ile Asn Asp Phe Thr
705                 710                 715                 720

Ser Ser Pro Ser Glu Thr Ile Asn Tyr Val Ser Cys His Asp Asn Tyr
            725                 730                 735

Thr Leu Trp Asp Lys Ile Ala Leu Ser Asn Pro Asn Asp Ser Glu Ala
        740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
        820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
        900                 905                 910

Ser Met Met Ile Leu His Gln Glu Val Ser Pro Asp His Gly Lys Lys
            915                 920                 925

<210> SEQ ID NO 26
<211> LENGTH: 928
<212> TYPE: PRT
<213> ORGANISM: Artificial
<220> FEATURE:
<223> OTHER INFORMATION: Hybrid pullulanase

<400> SEQUENCE: 26

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
50                  55                  60
```

```
Arg Lys Asn Asp Trp Ser Gln Lys Asn Thr Pro Asp Asp Leu His Ile
 65                  70                  75                  80

Asp Leu Ser Lys Gly His Glu Val Trp Ile Asn Gln Gly Asp Pro Thr
                 85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
            115                 120                 125

Ser Pro Met Thr Leu Thr Asp Gly Ala Ser Gly Phe Thr Val Thr Asp
            130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
            195                 200                 205

Gln Tyr Lys Val Ala Leu Asp His Ser Trp Ser Ala Ser Tyr Pro Asn
            210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
                260                 265                 270

Gln Leu Thr Leu Ala Ser Ala Pro Asp Ile Thr His Asp Leu Gln Val
            275                 280                 285

Val Ala Asp Gly Tyr Lys Gly Gly Lys Ile Leu Pro Arg Asn Val Leu
            290                 295                 300

Asn Leu Pro Arg Tyr Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
            325                 330                 335

Val Gln Leu Leu Leu Tyr Asn Ser Glu Thr Gly Pro Val Thr Lys Gln
            340                 345                 350

Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
                420                 425                 430

Ile Tyr Glu Val His Val Arg Asp Phe Ser Ile Asp Ala Asn Ser Gly
            435                 440                 445

Met Lys Asn Lys Gly Lys Tyr Leu Ala Phe Thr Glu His Gly Thr Lys
            450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
```

```
            485                 490                 495
Glu Thr Gln Pro Asn Met Tyr Asn Trp Gly Tyr Asp Pro Arg Asn Tyr
            500                 505                 510

Asn Val Pro Glu Gly Ala Tyr Ala Thr Thr Pro Glu Gly Thr Ala Arg
            515                 520                 525

Ile Thr Glu Phe Lys Gln Leu Ile Gln Ser Ile His Lys Asp Arg Ile
            530                 535                 540

Ala Ile Asn Met Asp Val Val Tyr Asn His Thr Phe Ser Thr Leu Ile
545                 550                 555                 560

Ser Asp Phe Asp Lys Ile Val Pro Gln Tyr Tyr Tyr Arg Thr Asp Asp
            565                 570                 575

Ala Gly Asn Tyr Thr Asn Gly Ser Gly Val Gly Asn Glu Phe Ala Thr
            580                 585                 590

Glu His Pro Met Ala Arg Lys Phe Val Leu Asp Ser Leu Lys Tyr Trp
            595                 600                 605

Val Thr Gln Tyr His Ile Asp Gly Phe Arg Phe Asp Leu Met Ala Leu
            610                 615                 620

Leu Gly Lys Asn Thr Met Ala Glu Ala Ser Lys Glu Leu His Ala Ile
625                 630                 635                 640

Asn Pro Gly Ile Val Leu Tyr Gly Glu Pro Trp Thr Gly Gly Thr Ser
            645                 650                 655

Gly Ile Thr Gly Asp Gln Leu Leu Thr Lys Gly Val Gln Lys Gly Leu
            660                 665                 670

Gly Ile Gly Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Arg Gly Val Glu Gly Ser Ile Asn Asp Phe Thr
705                 710                 715                 720

Ser Ser Pro Ser Glu Thr Ile Asn Tyr Val Ser Cys His Asp Asn Tyr
            725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
            770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
            900                 905                 910
```

```
Ser Met Met Ile Leu His Gln Glu Val Ser Pro Asp His Gly Lys Lys
        915                 920                 925

<210> SEQ ID NO 27
<211> LENGTH: 928
<212> TYPE: PRT
<213> ORGANISM: Artificial
<220> FEATURE:
<223> OTHER INFORMATION: Hybrid pullulanase

<400> SEQUENCE: 27

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
    50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
            115                 120                 125

Ser Pro Met Thr Leu Thr Asp Gly Ala Ser Gly Phe Thr Val Thr Asp
    130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
        195                 200                 205

Gln Tyr Lys Val Ala Leu Asp His Ser Trp Ser Ala Ser Tyr Pro Asn
    210                 215                 220

Asn Asn Val Asn Leu Thr Val Pro Ala Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ala Gly Thr Gln Ser Asp Leu Val
            260                 265                 270

Gln Leu Thr Leu Ala Ser Ala Pro Asp Ile Thr His Asp Leu Gln Val
        275                 280                 285

Val Ala Asp Gly Tyr Lys Gly Gly Lys Ile Leu Pro Arg Asn Val Leu
    290                 295                 300

Asn Leu Pro Arg Tyr Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
            340                 345                 350
```

```
Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
        370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
            420                 425                 430

Ile Tyr Glu Val His Val Arg Asp Phe Ser Ile Asp Ala Asn Ser Gly
        435                 440                 445

Met Lys Asn Lys Gly Lys Tyr Leu Ala Phe Thr Glu His Gly Thr Lys
    450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
                485                 490                 495

Glu Thr Gln Pro Asn Met Tyr Asn Trp Gly Tyr Asp Pro Arg Asn Tyr
            500                 505                 510

Asn Val Pro Glu Gly Ala Tyr Ala Thr Thr Pro Glu Gly Thr Ala Arg
        515                 520                 525

Ile Thr Glu Phe Lys Gln Leu Ile Gln Ser Ile His Lys Asp Arg Ile
    530                 535                 540

Ala Ile Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
    610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Glu Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
        675                 680                 685

Val Phe Asp Ser Ser Ala Gln Gly Phe Ala Thr Gly Ala Thr Gly Leu
    690                 695                 700

Thr Asp Ala Ile Lys Arg Gly Val Glu Gly Ser Ile Asn Asp Phe Thr
705                 710                 715                 720

Ser Ser Pro Ser Glu Thr Ile Asn Tyr Val Ser Cys His Asp Asn Tyr
                725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
        755                 760                 765
```

Gln Gly Val Pro Phe Met Gln Gly Glu Glu Met Leu Arg Thr Lys
770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
                820                 825                 830

Ala Asn Glu Ile Asn Ser His Leu Gln Phe Leu Asn Ser Pro Glu Asn
                835                 840                 845

Thr Val Ala Tyr Glu Leu Thr Asp His Val Asn Lys Asp Lys Trp Gly
                850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
                900                 905                 910

Ser Met Met Ile Leu His Gln Glu Val Ser Pro Asp His Gly Lys Lys
                915                 920                 925

<210> SEQ ID NO 28
<211> LENGTH: 828
<212> TYPE: PRT
<213> ORGANISM: Artificial
<220> FEATURE:
<223> OTHER INFORMATION: Hybrid of P008 and CD from P306

<400> SEQUENCE: 28

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
                20                  25                  30

Gly Asn Gly Ala Ala Tyr Glu Phe Ser Gly Lys Asp Asp Phe Gly Val
                35                  40                  45

Lys Ala Asp Val Gln Val Pro Gly Asp Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Ala Thr Pro Lys
                100                 105                 110

Val Ser Asn Ala Tyr Leu Asp Asn Glu Lys Thr Val Leu Ala Lys Leu
                115                 120                 125

Thr Asn Pro Met Thr Leu Ser Asp Gly Ser Ser Gly Phe Thr Val Thr
130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
                180                 185                 190

Tyr Glu Ala Val Asn Leu Ile Pro Arg Asn Val Leu Asn Leu Pro Arg
                195                 200                 205

-continued

Tyr Tyr Tyr Ser Gly Asn Asp Leu Gly Asn Val Tyr Ser Asn Lys Ala
210             215             220

Thr Ala Phe Arg Val Trp Ala Pro Thr Ala Ser Asp Val Gln Leu Leu
225             230             235             240

Leu Tyr Asn Ser Glu Thr Gly Pro Val Thr Lys Gln Leu Glu Met Gln
            245             250             255

Lys Ser Asp Asn Gly Thr Trp Lys Leu Lys Val Pro Gly Asn Leu Lys
            260             265             270

Asn Trp Tyr Tyr Leu Tyr Gln Val Thr Val Asn Gly Lys Thr Gln Thr
        275             280             285

Ala Val Asp Pro Tyr Val Arg Ala Ile Ser Val Asn Ala Thr Arg Gly
290             295             300

Met Ile Val Asp Leu Glu Asp Thr Asn Pro Pro Gly Trp Lys Glu Asp
305             310             315             320

His Gln Gln Thr Pro Ala Asn Pro Val Asp Glu Val Ile Tyr Glu Val
                325             330             335

His Val Arg Asp Phe Ser Ile Asp Ala Asn Ser Gly Met Lys Asn Lys
            340             345             350

Gly Lys Tyr Leu Ala Phe Thr Glu His Gly Thr Lys Gly Pro Asp Gly
        355             360             365

Val Lys Thr Gly Ile Asp Ser Leu Lys Glu Leu Gly Ile Asn Ala Val
370             375             380

Gln Leu Gln Pro Ile Glu Glu Phe Ala Ser Ile Asp Glu Thr Gln Pro
385             390             395             400

Asn Met Tyr Asn Trp Gly Tyr Asp Pro Arg Asn Tyr Asn Val Pro Glu
                405             410             415

Gly Ala Tyr Ala Thr Thr Pro Glu Gly Thr Ala Arg Ile Thr Glu Phe
            420             425             430

Lys Gln Leu Ile Gln Ser Ile His Lys Asp Arg Ile Ala Ile Asn Met
        435             440             445

Asp Val Val Tyr Asn His Thr Phe Ala Thr Gln Ile Ser Asp Phe Asp
450             455             460

Lys Ile Val Pro Glu Tyr Tyr Arg Thr Asp Asp Ala Gly Asn Tyr
465             470             475             480

Thr Asn Gly Ser Gly Thr Gly Asn Glu Ile Ala Ala Glu Arg Pro Met
            485             490             495

Val Gln Lys Phe Ile Ile Asp Ser Leu Lys Tyr Trp Val Asn Glu Tyr
        500             505             510

His Ile Asp Gly Phe Arg Phe Asp Leu Met Ala Leu Leu Gly Lys Asp
    515             520             525

Thr Met Ser Lys Ala Ala Ser Glu Leu His Ala Ile Asn Pro Gly Ile
530             535             540

Ala Leu Tyr Gly Glu Pro Trp Thr Gly Gly Thr Ser Ala Leu Pro Glu
545             550             555             560

Asp Gln Leu Leu Thr Lys Gly Ala Gln Lys Gly Met Gly Val Ala Val
            565             570             575

Phe Asn Asp Asn Leu Arg Asn Ala Leu Asp Gly Asn Val Phe Asp Ser
            580             585             590

Ser Ala Gln Gly Phe Ala Thr Gly Ala Thr Gly Leu Thr Asp Ala Ile
        595             600             605

Lys Arg Gly Val Glu Gly Ser Ile Asn Asp Phe Thr Ser Ser Pro Ser
610             615             620

Glu Thr Ile Asn Tyr Val Ser Cys His Asp Asn Tyr Thr Leu Trp Asp

-continued

```
625                 630                 635                 640
Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
                660                 665                 670

Phe Met Gln Gly Gly Glu Gly Met Leu Arg Thr Lys Gly Gly Asn Asp
                675                 680                 685

Asn Ser Tyr Asn Ala Gly Asp Thr Val Asn Glu Phe Asp Trp Ser Arg
                690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
                740                 745                 750

Glu Leu Thr Asp His Val Asn Lys Asp Lys Trp Gly Asn Ile Ile Val
                755                 760                 765

Val Tyr Asn Pro Asn Lys Thr Ala Ala Thr Ile Asn Leu Pro Ser Gly
    770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
                805                 810                 815

Leu His Gln Glu Val Ser Pro Asp His Gly Lys Lys
                820                 825
```